(12) United States Patent
Maruoka

(10) Patent No.: US 8,716,524 B2
(45) Date of Patent: *May 6, 2014

(54) OPTICALLY ACTIVE QUATERNARY AMMONIUM SALT HAVING AXIAL ASYMMETRY AND PROCESS FOR PRODUCING A-AMINO ACID AND DERIVATIVE THEREOF WITH THE SAME

(75) Inventor: Keiji Maruoka, Kyoto (JP)

(73) Assignee: Nagase & Co., Ltd, Osaka (JP)

( * ) Notice: Subject to any disclaimer, the term of this patent is extended or adjusted under 35 U.S.C. 154(b) by 58 days.

This patent is subject to a terminal disclaimer.

(21) Appl. No.: 13/039,645

(22) Filed: Mar. 3, 2011

(65) Prior Publication Data
US 2011/0152562 A1 Jun. 23, 2011

Related U.S. Application Data

(66) Division of application No. 10/587,467, Substitute for application No. PCT/JP2005/001623, filed on Jan. 27, 2005, now Pat. No. 7,928,224.

(30) Foreign Application Priority Data

Jan. 30, 2004 (JP) ................. 2004-023317
Mar. 1, 2004 (JP) ................. 2004-056659

(51) Int. Cl.
*C07C 229/08* (2006.01)

(52) U.S. Cl.
USPC ........................................................ 562/575

(58) Field of Classification Search
CPC .................................................. C07C 227/32
See application file for complete search history.

(56) References Cited

U.S. PATENT DOCUMENTS

| 6,340,753 | B1 | 1/2002 | Maruoka | |
|---|---|---|---|---|
| 6,441,231 | B1* | 8/2002 | Maruoka | .................. 564/35 |
| 2002/0065414 | A1 | 5/2002 | Maruoka | |
| 2006/0183896 | A1 | 8/2006 | Maruoka | |
| 2007/0135654 | A1 | 6/2007 | Maruoka | |
| 2007/0161624 | A1 | 7/2007 | Maruoka | |
| 2009/0054679 | A1 | 2/2009 | Maruoka et al. | |
| 2009/0270614 | A1 | 10/2009 | Maruoka et al. | |
| 2010/0029935 | A1 | 2/2010 | Maruoka et al. | |
| 2012/0095218 | A1 | 4/2012 | Maruoka et al. | |
| 2012/0095252 | A1 | 4/2012 | Maruoka et al. | |
| 2012/0101309 | A1 | 4/2012 | Maruoka et al. | |
| 2012/0101310 | A1 | 4/2012 | Maruoka et al. | |
| 2012/0108846 | A1 | 5/2012 | Maruoka et al. | |

FOREIGN PATENT DOCUMENTS

| EP | 1 854 796 A1 | 11/2007 |
|---|---|---|
| EP | 1870403 | 12/2007 |
| JP | 2001-48866 | 2/2001 |
| JP | 2002-173492 | 6/2002 |
| JP | 2002-326992 | 11/2002 |
| JP | 2003-081976 | 3/2003 |
| JP | 2004-189696 | 7/2004 |
| JP | 2004-238362 | 8/2004 |
| JP | 2004-359578 | 12/2004 |
| JP | 2005-41791 | 2/2005 |
| WO | 2006054366 A | 5/2006 |
| WO | 2006/093269 | 9/2006 |
| WO | 2006/104226 | 10/2006 |

OTHER PUBLICATIONS

Greene, Protective Groups in Organic Chemistry, 1981, John Wiley & Sons, New York, pp. 168-169.*
Mason, et al., Optical Activity in the Biaryl Series, Tetrahedron, vol. 30, No. 12, pp. 1671-1682, 1974, Great Britian.
Kano, et al., Design of New Polyamine-based Chiral Phase-Transfer Catalysts for the Enantioselective Synthesis of Phenylalanine, Tetrahedron: Asymmetry, vol. 15, No. 8, pp. 1243-1245, 2004, Japan.
Ikunaka, et al., A Scalable Synthesis of (R)-3,5-Dihydro-4H-dinaphth[2,1-c:1'2'-e]azepine, Organic Process Research & Development, vol. 7, No. 5, pp. 644-648, 2003, Japan.
Kitamura, et al., Powerful Chiral Phase-Transfer Catalysts for the Asymmetric Synthesis of a-Alkyl-and a,a-Dialkyl-a-amino Acids, Angew. Chem. Int. Ed., vol. 44, pp. 1549-1551, 2005.
International Search Report for PCT/JP2005/001623, Dated Mar. 22, 2005.
International Preliminary Examination Report for PCT/JP2005/001623.
Bellier, et al., Synthesis and Biological Properties of New Constrained CCK-B Antagonists: Discrimination of Two Affinity States of the CCK-B Receptor on Transfected CHO Cells, J. Med. Chem., vol. 40, No. 24, pp. 3947-3956, 1997.
Shioiri, et al., Asymmetric Phase Transfer Catalysis, Stimulating Concepts in Chemistry, pp. 123-143, 2000, Wiley-VCH, Weinheim.
Ooi, et al., Practical Catalytic Enantioselective Synthesis of a,a-Dialkyl-a-Amino Acids by Chiral Phase-Transfer Catalysis, J. Am. Chem. Soc., vol. 122, pp. 5228-5229, 2000.
Seki, et al., A Practical Synthesis of C2-Symmetric Chiral Binaphthyl Ketone Catalyst, Synthesis, No. 12, pp. 1677-1680, 2000.

(Continued)

*Primary Examiner* — Paul A Zucker
(74) *Attorney, Agent, or Firm* — Amin, Turocy & Watson, LLP

(57) ABSTRACT

The present invention provides a compound of the following formula (I) below. This compound (I) can be produced by reacting a 2,2'-dimethylene bromide-1,1'-binaphthyl derivative, which can be produced by a relatively small number of processes, with an easily available secondary amine. This compound (I) is useful as a chiral phase-transfer catalyst.

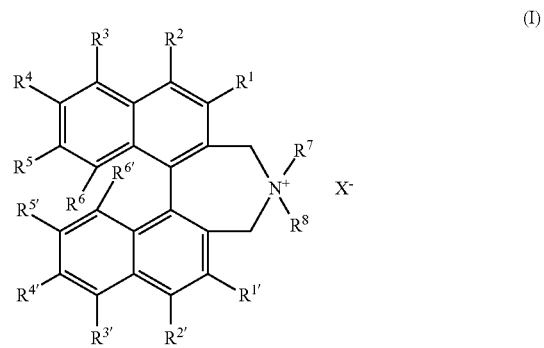

9 Claims, No Drawings

(56) References Cited

OTHER PUBLICATIONS

Ooi, et al., New, Improved Procedure for the Synthesis of Structurally Diverse N-Spiro C2-Symmetric Chiral Quaternary Ammonium Bromides, J. Org. Chem., vol. 68, pp. 4576-4578, 2003.
Ooi et al., Synlett., No. 12, p. 1931-1933, 2003.
Reitz et al., Holzforschung, vol. 55, No. 2, p. 171-175, 2001.
Schmidt et al., Ann. Chem., vol. 576, p. 85-93, 1952.
Costero et al., Anales de Quimica, vol. 89, No. 1, p. 95-98, 1993.
Wang et al., Tetrahedron, vol. 63, No. 26, p. 6042-6050, 2007.
Wang et al., Organic Process Research & Development, vol. 11, No. 3, p. 628-632, 2007.
Arimura et al., The Chemical Society of Japan, Dai 86 Shunki Nenkai (2006), Koen Yokoshu II, p. 1073, Mar. 13, 2006.
Belokon et al., Tetrahedron, vol. 60, No. 8, p. 1849-1861, 2004.
Chen et al., Youji Huaxue, vol. 8, No. 2, p. 164-166, 1988.
Maruoka et al., Chemical Reviews, vol. 103, No. 8, p. 3013-3028, 2003.
Bey et al., Tetrahedron Letter, vol. 18, No. 17, p. 1455-1458, 1977.
O'Donnell et al., J. Am. Chem. Soc., vol. 111, p. 2353-2355, 1989.
Park et al., J. Org. Chem. vol. 70, p. 1904-1906, 2005.
U.S. Office Action dated Oct. 19, 2009 corresponding to U.S. Appl. No. 10/587,467, filed Jul. 24, 2006.
U.S. Office Action dated May 21, 2010 corresponding to U.S. Appl. No. 10/587,467, filed Jul. 24, 2006.
U.S. Office Action dated Jan. 13, 2011 corresponding to U.S. Appl. No. 11/626,228, filed Jan. 23, 2007.
Hewgill et al., J. Chem. Soc. Perkin Trans. I, Issue 6, Jan. 1988, pp. 1305-1311.
Bellier, et al., Synthesis and Biological Properties of New Constrained CCK-B Antagonists: Discrimination of Two Affinity States of the CCK-B Receptor on Transfected CHO Cells, J. Med. Chem., vol. 40, No. 24, pp. 3947-3956, 1997, Paris, France.
Mossel, et al., Aspartame Dipeptide Analogues: Effect of Number of Side-Chain Methylene Group Spacers and C-Methylation in the Second Position, Tetrahedron Asymmetry, vol. 8, pp. 1305-1314, 1997.
Shioiri, et al., Asymmetric Phase Transfer Catalysis, Stimulating Concepts in Chemistry, pp. 123-143, 2000, Japan.
O'Donnell, The Preparation of Optically Active a-Amino Acids From the Benzophenone Imines of Glycine Derivatives, M. J. Aldrichimica Acta, vol. 34, No. 1, pp. 3-15, 2001.
Ooi, et al., Practical Catalytic Enantioselective Synthesis of a,a-Dialkyl-a-Amino Acids by Chiral Phase-Transfer Catalysis, J. Am. Chem. Soc., vol. 122, pp. 5228-5229, 2000, Japan.
Seki, et al., A Practical Synthesis of C2-Symmetric Chiral Binaphthyl Ketone Catalyst, Synthesis, No. 12, pp. 1677-1680, 2000, Japan.
Ooi, et al., New, Improved Procedure for the Synthesis of Structurally Diverse N-Spiro C2-Symmetric Chiral Quaternary Ammonium Bromides, J. Org. Chem., vol. 68, pp. 4576-4578, 2003, Japan.
Ooi, et al., Design of N-Spiro C2-Symmetric Chiral Quaternary Ammonium Bromides as Novel Chiral Phase-Transfer Catalysts: Synthesis and Application to Practical Asymmetric Synthesis of a-Amino Acids, J. Am. Chem. Soc., vol. 125, No. 17, pp. 5139-5151, 2003, Japan.
Ooi, et al., Molecular Design of a C2-Symmetric Chiral Phase-Transfer Catalyst for Practical Asymmetric Synthesis of a-Amino Acids, J. Am. Chem. Soc., vol. 121, No. 27, pp. 6519-6520, 1999, Japan.
Abbott, et al., Electrochemical Recognition of Charged Species Using Quaternary Ammonium Binaphthyl Salts, A.P., Analyst, vol. 126, No. 11, pp. 1892-1896, 2001 UK.
Stara, et al., Nucleophilic Cleavage of 4,5-Dihydro-3H-dinaphth[2,1-c:1',2'-e]azepinium Quaternary Salts. A Convenient Approach to New Axially Dissymmetric and Axially Asymmetric Ligands, J. Org. Chem., vol. 57, No. 25, pp. 6966-6969, 1992, Czechoslovakia.
Stara, et al., Stereochemical Dichotomy in the Stevens Rearrangement of Axially Twisted Dihydroazepinium and Dihydrothiepinium Salts. A Novel Enantioselective Synthesis of Pentahelicene, J. Am. Chem. Soc., vol. 116, No. 12, pp. 5084-5088, 1994.
Stara, et al., 4,5-Dihydro-4-alkyl-3H-dinaphtho[2,1-c:1'2'-e]thiepinium Salts. A Convenient Approach to New 2,2'- Bidentate 1,1'-Binaphthalene Ligands with Sulfur Donor Atoms, J. Org. Chem., vol. 59, No. 6, pp. 1326-1332, 1994.

Stara, et al., Optically Pure (S)- and (R)-4,5-Dihydro-3H-4-Methyldinaphth[2,1'-c; 1,2'-e]Azepines. Application to the Synthesis of New Bidentate Ligands with Axial Asymmetry, Tetrahedron: Asymmetry, vol. 3, No. 11, pp. 1365-1368, 1992, Great Britian.
Cottineau, et al., Reductive Cleavage of Axially Dismmetric Tertiary Amines and Quaternary Ammonium Salts by Lithium Aluminium Hydride. Synthesis of New 1,1'-Binaphthyl Substituted Amines, Tetrahedron Letters, vol. 26, No. 4, pp. 421-424, 1985, Great Britian.
Di Bari, et al., Conformational Study of 2,2'-Homosubstituted 1,1'-Binaphthyls by Means of UV and CD Spectroscopy, J. Am. Chem. Soc., vol. 121, No. 35, pp. 7998-8004, 1999, Italy.
Shi, et al., Synthesis of Axially Dissymmetric Chiral Ammonium Salts by Quaternization of Secondary Amines with (R)-(+)-2,2'-Bis(bromomethyl)-6,6'-dinitrobiphenyl and (R)-(+)-2,2'-Bis(bromomethyl)-1,1'-binaphthyl and an Examination of Their Abilities as Chiral Phase-transfer Catalysts, Journal of Chemical Research, Synopses, No. 2, pp. 46-47, 1995, Japan.
Ooi, et al., Design of N-Spiro C2-Symmetric Chiral Quaternary Ammonium Bromides as Novel Chiral Phase-Transfer Catalysts: Synthesis and Application to Practical Asymmetric Synthesis of a-Amino Acids, J. Am. Chem. Soc., vol. 125, No. 17, pp. 5139-5151, 2003.
Ooi, et al., Molecular Design of a C2-Symmetric Chiral Phase-Transfer Catalyst for Practical Asymmetric Synthesis of a-Amino Acids, J. Am. Chem. Soc., vol. 121, No. 27, pp. 6519-6520, 1999.
Stara, et al., Nucleophilic Cleavage of 4,5-Dihydro-3H-dinaphth[2,1-c:1',2'-e]azepinium Quaternary Salts. A Convenient Approach to New Axially Dissymmetric and Axially Asymmetric Ligands, J. Org. Chem., vol. 57, No. 25, pp. 6966-6969, 1992.
Di Bari, et al., Conformational Study of 2,2'-Homosubstituted 1,1'-Binaphthyls by Means of UV and CD Spectroscopy, J. Am. Chem. Soc., vol. 121, No. 35, pp. 7998-8004, 1999.
Shi, et al., Synthesis of Axially Dissymmetric Chiral Ammonium Salts by Quaternization of Secondary Amines with (R)-(+)-2,2'-Bis(bromomethyl)-6,6'-dinitrobiphenyl and (R)-(+)-2,2'-Bis(bromomethyl)-1,1'-binaphthyl and an Examination of Their Abilities as Chiral Phase-transfer Catalysts, Journal of Chemical Research, Synopses, No. 2, pp. 46-47, 1995.
Kano, et al., Design of New Polyamine-based Chiral Phase-Transfer Catalysts for the Enantioselective Synthesis of Phenylalanine, Tetrahedron: Asymmetry, vol. 15, No. 8, pp. 1243-1245, 2004.
Ikunaka, et al., A Scalable Synthesis of (R)-3,5-Dihydro-4H-dinaphth[2,1-c:1'2'-e]azepine, Organic Process Research & Development, vol. 7, No. 5, pp. 644-648, 2003.
Keiji Maruoka, TCI Mail, Jul. 2001, No. 111. pp. 2-19.
European Search Report corresponding to U.S. Appl. No. 10/587,467 mailed on Jul. 8, 2009.
Abbott, et al. Electrochemical recognition of analytes using quaternary ammonium binaphthyl salts. XP002532001. 2003.
Fitts, et al. Configurational studies in the biphenyls. Configurational correlation of biaryls by optical displacement. The absolute configuration of restricted 1,1'-binaphthyls. XP002532002. 1958.
Shi, et al. Synthesis of axially quaternization of secondary amines with (R)-(+)-2,2'-bis(bromomethyl)-1,1'-binapht as chiral phase-transfer catalysts. XP002532003. 1995.
XP002532004. 1955.
XP002532005. 2006.
U.S. Office Action dated May 3, 2010 corresponding to U.S. Appl. No. 11/626,228, filed Jan. 23, 2007.
Ahmed et al., Chemical Abstract 53:2119, OREF 53: 405c-i, 406a, Journal of the Chemical Society, p. 3043-3047, 1958.
Ahmed et al., Chemical Abstract 55:38083, OREF 55: 7430c-f, Journal of the Chemical Society, p. 4165-4169, 1960.
Beaven et al., Chemical Abstract 46:67079, OREF 46: 11211e-i, 11212a-I, Journal of the Chemical Society, vol. 46, p. 854-868, 1952.
Han et al., Tetrahedron Letters, vol. 46, No. 49, p. 8555-8558, 2005.
Insole, Journal of the Chemical Society. Perkin transactions 2: physical organic chemistry, No. 9, p. 1168-1173, 1972.
Kashiwada et al., Journal of Medical Chemistry, vol. 37, No. 1, p. 195-200, 1994.
Lygo et al., Tetrahedron Letters, vol. 44, No. 30, p. 5629-5632, 2003.

\* cited by examiner

OPTICALLY ACTIVE QUATERNARY AMMONIUM SALT HAVING AXIAL ASYMMETRY AND PROCESS FOR PRODUCING A-AMINO ACID AND DERIVATIVE THEREOF WITH THE SAME

CROSS REFERENCE TO RELATED APPLICATIONS

This application is a Division of U.S. Pat. No. 7,928,224 filed on Jul. 24, 2006, which is a U.S. National Phase entry of PCT International Application No. PCT/JP2005/001623 filed on Jan. 27, 2005, which claims the benefit and priority of Japanese applications 2004-023317 filed on Jan. 30, 2004 and 2004-056659 filed on Mar. 1, 2004, all of which are hereby incorporated by reference.

TECHNICAL FIELD

The present invention relates to an optically active quaternary ammonium salt having axial asymmetry and a method for producing the same. The present invention further relates to a method for producing an optically active α-amino acid and derivatives thereof, by using this optically active quaternary ammonium salt having axial asymmetry as a phase-transfer catalyst.

BACKGROUND ART

α-Alkyl-α-amino acids represented by the formula $H_2NCH(R)COOH$ are very important naturally occurring amino acids. Most of the α-alkyl-α-amino acids exist in animals, plants, microorganisms or the like in the L-form having a L-configuration at α position carbon, and the L-form constitutes a polypeptide chain. On the other hand, the D-form exists in plants, fungi or microorganisms as a non-protein compound. Furthermore, α,α-dialkyl-α-amino acids represented by a formula $H_2NC(R)(R')COOH$ are compounds that are recently gaining attention because of their unique functions such as being stereochemically stable and being not susceptible to enzymatic hydrolysis by protease when the compound is incorporated into a peptide. Regarding the above-described respects, see Bellier, B, et al., J. Med. Chem., vol. 40, p. 3947, 1997; and Mossel, E. et al., Tetrahedron Asymmetry, vol. 8, p. 1305, 1997. The compounds can be used, for example, as peptides having an enhanced activity, effective enzyme inhibitors, and chiral building blocks for synthesizing compounds having various biological activities. Such α,α-dialkyl-α-amino acids have been examined to be prepared by catalystic asymmetric reaction, but at present, no effective method for preparing the same has been found out.

For example, the significance of chiral phase-transfer catalysts, which allow stereoselective alkylation of glycine derivatives, is increased in the field of process chemistry because of its easy application. A large number of researches as to design of phase-transfer catalysts have been conducted by using mainly cinchona alkaloid derivatives until now and several useful methods have been reported (e.g., see Shioiri, T. et al., Stimulating Concepts in Chemistry, edited by Vogtle, F. et al., WILEY-VCR: Weinheim, p. 123, 2000; and O'Donnell, M. J., Aldrichimica Acta, vol. 34, p. 3, 2001). However, when such phase-transfer catalysts are used, various problems are caused such as use of a halogen-based solvent, a long time reaction, or the necessity of low temperature conditions. In particular, for synthesizing α,α-dialkyl-α-amino acids as described above, chiral phase-transfer catalysts derived from such cinchona alkaloid are not very useful.

The present inventors have prepared an optically active quaternary ammonium salt having axial asymmetry, and clarified that it can be used as a phase-transfer catalyst for synthesizing stereoselectively α-amino acids as described above (see Japanese Laid-Open Patent Publication No. 2001-48866; Japanese Laid-Open Patent Publication No. 2003-81976; and Ooi, T. et al., J. Am. Chem. Soc., vol. 122, p. 5228, 2000). For example, a spiro-compound represented by the following formula is very useful for asymmetric double alkylation of glycine derivatives and asymmetric monoalkylation of α-alkyl-α-amino acid derivatives (e.g., alanine derivatives):

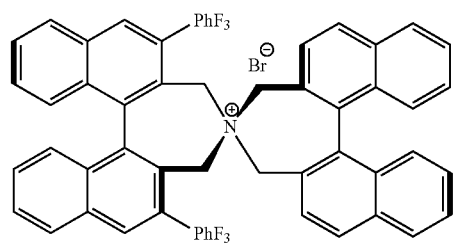

(where $PhF_3$ represents 3,4,5-trifluorophenyl group). However, a large number of processes are required in order to prepare such spiro catalysts, and for example, when chiral binaphthol, which is easily available, is used as the starting raw material, as many as eleven processes are required only to prepare the structural portion on the left side of the catalyst. Thus, preparation takes time and labor, and results in high cost, which are large drawbacks.

DISCLOSURE OF INVENTION

The purpose of the present invention is to provide a chiral phase-transfer catalyst having a simplified structure that can be produced by a fewer number of processes.

The present invention provides a compound represented by the following formula (I) below:

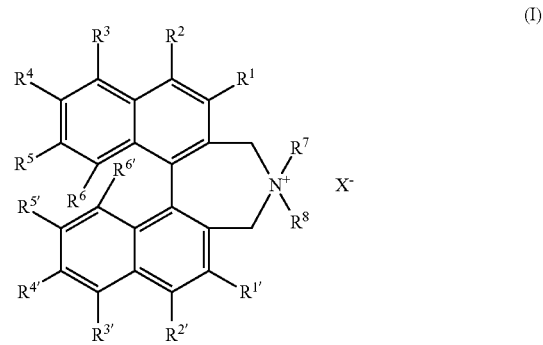

wherein $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are groups independently selected from the group consisting of:
 (i) a hydrogen atom;
 (ii) —$NR^{20}R^{21}$ (where $R^{20}$ and $R^{21}$ are each independently a hydrogen atom or a $C_1$ to $C_4$ alkyl group);
 (iii) a cyano group;
 (iv) a nitro group;
 (v) a carbamoyl group;
 (vi) an N—($C_1$ to $C_4$ alkyl)carbamoyl group;

(vii) an N,N-di($C_1$ to $C_4$ alkyl)carbamoyl group;
(viii) —NHCOR$^9$ (where R$^9$ is a $C_1$ to $C_4$ alkyl group that may be branched);
(ix) a $C_1$ to $C_6$ alkyl group that may be branched or form a cyclic group;
(x) a $C_2$ to $C_6$ alkenyl group that may be branched or form a cyclic group;
(xi) a $C_2$ to $C_6$ alkynyl group that may be branched or form a cyclic group;
(xii) an aralkyl group, wherein the aryl moiety of the aralkyl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
  a cyano group,
  —NR$^{20}$R$^{21}$ (where R$^{20}$ and R$^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where R$^9$ is a $C_1$ to $C_4$ alkyl group that may be branched), and
  a halogen atom;
(xiii) a heteroaralkyl group having a heteroaryl moiety, wherein the heteroaryl moiety may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
  a cyano group,
  —NR$^{20}$R$^{21}$ (where R$^{20}$ and R$^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where R$^9$ is a $C_1$ to $C_4$ alkyl group that may be branched), and
  a halogen atom;
(xiv) an aryl group, wherein the aryl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
  a cyano group,
  —NR$^{20}$R$^{21}$ (where R$^{20}$ and R$^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where R$^9$ is a $C_1$ to $C_4$ alkyl group that may be branched),
  a halogen atom, and
  —S(O)$_n$—R (where n is 0, 1 or 2, and R is a $C_1$ to $C_4$ alkyl group that may be branched);
or may be substituted with —O—(CH$_2$)$_m$—O— (where m is 1 or 2) at positions 3 and 4 taken together; and
(xv) a heteroaryl group, wherein the heteroaryl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
  a cyano group,
  —NR$^{20}$R$^{21}$ (where R$^{20}$ and R$^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where R$^9$ is a $C_1$ to $C_4$ alkyl group that may be branched), and
  a halogen atom;
R$^7$ and R$^9$ are groups independently selected from the group consisting of:
  (i) a hydrogen atom;
  (ii) a $C_1$ to $C_{12}$ alkyl group that may be branched or form a cyclic group;
  (iii) a $C_2$ to $C_{12}$ alkenyl group that may be branched or form a cyclic group;
  (iv) a $C_2$ to $C_{12}$ alkynyl group that may be branched or form a cyclic group;
  (v) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(vi) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(vii) —(CH$_2$)$_n$OCONR$^{10}$R$^{11}$ (where R$^{10}$ and R$^{11}$ are groups independently selected from the group consisting of:
(1) a hydrogen atom;
(2) a $C_1$ to $C_4$ alkyl group that may be branched;
(3) a $C_2$ to $C_6$ alkenyl group that may be branched or form a cyclic group;
(4) a $C_2$ to $C_6$ alkynyl group that may be branched or form a cyclic group;
(5) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(6) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(7) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and
(8) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(viii) —(CH$_2$)$_n$CONR$^{12}$R$^{13}$ (where R$^{12}$ and R$^{13}$ are groups independently selected from the group consisting of:
(1) a hydrogen atom;
(2) a $C_1$ to $C_4$ alkyl group that may be branched;

(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_4$ to $C_4$ alkyl group that may be branched), and
a halogen atom;
and n is an integer from 1 to 12);

(ix) —$(CH_2)_nNR^{12}COR^{13}$ (where $R^{12}$ and $R^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(xi) —(CH$_2$)$_n$Y—OR$^{12}$ (where Y is a $C_1$ to $C_4$ divalent saturated hydrocarbon group that may be branched, and R$^{12}$ is a group selected from the group consisting of:
  (1) a hydrogen atom;
  (2) a $C_1$ to $C_4$ alkyl group that may be branched;
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom; and
  (4) a heteroaryl group, wherein the heteroaryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
and n is an integer from 1 to 12);

(xii) —(CH$_2$)$_n$—OR$^{12}$ (where R$^{12}$ is a group selected from the group consisting of:
  (1) a hydrogen atom;
  (2) a $C_1$ to $C_4$ alkyl group that may be branched;
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom; and
  (4) a heteroaryl group, wherein the heteroaryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
and n is an integer from 1 to 12);

(xiii) —(CH$_2$)$_n$—S—R$^{12}$ (where R$^{12}$ is a group selected from the group consisting of:
  (1) a hydrogen atom;
  (2) a $C_1$ to $C_4$ alkyl group that may be branched;
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(xiv) —(CH$_2$)$_n$—SO—R$^{12}$ (where R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_4$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12); and
(xv) —(CH$_2$)$_n$—SO$_2$—R$^{12}$ (where R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group, an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12); or R$^7$ and R$^8$ are taken together to form a divalent group selected from the group consisting of: —(CH$_2$)$_m$— (where m is an integer from 2 to 8);

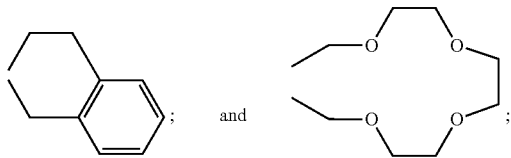

X$^-$ is an anion selected from the group consisting of a halide anion, SCN$^-$, HSO$_4^-$ and HF$_2^-$.

In one embodiment, R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ of the compound represented by the formula (I) are groups independently selected from the group consisting of:
  (i) a hydrogen atom;
  (xiv) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched),
    a halogen atom, and
    —S(O)$_n$—R (where n is 0, 1 or 2, and R is a $C_1$ to $C_4$ alkyl group that may be branched);
  or may be substituted with —O—(CH$_2$)$_m$—O— (where m is 1 or 2) at positions 3 and 4 taken together; and
  (xv) a heteroaryl group, wherein the heteroaryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom.

In a further embodiment, R$^1$—, R$^{1'}$, R$^2$, R$^{2'}$, R$^3$, R$^{3'}$, R$^4$, R$^{4'}$, R$^5$, R$^{5'}$, R$^6$, and R$^{6'}$ of the compound represented by the formula (I) are groups independently selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group.

In a further embodiment, the compound represented by the formula (I) is a compound represented by the following formula (I'):

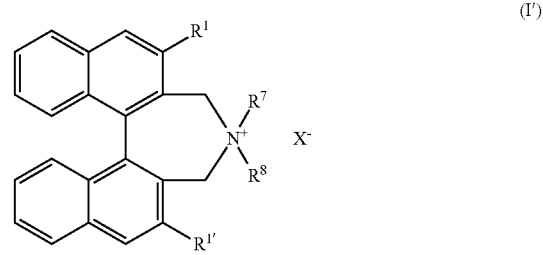

(where R$^1$ and R$^{1'}$ are groups independently selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group, and R$^7$, R$^8$ and X$^-$ are groups independently as defined in claim 1).

In one embodiment, R$^7$ and R$^8$ of the compound represented by the formula (I) are groups independently selected from the group consisting of:
  (ii) a $C_1$ to $C_{12}$ alkyl group that may be branched or form a cyclic group; and
  (xii) —(CH$_2$)$_n$—OR$^{12}$ (where R$^{12}$ is a group selected from the group consisting of:
    (1) a hydrogen atom,
    (2) a $C_1$ to $C_4$ alkyl group that may be branched,
    (3) an aryl group, wherein the aryl group may be substituted with at least one group selected from the group consisting of:
      a $C_1$ to $C_4$ alkyl group that may be branched,
      a $C_1$ to $C_5$ alkoxy group that may be branched,
      an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom, and (4) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom, and n is an integer of 1 to 12).

In another embodiment, R$^7$ and R$^8$ of the compound represented by the formula (I) are groups independently selected from the group consisting of a methyl group, an ethyl group, an n-butyl group, an isobutyl group, an n-decyl group, and a cyclohexyl group.

In a further embodiment, R$^7$ and R$^8$ of the compound represented by the formula (I) are the same.

In another embodiment, R$^7$ and R$^8$ of the compound represented by the formula (I) are taken together to form a divalent group selected from the group consisting of: —(CH$_2$)$_m$— (where m is an integer from 2 to 8);

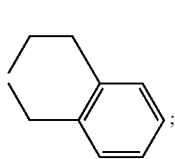 ; and 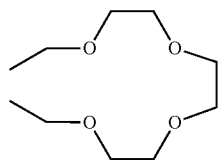 .

The present invention also provides a method for producing the compound represented by the formula (I), the method comprises:

a step of reacting a compound represented by the following formula (II):

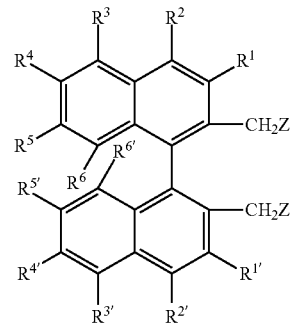

with a secondary amine represented by the following formula (III):

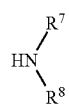

in an organic solvent in the presence of an acid scavenging agent, wherein in the formula (II), R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are groups independently selected from the group consisting of:

(i) a hydrogen atom;

(ii) —NR$^{20}$R$^{21}$ (where R$^{20}$ and R$^{21}$ are each independently a hydrogen atom or a $C_1$ to $C_4$ alkyl group);

(iii) a cyano group;

(iv) a nitro group;

(v) a carbamoyl group;

(vi) an N—($C_1$ to $C_4$ alkyl)carbamoyl group;

(vii) an N,N-di($C_1$ to $C_4$ alkyl)carbamoyl group;

(viii) —NHCOR$^9$ (where R$^9$ is a $C_1$ to $C_4$ alkyl group that may be branched);

(ix) a $C_1$ to $C_6$ alkyl group that may be branched or form a cyclic group;

(x) a $C_2$ to $C_6$ alkenyl group that may be branched or form a cyclic group;

(xi) a $C_2$ to $C_6$ alkynyl group that may be branched or form a cyclic group;

(xii) an aralkyl group, wherein the aryl moiety of the aralkyl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

(xiii) a heteroaralkyl group having a heteroaryl moiety, wherein the heteroaryl moiety may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

(xiv) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), a halogen atom, and —S(O)$_n$—R (where n is 0, 1 or 2, and R is a $C_1$ to $C_4$ alkyl group that may be branched);

or may be substituted with —O—(CH$_2$)$_m$—O— (where m is 1 or 2) at positions 3 and 4 taken together; and (xv) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom; and Z is a halogen atom, and in the formula (III), R$^7$ and R$^8$ are groups independently selected from the group consisting of:

(i) a hydrogen atom;

(ii) a $C_1$ to $C_{12}$ alkyl group that may be branched or form a cyclic group;

(iii) a $C_2$ to $C_{12}$ alkenyl group that may be branched or form a cyclic group;

(iv) a $C_2$ to $C_{12}$ alkynyl group that may be branched or form a cyclic group;

(v) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

(vi) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(vii) —(CH$_2$)$_n$OCONR$^{10}$R$^{11}$ (where R$^{10}$ and R$^{11}$ are each independently a group selected from the group consisting of:
(1) a hydrogen atom;
(2) a $C_1$ to $C_4$ alkyl group that may be branched;
(3) a $C_2$ to $C_6$ alkenyl group that may be branched or form a cyclic group;
(4) a $C_2$ to $C_6$ alkynyl group that may be branched or form a cyclic group;
(5) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(6) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(7) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and
(8) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(viii) —(CH$_2$)$_n$CONR$^{12}$R$^{13}$ (where R$^{12}$ and R$^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(ix) —(CH$_2$)$_n$NR$^{12}$COR$^{13}$ (where R$^{12}$ and R$^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(x) —(CH$_2$)$_n$NR$^{12}$R$^{13}$ (where R$^{12}$ and R$^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(xi) —(CH$_2$)$_n$Y—OR$^{12}$ (where Y is a $C_1$ to $C_4$ divalent saturated hydrocarbon group that may be branched, and R$^{12}$ is a group selected from the group consisting of:
  (1) a hydrogen atom;
  (2) a $C_1$ to $C_4$ alkyl group that may be branched;
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom; and
  (4) a heteroaryl group, wherein the heteroaryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
and n is an integer from 1 to 12);

(xii) —(CH$_2$)$_n$—OR$^{12}$ (where R$^{12}$ is a group selected from the group consisting of:
  (1) a hydrogen atom;
  (2) a $C_1$ to $C_4$ alkyl group that may be branched;
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom; and
  (4) a heteroaryl group, wherein the heteroaryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
and n is an integer from 1 to 12);

(xiii) —(CH$_2$)$_n$—S—R$^{12}$ (where R$^{12}$ is a group selected from the group consisting of:
  (1) a hydrogen atom;
  (2) a $C_1$ to $C_4$ alkyl group that may be branched;
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group, —NHCOR$^9$ (where R$^9$ is a C$_1$ to C$_4$ alkyl group that may be branched), and a halogen atom; and (4) a heteroaryl group, wherein the heteroaryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom;

and n is an integer from 1 to 12);

(xiv) —(CH$_2$)$_n$—SO—R$^{12}$ (where R$^{12}$ is a group selected from the group consisting of:

(1) a hydrogen atom;

(2) a C$_1$ to C$_4$ alkyl group that may be branched;

(3) an aryl group, wherein the aryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom; and (4) a heteroaryl group, wherein the heteroaryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom;

and n is an integer from 1 to 12); and (xv) —(CH$_2$)$_n$—SO$_2$—R$^{12}$ (where R$^{12}$ is a group selected from the group consisting of:

(1) a hydrogen atom;

(2) a C$_1$ to C$_4$ alkyl group that may be branched;

(3) an aryl group, wherein the aryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom; and (4) a heteroaryl group, wherein the heteroaryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom;

and n is an integer from 1 to 12); or $R^7$ and $R^8$ are taken together to form a divalent group selected from the group consisting of: —$(CH_2)_m$— (where m is an integer from 2 to 8);

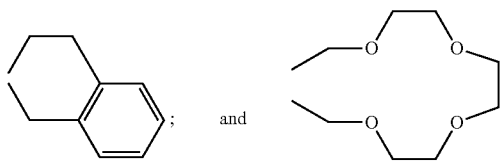

In one embodiment, $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ of the compound represented by the formula (II) are groups independently selected from the group consisting of:

(i) a hydrogen atom;

(xiv) an aryl group, wherein the aryl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
  a cyano group,
  —$NR^{20}R^{21}$ (where $R^{20}$ and $R^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —$NHCOR^9$ (where $R^9$ is a $C_1$ to $C_4$ alkyl group that may be branched),
  a halogen atom, and
  —$S(O)_n$—R (where n is 0, 1 or 2, and R is a $C_1$ to $C_4$ alkyl group that may be branched);
or may be substituted with —O—$(CH_2)_m$—O— (where m is 1 or 2) at positions 3 and 4 taken together; and (xv) a heteroaryl group, wherein the heteroaryl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
  a cyano group,
  —$NR^{20}R^{21}$ (where $R^{20}$ and $R^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —$NHCOR^9$ (where $R^9$ is a $C_1$ to $C_4$ alkyl group that may be branched), and
  a halogen atom.

In a further embodiment, $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ of the compound represented by the formula (II) are groups independently selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group.

In a further embodiment, the compound represented by the formula (II) is a compound represented by the following formula (II'):

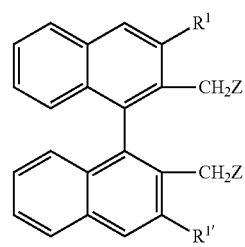

(where $R^1$ and are groups independently selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group, and $R^7$, $R^8$ and Z are groups independently as defined above).

In another embodiment, $R^7$ and $R^8$ of the secondary amine represented by the formula (II) are groups independently selected from the group consisting of:

(ii) a $C_1$ to $C_{12}$ alkyl group that may be branched or form a cyclic group; and (xii) —$(CH_2)_n$—$OR^{12}$ (where $R^{12}$ is a group selected from the group consisting of:
  (1) a hydrogen atom,
  (2) a $C_1$ to $C_4$ alkyl group that may be branched,
  (3) an aryl group, wherein the aryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom, and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom,
and n is an integer of 1 to 12.

In a further embodiment, $R^7$ and $R^8$ of the secondary amine represented by the formula (II) are groups independently selected from the group consisting of a methyl group, an ethyl group, an n-butyl group, an isobutyl group, an n-decyl group, and a cyclohexyl group.

In a still further embodiment, $R^7$ and $R^8$ of the secondary amine represented by the formula (II) are the same.

In another embodiment, $R^7$ and $R^8$ of the secondary amine represented by the formula (II) are taken together to form a divalent group selected from the group consisting of:
—$(CH_2)_m$— (where m is an integer from 2 to 8);

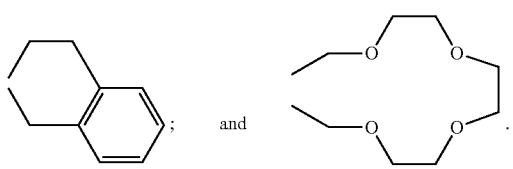

The present invention further provides a method for stereoselectively producing a compound represented by the formula (VI);

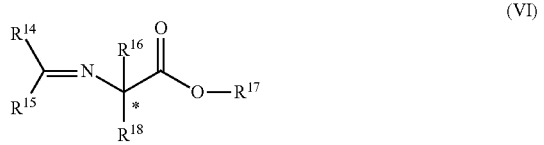

the method comprises:
alkylating a compound represented by the formula (IV)

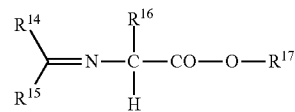

with a compound of the formula (V):

$R^{18}$—W          (V)

using a compound represented by the formula (I) that is pure with respect to axis symmetry as a phase-transfer catalyst:

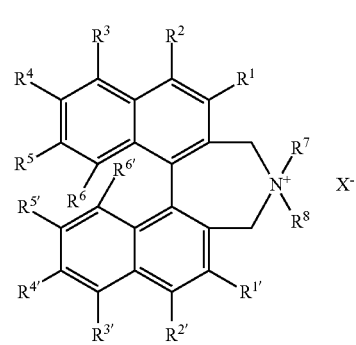

in a medium in the presence of an inorganic base,
wherein in the formula (I), $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are groups independently selected from the group consisting of:
(i) a hydrogen atom;
(ii) —$NR^{20}R^{21}$ (where $R^{20}$ and $R^{21}$ are each independently a hydrogen atom or a $C_1$ to $C_4$ alkyl group);
(iii) a cyano group;
(iv) a nitro group;
(v) a carbamoyl group;
(vi) an N—($C_1$ to $C_4$ alkyl)carbamoyl group;
(vii) an N,N-di($C_1$ to $C_4$ alkyl)carbamoyl group;
(viii) —$NHCOR^9$ (where $R^9$ is a $C_1$ to $C_4$ alkyl group that may be branched);
(ix) a $C_1$ to $C_6$ alkyl group that may be branched or form a cyclic group;
(x) a $C_2$ to $C_6$ alkenyl group that may be branched or form a cyclic group;
(xi) a $C_2$ to $C_6$ alkynyl group that may be branched or form a cyclic group;
(xii) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group), a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;

(xiii) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;

(xiv) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched),
a halogen atom, and
—S(O)$_n$—R (where n is 0, 1 or 2, and R is a $C_1$ to $C_4$ alkyl group that may be branched);
or may be substituted with —O—(CH$_2$)$_m$—O— (where m is 1 or 2) at positions 3 and 4 taken together; and (xv) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and R$^7$ and R$^8$ are each independently a monovalent organic group or are taken together to form a divalent organic group,
X— is a halide anion,
in the formulae (IV) and (VI),
R$^{14}$ and R$^{15}$ are each independently
(i) a hydrogen atom; or
(ii) an aryl group that may be substituted with a $C_1$ to $C_4$ alkyl group that may be branched, a $C_1$ to $C_5$ alkoxy group that may be branched, or a halogen atom;
with the proviso the case where both R$^{14}$ and R$^{15}$ are hydrogen atoms is excluded, R$^{16}$ is a group selected from the group consisting of:
(i) a hydrogen atom;
(ii) a $C_1$ to $C_{10}$ alkyl group that may be branched or form a cyclic group;
(iii) a $C_2$ to $C_6$ alkenyl group that may be branched or form a cyclic group;
(iv) a $C_2$ to $C_6$ alkynyl group that may be branched or form a cyclic group;
(v) an aralkyl group, wherein the aryl group of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;

(vi) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
(vii) an aryl group, wherein the aryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(viii) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
R$^{17}$ is a C$_1$ to C$_8$ alkyl group that may be branched or form a cyclic group),
in the formulae (V) and (VI),
R$^{18}$ is a group selected from the group consisting of:
(i) a C$_1$ to C$_{10}$ alkyl group that may be branched or form a cyclic group;
(ii) a C$_3$ to C$_9$ alkyl group or substituted allyl group that may be branched or form a cyclic group;
(iii) a C$_2$ to C$_6$ alkenyl group that may be branched or form a cyclic group;
(iv) a C$_2$ to C$_6$ alkynyl group that may be branched or form a cyclic group;
(v) an aralkyl group, wherein the aryl moiety of the aralkyl group may be substituted with at least one group selected from the group consisting of;
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
(vi) a heteroaralkyl group having a heteroaryl moiety, wherein the heteroaryl moiety may be substituted with at least one group selected from the group
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
(vii) an aryl group, wherein the aryl group may be substituted with at least one group selected from the group consisting of;
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(viii) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(ix) a $C_3$ to $C_9$ propargyl group or substituted propargyl group that may be branched, and
in the formula (V),
W is a functional group having a leaving ability, and
in the formula (VI),
* shows a newly produced asymmetric center.

In one embodiment, R$^7$ and R$^8$ of the compound represented by the formula (I) are groups independently selected from the group consisting of:
(i) a $C_1$ to $C_{12}$ alkyl group that may be branched or form a cyclic group and/or may be substituted with a halogen atom;
(ii) a $C_2$ to $C_{12}$ alkenyl group that may be branched or form a cyclic group and/or may be substituted with a halogen atom;
(iii) a $C_2$ to $C_{12}$ alkynyl group that may be branched or form a cyclic group and/or may be substituted with a halogen atom;
(iv) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(v) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(vi) —(CH$_2$)$_n$OCONR$^{10}$R$^{11}$ (where R$^{10}$ and R$^{11}$ are groups independently selected from the group consisting of:
(1) a hydrogen atom;
(2) a $C_1$ to $C_4$ alkyl group that may be branched;
(3) a $C_2$ to $C_6$ alkenyl group that may be branched or form a cyclic group;
(4) a $C_2$ to $C_6$ alkynyl group that may be branched or form a cyclic group;
(5) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(6) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(7) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(8) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(vii) —$(CH_2)_n CONR^{12}R^{13}$ (where $R^{12}$ and $R^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of: a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(viii) —$(CH_2)_n NR^{12}COR^{13}$ (where $R^{12}$ and $R^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(ix) —$(CH_2)_nNR^{12}R^{13}$ (where $R^{12}$ and $R^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(x) —$(CH_2)_nY$—$OR^{12}$ (where Y is a $C_1$ to $C_4$ divalent saturated hydrocarbon group that may be branched, and $R^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group, —NHCOR$^9$ (where R$^9$ is a C$_1$ to C$_4$ alkyl group that may be branched), and a halogen atom;

and n is an integer from 1 to 12);

(xi) —(CH$_2$)$_n$—OR$^{12}$ (where R$^{12}$ is a group selected from the group consisting of:

(1) a hydrogen atom;

(2) a C$_1$ to C$_4$ alkyl group that may be branched;

(3) an aryl group, wherein the aryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom; and (4) a heteroaryl group, wherein the heteroaryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom;

and n is an integer from 1 to 12);

(xii) —(CH$_2$)$_n$—S—R$^{12}$ (where R$^{12}$ is a group selected from the group consisting of:

(1) a hydrogen atom;

(2) a C$_1$ to C$_4$ alkyl group that may be branched;

(3) an aryl group, wherein the aryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom; and (4) a heteroaryl group, wherein the heteroaryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched), and a halogen atom;

and n is an integer from 1 to 12);

(xiii) —(CH$_2$)$_n$—SO—R$^{12}$ (where R$^{12}$ is a group selected from the group consisting of:

(1) a hydrogen atom;

(2) a C$_1$ to C$_4$ alkyl group that may be branched;

(3) an aryl group, wherein the aryl group may be substituted with at least one group selected from the group consisting of:

a C$_1$ to C$_4$ alkyl group that may be branched, a C$_1$ to C$_5$ alkoxy group that may be branched, an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched), a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
and n is an integer from 1 to 12); and
(xiv) —(CH$_2$)$_n$—SO$_2$—R$^{12}$ (where R$^{12}$ is a group selected from the group consisting of:
(1) a hydrogen atom;
(2) a C$_1$ to C$_4$ alkyl group that may be branched;
(3) an aryl group, wherein the aryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
and n is an integer from 1 to 12); or R$^7$ and R$^8$ are taken together to form a divalent group selected from the group consisting of: —(CH$_2$)$_m$— (where m is an integer from 2 to 8);

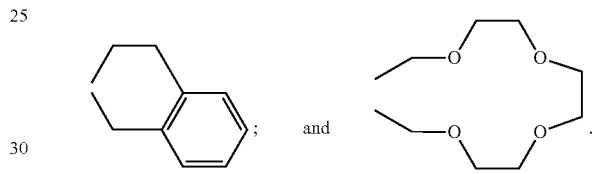

In one embodiment, R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ of the compound represented by the formula (I) are groups independently selected from the group consisting of:
(i) a hydrogen atom;
(xiv) an aryl group, wherein the aryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched),
a halogen atom, and
—S(O)$_n$—R (where n is 0, 1 or 2, and R is a C$_1$ to C$_4$ alkyl group that may be branched);
or may be substituted with —O—(CH$_2$)$_m$—O— (where m is 1 or 2) at positions 3 and 4 taken together; and
(xv) a heteroaryl group, wherein the heteroaryl group may be substituted with at least one group selected from the group consisting of:

a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom.

In a further embodiment, $R^1$, $R^{1''}$, $R^2$, $R^{2'}$, $R^3$, $R^{3'}$, $R^4$, $R^{4'}$, $R^5$, $R^{5'}$, $R^6$, and $R^{6'}$ of the compound represented by the formula (I) are groups independently selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group.

In a further embodiment, the compound represented by the formula (I) is a compound represented by the following formula (I'):

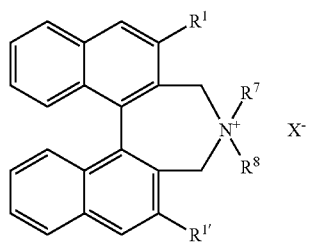

(I')

(where $R^1$ and $R^{1'}$ are groups independently selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group, and $R^7$, $R^8$ and $X^-$ are groups independently as defined above).

In another embodiment, $R^7$ and $R^8$ of the compound represented by the formula (I) are groups independently selected from the group consisting of:
(ii) a $C_1$ to $C_{12}$ alkyl group that may be branched or form a cyclic group; and
(xii) —$(CH_2)_n$—$OR^{12}$ (where $R^{12}$ is a group selected from the group consisting of:
(1) a hydrogen atom,
(2) a $C_1$ to $C_4$ alkyl group that may be branched,
(3) an aryl group, wherein the aryl group may be substituted with at least one group selected from the group consisting of:

a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom, and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom,
and n is an integer of 1 to 12.

In a further embodiment, $R^7$ and $R^8$ of the compound represented by the formula (I) are groups independently selected from the group consisting of a methyl group, an ethyl group, an n-butyl group, an isobutyl group, an n-decyl group, and a cyclohexyl group.

In a still further embodiment, $R^7$ and $R^8$ of the compound represented by the formula (I) are the same.

In another embodiment, $R^7$ and $R^9$ of the compound represented by the formula (I) are taken together to form a divalent group selected from the group consisting of:
—$(CH_2)_m$— (where m is an integer from 2 to 8);

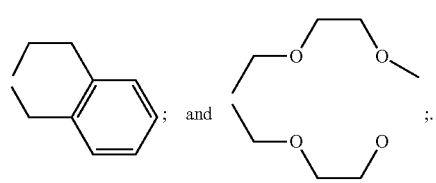

In one embodiment, the compound represented by the formula (I) is used in a ratio of 0.001 mol % to 0.1 mol % per 1 mol of the compound represented by the formula (IV).

In one embodiment, the compound represented by the formula (I) is used in a ratio of 0.005 mol % to 0.05 mol % per 1 mol of the compound represented by the formula (IV).

The present invention also provides a method for producing an optically active α-amino acid, the method comprises:

hydrolyzing an imino group ($R^{14}R^{15}C=N—$) and an ester group (—$CO_2R^{17}$) of the compound represented by the formula (VI) that is obtained by the above method, under an acidic condition:

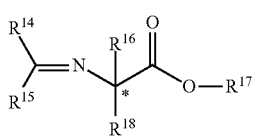

(VI)

(where $R^{14}$, $R^{15}$, $R^{16}$, $R^{17}$ and $R^{18}$ are the same groups as defined above).

The present invention also provides a method for producing an optically active α-amino acid, the method comprises:

hydrolyzing an imino group ($R^{14}R^{15}C=N—$) of the compound represented by the formula (VI) that is obtained by the above method, under an acidic condition:

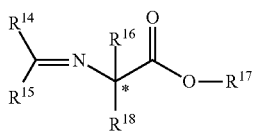

(VI)

(where $R^{14}$, $R^{15}$, $R^{16}$, $R^{17}$ and $R^{18}$ are the same groups as defined above), and hydrolyzing an ester group (—$CO_2R^{17}$) of the acid hydrolyzed product under an acidic or basic condition.

The present invention also provides a method for producing an optically active α-amino acid, the method comprises:

hydrolyzing an ester group (—$CO_2R^{17}$) of the compound represented by the formula (VI) that is obtained by the above method, under a basic condition:

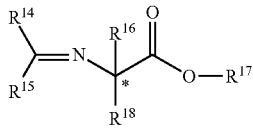

(VI)

(where $R^{14}$, $R^{15}$, $R^{16}$, $R^{17}$ and $R^{18}$ are the same groups as defined above), and hydrolyzing an imino group ($R^{14}R^{15}C=N—$) of the basic hydrolyzed product under an acidic condition.

The present invention provides a chiral phase-transfer catalyst having a more simplified structure. This phase-transfer catalyst can be produced by a fewer number of processes than conventional compounds. Thus, the phase-transfer catalyst of the present invention that can be provided more easily can be utilized for synthesizing, for example, α-alkyl-α-amino acid derivatives and α,α-dialkyl-α-amino acids.

BEST MODE FOR CARRYING OUT THE INVENTION

Hereinafter, the terms used in the present invention will be defined.

The phrase "$C_1$ to $C_n$ alkyl group that may be branched or form a cyclic group" (where n is an integer) includes any linear alkyl group having 1 to n carbon atoms, any branched alkyl group having 3 to n carbon atoms, and any cyclic alkyl group having 3 to n carbon atoms. Examples of linear alkyl groups having 1 to 6 carbon atoms include methyl, ethyl, n-propyl, n-butyl, n-pentyl, and n-hexyl. Examples of branched alkyl groups having 3 to 6 carbon atoms include isopropyl, isobutyl, tert-butyl, and isopentyl. Examples of cyclic alkyl groups having 3 to 6 carbon atoms include cyclobutyl, cyclopentyl, and cyclohexyl. Furthermore, when "$C_1$ to $C_{12}$ alkyl group that may be branched or form a cyclic group and/or may be substituted with a halogen atom" is referred to, any linear alkyl group having 1 to 12 carbon atoms, any branched alkyl group having 3 to 12 carbon atoms, and any cyclic alkyl group having 3 to 12 carbon atoms are included, and a hydrogen atom at any position of these alkyl groups may be substituted with a halogen atom. Examples of such an alkyl group include n-heptyl, isoheptyl, n-octyl, isooctyl, n-decyl, and n-dodecyl.

In N—($C_1$ to $C_4$ alkyl) carbamoyl groups and N,N-di($C_1$ to $C_4$ alkyl) carbamoyl groups, "$C_1$ to $C_4$ alkyl group" means $C_1$ to $C_4$ linear alkyl groups or $C_3$ to $C_4$ branched alkyl groups.

The phrase "$C_2$ to $C_n$ alkenyl group that may be branched or form a cyclic group" (where n is an integer) includes any linear alkenyl groups having 2 to n carbon atoms, any branched alkenyl groups having 3 to n carbon atoms, and any cyclic alkenyl groups having 3 to n carbon atoms. Examples of linear alkenyl groups having 2 to 6 carbon atoms include ethenyl, 1-propenyl, 2-propenyl, 1-butenyl, 2-butenyl, 1-pentenyl, 2-pentenyl, 3-pentenyl, 4-pentenyl, and 1-hexenyl. Examples of branched alkenyl groups having 3 to 6 carbon atoms include isopropenyl, 1-methyl-1-propenyl, 1-methyl-2-propenyl, 2-methyl-1-propenyl, 2-methyl-2-propenyl, and 1-methyl-2-butenyl. Examples of cyclic alkenyl groups having 3 to 6 carbon atoms include cyclobutenyl, cyclopentenyl, and cyclohexenyl. Furthermore, when "$C_2$ to $C_{12}$ alkenyl group that may be branched or form a cyclic group and/or may be substituted with a halogen atom" is referred to, any linear alkenyl groups having 2 to 12 carbon atoms, any branched alkenyl groups having 3 to 12 carbon atoms, and any cyclic alkenyl groups having 3 to 12 carbon atoms are included, and a hydrogen atom at any position of these alkenyl groups may be substituted with a halogen atom. Examples of such an alkenyl group include 1-heptenyl, 2-heptenyl, 1-octenyl, 1-decenyl, and 1-dodecenyl.

The phrase "$C_2$ to $C_n$ alkynyl group that may be branched or form a cyclic group" (where n is an integer) includes any linear alkynyl groups having 2 to n carbon atoms, any branched alkynyl groups having 3 to n carbon atoms, and any cyclic alkynyl groups having 3 to n carbon atoms. Examples of linear alkynyl groups having 2 to 6 carbon atoms include ethynyl, 1-propynyl, 2-propynyl, 1-butynyl, 2-butynyl, 1-pentynyl, and 1-hexynyl. Examples of branched alkynyl groups having 3 to 6 carbon atoms include 1-methyl-2-propynyl. Examples of cyclic alkynyl groups having 3 to 6 carbon atoms include cyclopropylethynyl, and cyclobutylethynyl. Furthermore, when "$C_2$ to $C_{12}$ alkynyl group that may be branched or form a cyclic group and/or may be substituted with a halogen atom" is referred to, any linear alkynyl groups having 1 to 12 carbon atoms, any branched alkynyl groups having 3 to 12 carbon atoms, and any cyclic alkynyl groups having 3 to 12 carbon atoms are included, and a hydrogen atom at any position of these alkynyl groups may be substituted with a halogen atom. Examples of such an alkynyl group include 1-heptynyl, 1-octynyl, 1-decynyl, and 1-dodecynyl.

The phrase "$C_1$ to $C_n$ alkoxy group that may be branched" (where n is an integer) includes alkoxy groups having any linear alkyl groups having 1 to n carbon atoms and alkoxy groups having any branched alkyl groups having 3 to n carbon atoms. Examples thereof include methyloxy, ethyloxy, n-propyloxy, isopropyloxy, and tert-butyloxy.

Examples of "aralkyl group" in the present invention include benzyl, phenethyl, and naphthylmethyl.

Examples of "heteroaralkyl group" in the present invention include pyridylmethyl, indolylmethyl, furylmethyl, thienylmethyl, and pyrrolylmethyl.

Examples of "aryl group" in the present invention include phenyl, naphthyl, anthryl and phenanthryl.

Examples of "heteroaryl group" in the present invention include pyridyl, pyrrolyl, imidazolyl, furyl, indolyl, thienyl, oxazolyl, benzothiophenyl-2-yl, thiazolyl, 3,4-methylenedioxyphenyl, 3,4-ethylenedioxyphenyl and tetrazolyl.

Examples of "halogen atom" in the present invention include a chlorine atom, a bromine atom, an iodine atom, and a fluorine atom. In the present invention, the term "halide anion" refers to halogen ions and examples thereof include a chloride ion, a bromide ion, an iodide ion and a fluoride ion.

The phrase "$C_3$ to $C_n$ alkyl group or substituted allyl group that may be branched or form a cyclic group" (where n is an integer) refers to allyl groups or any substituted allyl groups having a substituent(s) at position 1 and/or 2 and/or 3 and having 4 to n carbon atoms in total, and for example, includes 2-butenyl, 1-cyclopentenylmethyl, and 3-methyl-2-butenyl.

The phrase "$C_3$ to $C_n$ propargyl group or substituted propargyl group that may be branched" (where n is an integer) refers to propargyl groups or any substituted propargyl groups having a substituent(s) at position 1 and/or 3 and having 4 to n carbon atoms in total, and for example, includes 2-butynyl, and 3-trimethylsilyl-2-propynyl.

In the present invention, the term "functional group having a leaving ability" means an atom or an atom group that leaves from a substrate in a substitution reaction or an elimination reaction, that is, a leaving group, and for example, includes a halogen atom, and a sulfonyloxy group.

In the present specification, for convenience, the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom may be referred to as "group (Q)".

Hereinafter, the present invention will be described more specifically.

A quaternary ammonium salt of the present invention is pure with respect to axial asymmetry, and is a compound represented by the following formula (I):

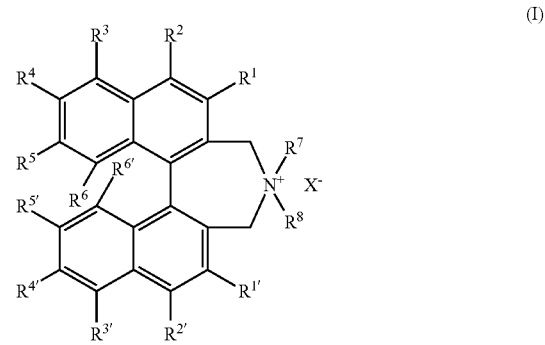

(where $R^1$, $R^{1'}$, $R^2$, $R^{2'}$, $R^3$, $R^{3'}$, $R^4$, $R^{4'}$, $R^5$, $R^{5'}$, $R^5$, and $R^{6'}$ are groups independently selected from the group consisting of:
 (i) a hydrogen atom;
 (ii) —$NR^{20}R^{21}$ (where $R^{20}$ and $R^{21}$ are each independently a hydrogen atom or a $C_1$ to $C_4$ alkyl group);
 (iii) a cyano group;
 (iv) a nitro group;
 (v) a carbamoyl group;
 (vi) an N—($C_1$ to $C_4$ alkyl)carbamoyl group;
 (vii) an N,N-di($C_1$ to $C_4$ alkyl)carbamoyl group;
 (viii) —$NHCOR^9$ (where $R^9$ is a $C_1$ to $C_4$ alkyl group that may be branched);
 (ix) a $C_1$ to $C_6$ alkyl group that may be branched or form a cyclic group;
 (x) a $C_2$ to $C_6$ alkenyl group that may be branched or form a cyclic group;
 (xi) a $C_2$ to $C_6$ alkynyl group that may be branched or form a cyclic group;
 (xii) an aralkyl group, wherein the aryl moiety of the aralkyl group may be substituted with at least one group selected from the group (Q) consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
  a cyano group,
  —$NR^{20}R^{21}$ (where $R^{20}$ and $R^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —$NHCOR^9$ (where $R^9$ is a $C_1$ to $C_4$ alkyl group that may be branched), and
  a halogen atom;
 (xiii) a heteroaralkyl group having a heteroaryl moiety, wherein the heteroaryl moiety may be substituted with at least one group selected from the group (Q);
 (xiv) an aryl group, wherein the aryl group may be substituted with at least one group selected from the group (Q) or may be substituted with —O—(CH$_2$)$_m$—O— (where m is 1 or 2) at positions 3 and 4 that are taken together; and (xv) a heteroaryl group, wherein the heteroaryl group may be substituted with at least one group selected from the group (Q);

R$^7$ and R$^8$ are each independently a monovalent organic group or taken together to form a divalent organic group, and X$^-$ is a halide anion, SCN$^-$, HSO$_4^-$ or HF$_2^-$). The compound represented by the formula (I) may have a configuration of either (S) or (R).

The compound represented by formula (I) above usefully functions as a phase-transfer catalyst for producing an optically active α-amino acid or derivative thereof, in particular, an α,α-dialkyl-α-amino acid or derivative thereof. More specifically, when the compound represented by formula (I) above is used as a phase-transfer catalyst to produce an optically active α-amino acid or derivative thereof represented by formula (VI) by alkylating a compound represented by formula (IV) with a compound represented by formula (V), the ammonium moiety constituting a cation of this compound:

contributes to the reactivity in the alkylation, and the binaphthyl moiety:

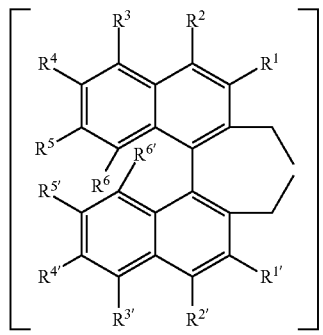

contributes to the stereoselectivity in the alkylation reaction. Therefore, in one embodiment, R$^7$ and R$^8$ in the compound represented by formula (I) are groups that can retain the reactivity and selectivity derived from the ammonium moiety and the binaphthyl moiety of the cation. (or does not inhibit the reactivity and selectivity). For example, they can be monovalent organic groups or divalent organic groups that are more inactive than the ammonium moiety and the binaphthyl moiety. In other words, R$^7$ and R$^8$ are not groups that are highly reactive themselves (or itself), but groups that do not affect the reaction in the production of the amino acid or derivative thereof that is described later. Alternatively, in the formula (I) above, R$^7$ and R$^8$ are (monovalent organic) groups independently selected from the group consisting of:

(i) a C$_1$ to C$_{12}$ alkyl group that may be branched or form a cyclic group and/or may be substituted with a halogen atom;

(ii) a C$_2$ to C$_{12}$ alkenyl group that may be branched or form a cyclic group and/or may be substituted with a halogen atom;

(iii) a C$_2$ to C$_{12}$ alkynyl group that may be branched or form a cyclic group and/or may be substituted with a halogen atom;

(iv) an aryl group, wherein the aryl group may be substituted with at least one group selected from the group (Q);

(v) a heteroaryl group, wherein the heteroaryl group may be substituted with at least one group selected from the group (Q);

(vi) —(CH$_2$)$_n$OCONR$^{10}$R$^{11}$ (where R$^{10}$ and R$^{11}$ are groups independently selected from the group consisting of:
  (1) a hydrogen atom;
  (2) a C$_1$ to C$_4$ alkyl group that may be branched;
  (3) a C$_2$ to C$_6$ alkenyl group that may be branched or form a cyclic group;
  (4) a C$_2$ to C$_6$ alkynyl group that may be branched or form a cyclic group;
  (5) an aralkyl group, wherein the aryl moiety of the aralkyl group may be substituted with at least one group selected from the group (Q);
  (6) a heteroaralkyl group having a heteroaryl moiety, wherein the heteroaryl moiety may be substituted with at least one group selected from the group (Q);
  (7) an aryl group, wherein the aryl group may be substituted with at least one group selected from the group (Q); and
  (8) a heteroaryl group, wherein the heteroaryl group may be substituted with at least one group selected from the group (Q), and n is an integer from 1 to 12);

(vii) —(CH$_2$)$_n$CONR$^{12}$R$^{13}$ (where R$^{12}$ and R$^{13}$ are groups independently selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12);

(viii) —(CH$_2$)$_n$NR$^{12}$COR$^{13}$ (where R$^{12}$ and R$^{13}$ are groups independently selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12);

(ix) —(CH$_2$)$_n$NR$^{12}$R$^{13}$ (where R$^{12}$ and R$^{13}$ are groups independently selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12);

(x) —(CH$_2$)$_n$Y—OR$^{12}$ (where Y is a C$_1$ to C$_4$ divalent saturated hydrocarbon group that may be branched, and R$^{12}$ is a group selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12);

(xi) —(CH$_2$)$_n$—OR$^{12}$ (where R$^{12}$ is a group selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12);
(xii) —(CH$_2$)$_n$—S—R$^{12}$ (where R$^{12}$ is a group selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12);
(xiii) —(CH$_2$)$_n$—SO—R$^{12}$ (where R$^{12}$ is a group selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12); and
(xiv) —(CH$_2$)$_n$—SO$_2$—R$^{12}$ (where R$^{12}$ is a group selected from the group consisting of:
  (1) a hydrogen atom;
  (2) a C$_1$ to C$_4$ alkyl group that may be branched;
  (3) an aryl group, wherein the aryl group may be substituted with at least one group selected from the group (Q); and
  (4) a heteroaryl group, wherein the heteroaryl group may be substituted with at least one group selected from the group (Q), and n is an integer from 1 to 12); or R$^7$ and R$^8$ are taken together to form a (divalent organic) group selected from the group consisting of: —(CH$_2$)$_m$— (where m is an integer from 2 to 8);

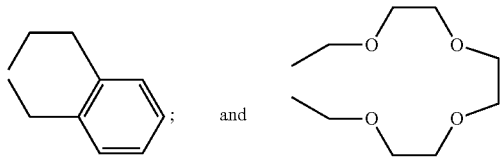

In the present invention, in the formula (I) above, R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are preferably groups independently selected from the group consisting of:
  (i) a hydrogen atom;
  (xiv) an aryl group, wherein the aryl group may be substituted with at least one group selected from the group consisting of:
    a C$_1$ to C$_4$ alkyl group that may be branched,
    a C$_1$ to C$_5$ alkoxy group that may be branched,
    an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
    a cyano group,
    —NR$^{20}$R$^{21}$ (where R$^{20}$ and R$^{21}$ are each independently a hydrogen atom or a C$_1$ to C$_4$ alkyl group),
    a nitro group,
    a carbamoyl group,
    an N—(C$_1$ to C$_4$ alkyl)carbamoyl group,
    an N,N-di(C$_1$ to C$_4$ alkyl)carbamoyl group,
    —NHCOR$^9$ (where R$^9$ is a C$_1$ to C$_4$ alkyl group that may be branched),
    a halogen atom, and
    —S(O)$_n$—R (where n is 0, 1 or 2, and R is a C$_1$ to C$_4$ alkyl group that may be branched);
  or may be substituted with —O—(CH$_2$)$_m$—O— (where m is 1 or 2) at positions 3 and 4 taken together; and
  (xv) a heteroaryl group, wherein the heteroaryl group may be substituted with at least one group selected from the group consisting of:
    a C$_1$ to C$_4$ alkyl group that may be branched,
    a C$_1$ to C$_5$ alkoxy group that may be branched,
    an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
    a cyano group,
    —NR$^{20}$R$^{21}$ (where R$^{20}$ and R$^{21}$ are each independently a hydrogen atom or a C$_1$ to C$_4$ alkyl group),
    a nitro group,
    a carbamoyl group,
    an N—(C$_1$ to C$_4$ alkyl)carbamoyl group,
    an N,N-di(C$_1$ to C$_4$ alkyl)carbamoyl group,
    —NHCOR$^9$ (where R$^9$ is a C$_1$ to C$_4$ alkyl group that may be branched), and
    a halogen atom, more preferably, they are selected from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group. In particular, of the compounds represented by the formula (I) above, a compound represented by the following formula (I') is preferable:

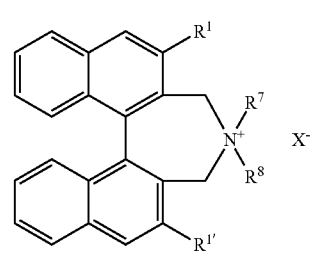

(I')

(where, R$^1$ and R$^{1'}$ are groups selected independently from the group consisting of a hydrogen atom, a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, and a 2,3-bis(trifluoromethyl)phenyl group, and $R^7$, $R^8$ and $X^-$ are each independently the above-defined groups).

Furthermore, preferably, $R^7$ and $R^8$ of the compound represented by the formula (I) above are groups independently selected from the group consisting of:

(ii) a $C_1$ to $C_{12}$ alkyl group that may be branched or form a cyclic group; and (xii) —$(CH_2)_n$—$OR^{12}$ (where $R^{12}$ is a group selected from the group consisting of:
(1) a hydrogen atom,
(2) a $C_1$ to $C_4$ alkyl group that may be branched,
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom, and (4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom, and n is an integer of 1 to 12, more preferably, they are selected from the group consisting of a methyl group, an ethyl group, an n-butyl group, an isobutyl group, an n-decyl group, and a cyclohexyl group. Furthermore, $R^7$ and $R^8$ are preferably the same, or a compound in which $R^7$ and $R^8$ are taken together to form a divalent group selected from the group consisting of: —$(CH_2)_m$— (where m is an integer from 2 to 8);

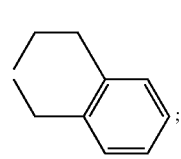 ; and 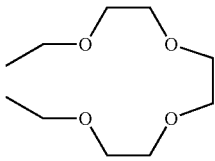 .

The quaternary ammonium salt represented by the formula (I) can be produced by reacting a compound represented by the following formula (II):

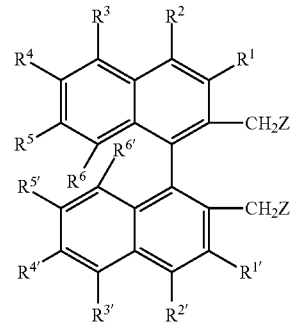

(II)

(where $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are the same as defined in the formula (I), and Z is a halogen atom) with a secondary amine represented by the following formula (III):

(III)

(where $R^7$ and $R^8$ are the same as defined in the formula (I)) in an organic solvent in the presence of an acid scavenging agent.

The compound of the formula (II) can be prepared easily from, for example, easily available 1,1'-binaphthyl-2,2'-dicarboxylic acid (see Seki, M. et al., Synthesis, 2000, p. 1677) in a known process as described in the following Scheme 1 (see Ooi, T. et al., J. Org. Chem., vol. 68, p. 4577, 2003). The 1,1'-binaphthyl-2,2'-dicarboxylic acid may be either the (S)-form or (R)-form.

Scheme 1

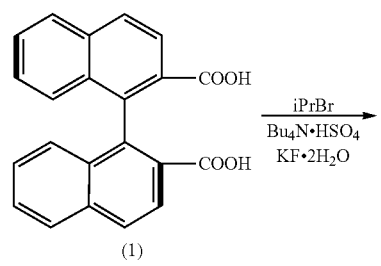

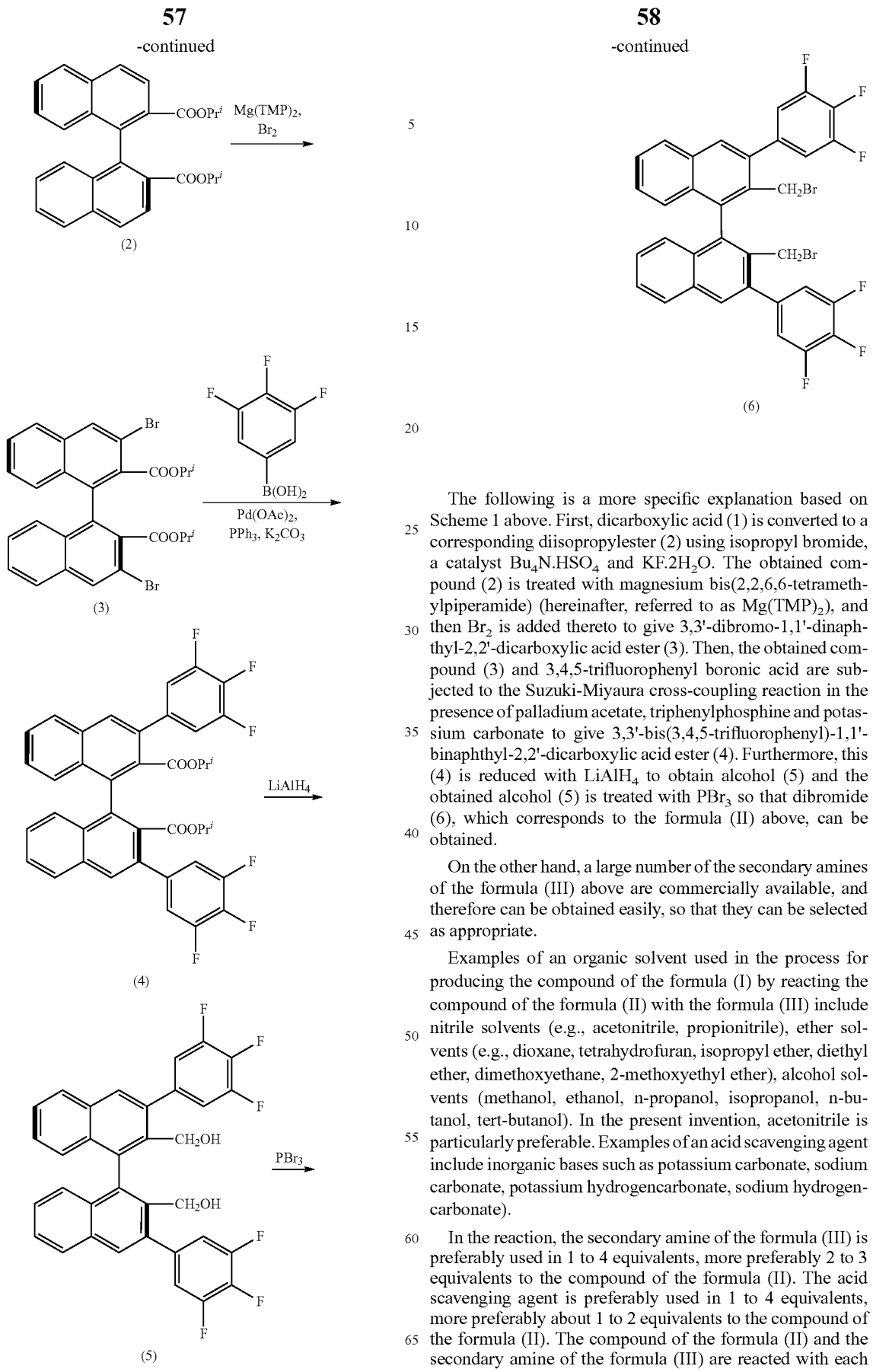

The following is a more specific explanation based on Scheme 1 above. First, dicarboxylic acid (1) is converted to a corresponding diisopropylester (2) using isopropyl bromide, a catalyst $Bu_4N\cdot HSO_4$ and $KF\cdot 2H_2O$. The obtained compound (2) is treated with magnesium bis(2,2,6,6-tetramethylpiperamide) (hereinafter, referred to as $Mg(TMP)_2$), and then $Br_2$ is added thereto to give 3,3'-dibromo-1,1'-dinaphthyl-2,2'-dicarboxylic acid ester (3). Then, the obtained compound (3) and 3,4,5-trifluorophenyl boronic acid are subjected to the Suzuki-Miyaura cross-coupling reaction in the presence of palladium acetate, triphenylphosphine and potassium carbonate to give 3,3'-bis(3,4,5-trifluorophenyl)-1,1'-binaphthyl-2,2'-dicarboxylic acid ester (4). Furthermore, this (4) is reduced with $LiAlH_4$ to obtain alcohol (5) and the obtained alcohol (5) is treated with $PBr_3$ so that dibromide (6), which corresponds to the formula (II) above, can be obtained.

On the other hand, a large number of the secondary amines of the formula (III) above are commercially available, and therefore can be obtained easily, so that they can be selected as appropriate.

Examples of an organic solvent used in the process for producing the compound of the formula (I) by reacting the compound of the formula (II) with the formula (III) include nitrile solvents (e.g., acetonitrile, propionitrile), ether solvents (e.g., dioxane, tetrahydrofuran, isopropyl ether, diethyl ether, dimethoxyethane, 2-methoxyethyl ether), alcohol solvents (methanol, ethanol, n-propanol, isopropanol, n-butanol, tert-butanol). In the present invention, acetonitrile is particularly preferable. Examples of an acid scavenging agent include inorganic bases such as potassium carbonate, sodium carbonate, potassium hydrogencarbonate, sodium hydrogencarbonate).

In the reaction, the secondary amine of the formula (III) is preferably used in 1 to 4 equivalents, more preferably 2 to 3 equivalents to the compound of the formula (II). The acid scavenging agent is preferably used in 1 to 4 equivalents, more preferably about 1 to 2 equivalents to the compound of the formula (II). The compound of the formula (II) and the secondary amine of the formula (III) are reacted with each other in the presence of the acid scavenging agent in an appropriate organic solvent with stirring. The reaction temperature is preferably from room temperature to the boiling point of the organic solvent, and more preferably the reaction is performed under heating reflux. The reaction time is preferably 30 minutes to 24 hours, more preferably 6 to 12 hours. In this case, the organic solvent is preferably used 5 to 50 times, more preferably 5 to 30 times the amount of the compound of the formula (II) in the ratio of volume (mL)/weight (g). After the reaction is finished, the reaction mixture is extracted with dichloromethane, dichloroethane, or carbon tetrachloride, and isolated and purified by silica gel column chromatography, so that the compound of the formula (I) can be obtained. Alternatively, the reaction mixture may be used, as it is, as a phase-transfer catalyst in the method for producing α-amino acid derivatives, which will be more specifically described later.

Thus obtained compound of the formula (I) in which $X^-$ is a halide anion has a pure form with respect to axial asymmetry, and can be used as a phase-transfer catalyst. Here, "pure with respect to axial asymmetry" means that among the stereoisomers based on axial asymmetry, the rate of the presence of one specific isomer is higher than that of other isomers. Preferably, the rate of the presence of the one specific isomer is 90% or more, more preferably 95% or more, and even more preferably 98% or more.

Furthermore, the compound of the formula (I) in which $X^-$ is a halide anion can be made into a compound in which the halide anion is converted to $SCN^-$, $HSO_4^-$ or $HF_2^-$, for example, through the following process.

First, a method for producing the compound of the formula (I) in which $X^-$ is $SCN^-$ or $HSO_4^-$ will be described.

The compound of the formula (I) obtained in the above-described manner in which $X^-$ is a halide anion is dissolved in, for example, a suitable second organic solvent according to the method described in Japanese Laid-Open Patent Publication No. 2002-173492 and mixed with a saturated aqueous solution of an alkali metal salt of thiocyanic acid so that the halide anion of $X^-$ is converted to $SCN^-$.

Examples of the second organic solvent that can be used for this exchange include dichloromethane, chloroform, dichloroethane, tetrahydrofuran, methyl t-butyl ether, diisopropyl ether, and ethyl acetate. Examples of the alkali metal salt of thiocyanic acid include potassium thiocyanate and sodium thiocyanate.

For example, by mixing the compound of the formula (I) in which $X^-$ is a halide anion with an alkali metal salt of thiocyanic acid in a solution under a relatively mild condition such as under room temperature so as to come into contact, the reaction thereof can proceed easily, and the reaction product (e.g., the compound of the formula (I) in which $X^-$ is $SCN^-$) can be obtained in a quantitative yield.

Furthermore, by reacting the compound of the formula (I) in which $X^-$ is $SCN^-$ with a concentrated nitric acid solution, $X^-$ can be converted easily from $SCN^-$ to $HSO_4^-$.

By further reacting thus obtained compound of the formula (I) in which $X^-$ is $HSO_4^-$ with an alkali metal fluoride (e.g., potassium fluoride, sodium fluoride or lithium fluoride), a compound represented by the formula (Ia):

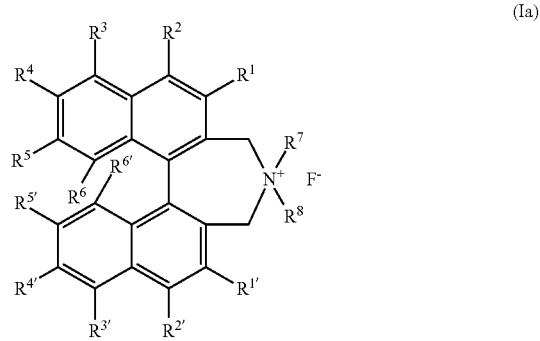

(where $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are the same as defined in the formula (I)) can be obtained, which can be used as a catalyst, for example, in a reaction of a silyl enol ether and a carbonyl compound (aldol reaction).

Examples of silyl enol ether used in the aldol reaction include a trialkylsilyl enol ether. A trialkylsilyl enol ether can be prepared in advance by reacting a chlorosilane such as trimethylsilyl chloride and triethylsilyl chloride with a carbonyl compound (e.g., ketone derivatives such as 2-butanone, 4-penten-2-one, diethyl ketone, acetophenone, propiophenone, butyronaphtone, cyclohexanone, 1-oxoindan, 1-tetralone or 2-tetralone) in the presence of a base.

In addition to the carbonyl compound (the above-described ketone derivatives), which is a precursor of a silyl enol ether, examples of the carbonyl compound that can be reacted with a silyl enol ether used in the aldol reaction, include aldehyde compounds such as acetylaldehyde, propionaldehyde, butylaldehyde, isobutylaldehyde, isovaleraldehyde, capronaldehyde, dodecylaldehyde, palmitinaldehyde, stearinaldehyde, acrolein, crotonaldehyde, cyclohexanecarbaldehyde, benzaldehyde, anisaldehyde, nicotinaldehyde, cinnamaldehyde, α-naphthaldehyde, and β-naphthaldehyde.

With respect to such a silyl enol ether and such a carbonyl compound, the compound represented by the formula (Ia) is used as a catalyst in the aldol reaction so that the stereoselectivity in the reaction can be controlled.

Next, a method for producing the compound of the formula (I) in which $X^-$ is $HF_2^-$ will be described.

The compound of the formula (I) obtained in the above-described manner in which $X^-$ is a halide anion is first brought in contact with an ion-exchange resin so that a first intermediate is produced.

As the ion-exchange resin, any ion-exchange resin can be selected by those skilled in the art. Specific examples of the ion-exchange resin that can be used include Amberlyst A26 (OH) (manufactured by ORGANO CORPORATION).

The compound of the formula (I) in which $X^-$ is a halide anion can be brought in contact with an ion-exchange resin by dissolving the compound of the formula (I) in which $X^-$ is a halide anion in a suitable third solvent and passing this solution through a column filled with the ion-exchange resin. As the third solvent that can be used for such a contact, alcohol solvents are preferable. Specific examples of alcohol solvents include methyl alcohol, ethyl alcohol, isopropyl alcohol, and normal propyl alcohol, although not limited thereto.

There is no limitation regarding the amounts of the compound of the formula (I) in which $X^-$ is a halide anion and the third solvent that are used in this contact, and they can be set as appropriate by the those skilled in the art.

Thus, the first intermediate is produced.

Then, the obtained first intermediate is neutralized with a hydrogen fluoride aqueous solution preferably without removing the solvent.

There is no limitation regarding the amount of the hydrogen fluoride aqueous solution used in the present invention. In view of increasing the productivity, preferably, the amount is selected so that hydrogen fluoride is reacted in an amount at least equivalent to that of the compound of the formula (I) in which $X^-$ is a halide anion. Thus, the first intermediate is neutralized, and a compound represented by the formula (Ib):

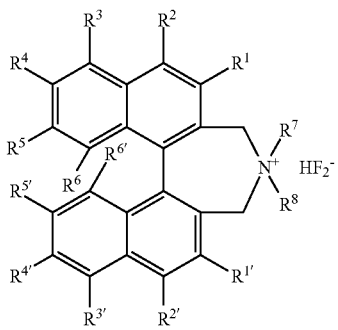

(Ib)

in which $X^-$ is further converted from the halide anion to $HF_2^-$ can be precipitated in the solution.

Thereafter, the compound of this formula (Ib) can be easily isolated by removing the solvent using means usually used by those skilled in the art.

Thus obtained compound of the formula (Ib) can be utilized as a catalyst for producing a nitroalcohol that is diastereoselectively and enantioselectively controlled.

Next, a method for producing α-amino acid derivatives using the quaternary ammonium compound of the present invention represented by the formula (I) as a phase-transfer catalyst will be described.

An α-amino acid derivative represented by the following formula (VI) can be produced stereoselectively by a process for alkylating a compound represented by the following formula (IV) with a compound of a formula (V), using the compound represented by the formula (I) as a phase-transfer in a medium in the presence of an inorganic base:

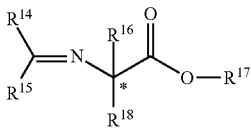

(VI)

(where $R^{14}$ and $R^{15}$ are each independently
(i) a hydrogen atom; or
(ii) an aryl group that may be substituted with a $C_1$ to $C_4$ alkyl group that may be branched, a $C_1$ to $C_5$ alkoxy group that may be branched, or a halogen atom; with the proviso that the case where both $R^{14}$ and $R^{15}$ are hydrogen atoms is excluded, $R^{16}$ is a group selected from the group consisting of:
(i) a hydrogen atom;
(ii) a $C_1$ to $C_{10}$ alkyl group that may be branched or form a cyclic group;

(iii) a $C_2$ to $C_6$ alkenyl group that may be branched or form a cyclic group;
(iv) a $C_2$ to $C_6$ alkynyl group that may be branched or form a cyclic group;
(v) an aralkyl group, wherein the aryl moiety of the aralkyl group may be substituted with at least one group selected from the group (Q) consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, $-NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or $-NHCOR^9$ (where $R^9$ is a $C_1$ to $C_4$ alkyl group that may be branched),
    a cyano group,
    $-NR^{20}R^{21}$ (where $R^{20}$ and $R^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    $-NHCOR^9$ (where $R^9$ is a $C_1$ to $C_4$ alkyl group that may be branched), and
    a halogen atom;
(vi) a heteroaralkyl group having a heteroaryl moiety, wherein the heteroaryl moiety may be substituted with at least one group selected from the group (Q);
(vii) an aryl group, wherein the aryl group may be substituted with at least one group selected from the group (Q); and
(viii) a heteroaryl group, wherein the heteroaryl group may be substituted with at least one group selected from the group (Q);

$R^{17}$ is a $C_1$ to $C_8$ alkyl group that may be branched or form a cyclic group;

$R^{18}$ is a group selected from the group consisting of:
(i) a $C_1$ to $C_{10}$ alkyl group that may be branched or form a cyclic group;
(ii) a $C_3$ to $C_9$ alkyl group or substituted allyl group that may be branched or form a cyclic group;
(iii) a $C_2$ to $C_6$ alkenyl group that may be branched or form a cyclic group;
(iv) a $C_2$ to $C_6$ alkynyl group that may be branched or form a cyclic group;
(v) an aralkyl group, wherein the aryl moiety of the aralkyl group may be substituted with at least one group selected from the group (Q);
(vi) a heteroaralkyl group having a heteroaryl moiety, wherein the heteroaryl moiety may be substituted with at least one group selected from the group (Q);
(vii) an aryl group, wherein the aryl group may be substituted with at least one group selected from the group (Q);
(viii) a heteroaryl group, wherein the heteroaryl group may be substituted with at least one group selected from the group (Q); and (ix) a $C_3$ to $C_9$ propargyl group or substituted propargyl group that may be branched; and

* shows a newly generated asymmetric center;

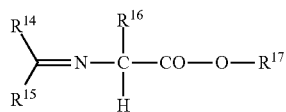
(IV)

(where $R^{14}$, $R^{15}$, $R^{16}$ and $R^{17}$ are the same as defined in the formula (VI)); and $$R^{18}—W \quad (V)$$

(where $R^{18}$ is the same as defined in the formula (VI), and W is a functional group having a leaving ability).

Examples of the medium used in this process include benzene, toluene, xylene, ethyl ether, isopropyl ether, tetrahydrofuran, and dioxane. Alternatively, the medium may be a two-phase medium containing water and a medium of these which is immiscible with water. The medium may be used in a volume (mL)/weight (g) ratio of a factor, preferably of 5 to 30, more preferably 8 to 25 to the compound of the formula (IV).

Examples of the inorganic base used in this process include lithium hydroxide, sodium hydroxide, potassium hydroxide, calcium hydroxide, rubidium hydroxide, and cesium hydroxide. The inorganic base may be used preferably in 2 to 10 equivalents, more preferably 3 to 7 equivalents to the compound of the formula (IV). The inorganic base may be used in the form of a 10 to 60 w/v % alkali aqueous solution, and the volume in this case may be preferably a factor of 4 to 20, more preferably 8 to 15 in volume (mL)/weight (g) ratio to the compound of the formula (IV).

In the alkylation process, the compound of the formula (V) is used preferably in 1 to 1.5 equivalents, more preferably 1.1 to 1.3 equivalents, and even more preferably 1.2 to 1.25 equivalents to the compound of the formula (IV). The compound of the formula (I) is used, as a phase-transfer catalyst, preferably in 0.001 mol % to 0.1 mol %, more preferably 0.005 mol % to 0.05 mol % to 1 mol of the compound of the formula (IV). Thus, the phase-transfer catalyst used in the present invention has a high activity, and therefore by using the catalyst at only a small amount to 1 mole of the compound of the formula (IV), a desired optically active α-amino acid and derivatives thereof can be produced.

In the present invention, in addition to such a phase-transfer catalyst, achiral quaternary ammonium salts such as tetrabutyl ammonium bromide (TBAB) may be also used in the reaction system simultaneously. For example, TBAB functions as a cocatalyst in the reaction system in the present invention to improve the yield of an α-amino acid and its derivatives obtained, and also can further reduce the amount of the phase-transfer catalyst represented by the formula (I) used in the present invention. The amount of TBAB that can be used in the present invention is preferably 0.005 mol % to 0.1 mol %, and more preferably 0.01 to 0.06 mol % to 1 mol of the compound of the formula (IV).

The alkylation process is performed at a suitable temperature between −30° C. to room temperature, preferably −20° C. to 0° C., in air, preferably in an argon atmosphere. This process is performed with stirring over a suitable period until an alkylation reaction proceeds to a sufficient extent. The reaction time is preferably 30 min to 48 hours, more preferably 1 hour to 24 hours.

According to the method of the present invention using the compound of the formula (I) of the present invention as described above, an optically active compound of the formula (VI) can be obtained in a high yield and high optical purity. Here, "high optical purity" refers to at least 80% ee, preferably at least 85% ee, more preferably 90% ee, and even more preferably at least 95% ee.

In another aspect of the present invention, a method for producing an optically active α-amino acid is provided.

In the present invention, an optically active α-amino acid can be produced by performing, for example, either one of the following procedures, using the optically active compound of the formula (VI) (optically active α-amino acid derivative) that is obtained by the above-described method.

In a first method, the imino group ($R^{14}R^{15}C$=N—) moiety of the optically active compound of the formula (VI) (optically active α-amino acid derivative) that is obtained by the above-described method is hydrolyzed under an acidic condition (imine acidic hydrolysis process). Examples of the acid used in the imine acidic hydrolysis process include inorganic acids (e.g., hydrochloric acid or phosphoric acid) and organic acids containing tribasic acid (e.g., acetic acid, citric acid). More specifically, the imine acidic hydrolysis process proceeds by treating the compound of the formula (VI) in a suitable medium (e.g., tetrahydrofuran or toluene) at a suitable temperature (e.g., room temperature) using an aqueous solution of the acid as described above. As a result, an ester derivative of amino acid in which the terminal amino group is liberated can be obtained as an acidic hydrolysis product.

Then, the ester derivative of amino acid (acidic hydrolysis product) obtained by the above-described process is subjected to a hydrolysis reaction, if necessary, under acidic conditions stronger than the imine acidic hydrolysis or under basic conditions. Thus, a desired amino acid in which the terminal of the acidic hydrolysis product (i.e., an ester group (—$CO_2R^{17}$) in the acidic hydrolysis product) becomes carboxylic acid can be obtained.

Alternatively, in a second method, the process opposite to the method described above is adopted. That is to say, the ester group (—$CO_2R^{17}$) in the optically active compound of the formula (VI) (optically active α-amino acid derivative) obtained in the above-described alkylation reaction is first hydrolyzed under basic conditions (ester basic hydrolysis process). In this ester basic hydrolysis process, an alkali aqueous solution such as sodium hydroxide aqueous solution can be used. By such hydrolysis, a basic hydrolysis product in which the terminal of the compound of the formula (VI) (i.e., an ester group (—$CO_2R^{17}$) in the compound of the formula (VI)) becomes carboxylic acid can be obtained.

Then, the imino group ($R^{14}R^{15}C$=N—) moiety of the above-obtained basic hydrolysis product is hydrolyzed under an acidic condition (imine acidic hydrolysis process). Examples of the acid used in the imine acidic hydrolysis process include inorganic acids (e.g., hydrochloric acid, phosphoric acid, sulfuric acid) and organic acids including tribasic acid (e.g., acetic acid, citric acid). More specifically, the imine acidic hydrolysis process proceeds by treating the basis hydrolysis product in a suitable medium (e.g., tetrahydrofuran or toluene) at a suitable temperature (e.g., room temperature) using an aqueous solution of the acid as described above. As a result, a desired amino acid in which the terminal amino acid is liberated can be obtained.

In the present invention, in the case where an amino acid is produced from the compound of the formula (VI), either the first method or the second method may be used, and either can be selected arbitrarily by those skilled in the art, according to the specific structure of the amino acid to be actually produced and other production conditions.

In this manner, a desired optically active α-amino acid can be produced efficiently and optionally without limitations on its structure.

EXAMPLES

Hereinafter, the present invention will be more specifically described by way of examples, but is not limited thereby.

In the following examples, $^1$H NMR spectrum was measured on a JEOL JNM-FX400 (400 MHz) spectrometer and a JMTC-400/54/SS (400 MHz) spectrometer. The optical purity of a reaction product was measured by high-performance liquid chromatography (HPLC) with an apparatus Shimadzu 10 using 4.6 mm×25 cm Daicel Chiralcel OD, OD-H, AD or AD-H. The reaction progress was monitored with a Merck precoated TLC plate (silica gel 60 GF254, 0.25 mm) for thin film chromatography (TLC).

Reference Example 1

Synthesis of Starting Material (Compound 6) for Synthesizing Quaternary Ammonium Salt

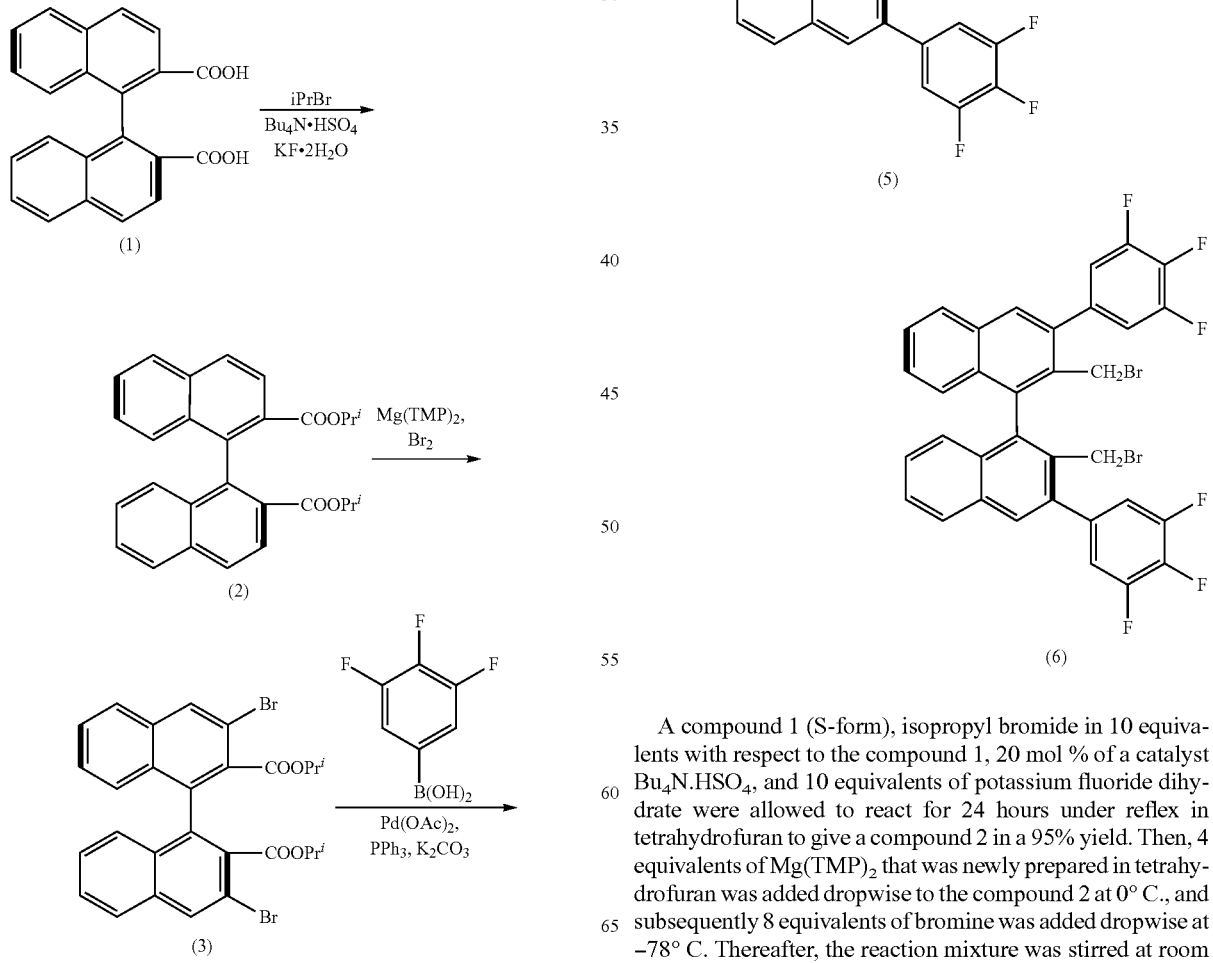

A compound 1 (S-form), isopropyl bromide in 10 equivalents with respect to the compound 1, 20 mol % of a catalyst $Bu_4N.HSO_4$, and 10 equivalents of potassium fluoride dihydrate were allowed to react for 24 hours under reflux in tetrahydrofuran to give a compound 2 in a 95% yield. Then, 4 equivalents of $Mg(TMP)_2$ that was newly prepared in tetrahydrofuran was added dropwise to the compound 2 at 0° C., and subsequently 8 equivalents of bromine was added dropwise at −78° C. Thereafter, the reaction mixture was stirred at room temperature for one hour to give a compound 3 in a 91% yield.

The compound 3 and 2.4 equivalents of 3,4,5-trifluorophenyl boronic acid were subjected to the Suzuki-Miyaura cross-coupling reaction in the presence of 5 mol % of palladium acetate, 15 mol % of PPh$_3$ and 3 equivalents of potassium carbonate in dimethylformamide at 90° C. for 8 hours to give a compound 4 in a 94% yield. Then, the compound 4 was reduced with 3 equivalents of LiAlH$_4$ in tetrahydrofuran at 0° C. to room temperature. Then, the obtained compound 5 was stirred with 0.5 equivalents of PBr$_3$ in tetrahydrofuran at 0° C. for one hour to give a compound 6 (S-form) in a 90% yield. The R-form was prepared in the same manner.

Example 1

Synthesis of Quaternary Ammonium Salt (Compound 7)

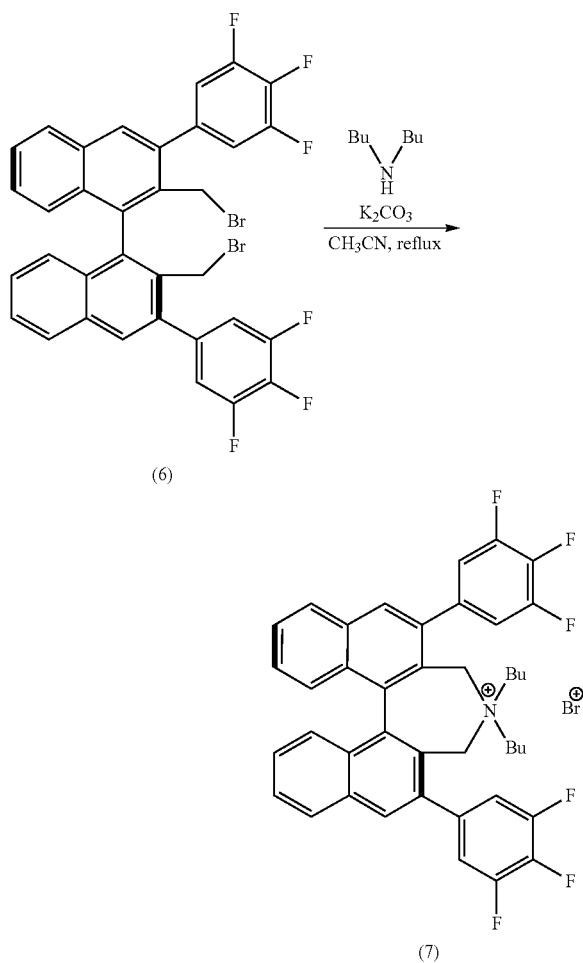

A mixture of the compound 6 (S-form) (280 mg, 0.4 mmol), dibutylamine (140 µL, 0.8 mmol), and potassium carbonate (82 mg, 0.6 mmol) in acetonitrile (5 mL) was heated and refluxed for 10 hours with stirring. The mixture was poured into water and extracted with dichloromethane. The organic layer extract was dried over sodium sulfate, and concentrated. The residue was purified by silica gel column chromatography (eluent: methanol/dichloromethane=1:20) for purification to give a compound 7 (S-form) (247 mg, 0.33 mmol) in a 83% yield.

The NMR spectrum of the obtained compound 7 (S-form) was as follows: $^1$H NMR (400 MHz, CDCl$_3$) δ 7.97-7.95 (4H, m, Ar—H), 7.55-7.51 (2H, m, Ar—H), 7.27-7.23 (8H m, Ar—H), 4.99 (2H, d, J=14.2 Hz, Ar—CH$_2$), 3.74 (2H, d, J=13.9 Hz, Ar—CH$_2$), 3.32 (2H, t, J=12.5 Hz, N—CH$_2$—CH$_2$), 2.56 (2H, t, J=12.31 Hz, N—CH$_2$—CH$_2$), 1.06-0.97 (6H, m, CH$_2$), 0.71 (6H, t, J=6.9 Hz, CH$_3$), 0.23 (2H, bs, CH$_2$); $^{13}$C NMR (100 MHz, CDCl$_3$) δ 150.95 (d, J$_{C-F}$=253 Hz), 139.61 (ddd, J$_{C-F}$=253, 15, 15 Hz), 138.31, 136.86, 134.64 (d, J$_{C-F}$=4 Hz), 133.44, 131.13, 130.85, 128.31, 128.28, 127.66, 127.37, 123.34, 115.31-113.76 (m), 57.58, 57.37, 24.60, 19.32, 13.24.

For the R-form of the compound 6, the same procedure was performed to give the compound 7 (R-form).

Example 2

Confirmation of α-Benzylation Of Alanine

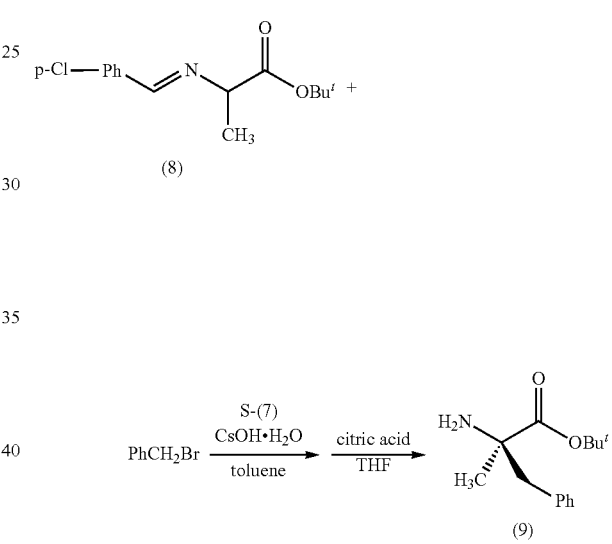

To a mixture of alanine (t)-butyl ester-p-chlorobenzyl Schiff base (compound 8) (134 mg, 0.5 mmol), 1 mol % of the compound 7 (S-form), and benzyl bromide (1.2 equivalents) in 2 mL of toluene, cesium hydroxide.monohydrate (5 equivalents) was added at 0° C., and stirred under an argon atmosphere at 0° C. for 3 hours. The reaction mixture was poured into water and extracted with dichloromethane, and the solvent was removed, and then the residue was dissolved in 5 mL of tetrahydrofuran. Then, 5 mL of 0.5 M citric acid aqueous solution was added thereto and the mixture was stirred at room temperature for one hour. The aqueous layer was washed with ether and alkalized with sodium hydrogencarbonate, and then was extracted with dichloromethane. The organic layer was dried over sodium sulfate and concentrated to give an oily product. The obtained oily product was subjected to silica gel column chromatography (eluent: ethyl acetate/hexane=2/1) to give a benzylated product of alanine (compound 9) in 97% ee and a 82% yield. The optical purity of the obtained product was analyzed by HPLC [Daicel Chiralcel AD; eluent: hexane/isopropanol=30:1, 0.5 mL/min; retention time: (R)-form=12.9 min, (S)-form=20.5 min].

When the process under an argon atmosphere was performed at −20° C., a compound 9 having substantially complete enantioselectivity (99% ee) was obtained in a 85% yield.

Example 3

Synthesis of Quaternary Ammonium Salt
(Compound 10)

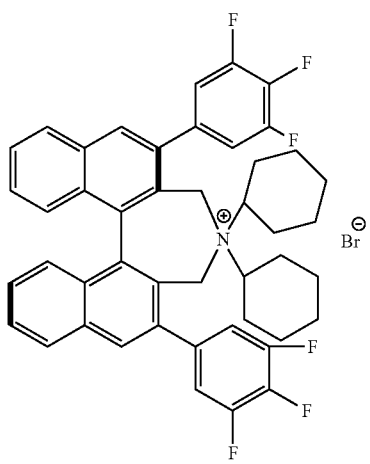

(10)

The same procedure as in Example 1 was performed except that the R-form of the compound 6 (140 mg, 0.2 mmol) was used and dicyclohexylamine was used instead of dibutylamine. The product was purified by silica gel column chromatography to give a compound 10 (R-form) (96 mg, 0.12 mmol) in a 60% yield.

The NMR spectrum of the obtained compound was as follows: $^1$H NMR (400 MHz, CDCl$_3$) δ 8.05 (4H, bs, Ar—H), 7.65 (2H, t, J=7.7 Hz, Ar—H), 7.49 (4H, bs, Ar—H), 7.38 (2H, t, J=7.5 Hz, Ar—H), 7.27-7.24 (2H, m, Ar—H), 5.15 (2H, d, J=13.9 Hz, Ar—CH$_2$), 4.20 (2H, d, J=13.5 Hz, Ar—CH$_2$), 3.18 (2H, bs, CH$_2$), 3.05 (1H, bs, N—CH), 2.34 (2H, d, J=9.9 Hz, CH$_2$), 2.16 (2H, d, J=8.7 Hz, CH$_2$), 1.82-0.88 (15H, m, CH and CH$_2$); $^{13}$C NMR (100 MHz, CDCl$_3$) δ 151.08 (d, J$_{C-F}$=249 Hz), 139.56 (d, J$_{C-F}$=254 Hz), 138.43, 136.76, 134.80 (d, J$_{C-F}$=3.3 Hz), 133.34, 131.61, 131.05, 128.33, 127.78, 127.44, 123.58, 115.05-114.82 (m), 73.95, 54.89, 53.37, 52.99, 30.36, 28.69, 28.39, 26.62, 26.45, 24.88, 24.76.

Example 4

Synthesis of Quaternary Ammonium Salt
(Compound 11)

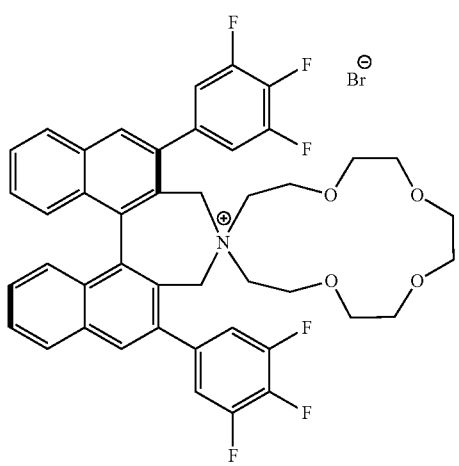

(11)

The same procedure as in Example 1 was performed except that the R-form of the compound 6 (140 mg, 0.2 mmol) was used and 1-aza-4,7,10,13-tetraoxacyclopentadecane was used instead of dibutylamine. The product was purified by silica gel column chromatography to give a compound 11 (59 mg, 0.07 mmol) in a 35% yield.

The NMR spectrum of the obtained compound was as follows: $^1$H NMR (400 MHz, CDCl$_3$) δ 8.05-8.03 (4H, m, Ar—H), 7.68-7.64 (2H, m, Ar—H), 7.43-7.35 (4H, m, Ar—H), 7.26-7.16 (4H, m, Ar—H), 4.89 (2H, d, J=13.9 Hz, Ar—CH$_2$), 4.08 (2H, bs), 4.03 (2H, d, J=13.5 Hz, Ar—CH$_2$), 3.77-3.74 (2H, m, CH$_2$), 3.58-3.54 (2H, m, CH$_2$), 3.50-3.45 (10H, m, CH$_2$), 3.38-3.35 (2H, m, CH$_2$), 3.07-3.03 (2H, m, CH$_2$).

Example 5

Synthesis of Quaternary Ammonium Salt
(Compound 12)

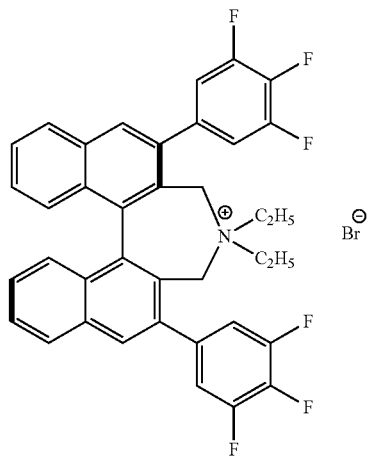

(12)

The same procedure as in Example 1 was performed except that the R-form of the compound 6 (140 mg, 0.2 mmol) was used and diethylamine was used instead of dibutylamine. The product was purified by silica gel column chromatography to give a compound 12 (R-form) (120 mg, 0.17 mmol) in a 87% yield.

The NMR spectrum of the obtained compound was as follows: $^1$H NMR (400 MHz, CDCl$_3$) δ 8.02 (4H, bs, Ar—H), 7.67 (2H, t, J=7.5 Hz, Ar—H), 7.41 (2H, t, J=7.7 Hz, Ar—H), 7.35-7.27 (6H, m, Ar—H), 5.04 (2H, d, J=13.9 Hz, Ar—CH$_2$), 3.64 (2H, d, J=14.2 Hz, Ar—CH$_2$), 3.55-3.47 (2H, m, N—CH$_2$—CH$_3$), 2.73 (2H, q, J=6.9H, N—CH$_2$—CH$_3$), 0.64 (6H, t, J=6.9 Hz, CH$_3$).

Example 6

Synthesis of Quaternary Ammonium Salt (Compound 13)

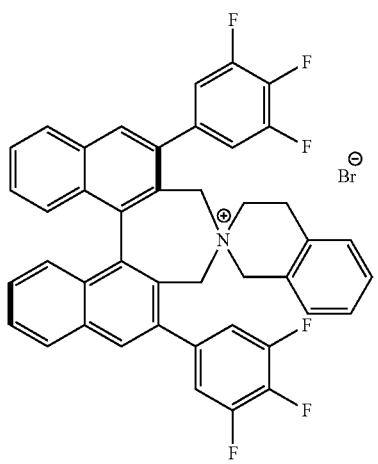

(13)

The same procedure as in Example 1 was performed except that the R-form of the compound 6 (140 mg, 0.2 mmol) was used and 1,2,3,4-tetrahydroisoquinoline was used instead of dibutylamine. The product was purified by silica gel column chromatography to give a compound 13 (117 mg, 0.16 mmol) in a 78% yield.

The NMR spectrum of the obtained compound was as follows: $^1$H NMR (400 MHz, CDCl$_3$) δ 8.08-8.02 (4H, m, Ar—H), 7.71-7.63 (2H, m, Ar—H), 7.47-7.35 (4H, m, Ar—H), 7.26-7.14 (3H, m, Ar—H), 7.07 (2H, dd, J=7.5, 7.5 Hz, Ar—H), 6.99 (2H, d, J=7.5 Hz, Ar—H), 6.63 (1H, d, J=7.5 Hz, Ar—H), 5.45 (1H, d, J=15.0 Hz, N—CH$_2$), 5.42 (1H, d, J=13.9 Hz, N—CH$_2$), 4.83 (1H, d, J=12.7 Hz, N—CH$_2$), 4.12 (1H, d, J=13.9 Hz, N—CH$_2$), 3.94-3.86 (2H, m, N—CH$_2$), 3.66 (1H, dd, J=11.7, 6.1 Hz), 3.36 (1H, dt, J=12.4, 5.3 Hz), 3.15-3.06 (1H, m), 2.83 (1H, dd, J=18.2, 4.7 Hz, CH$_3$).

Example 7

Synthesis of Quaternary Ammonium Salt (Compound 14)

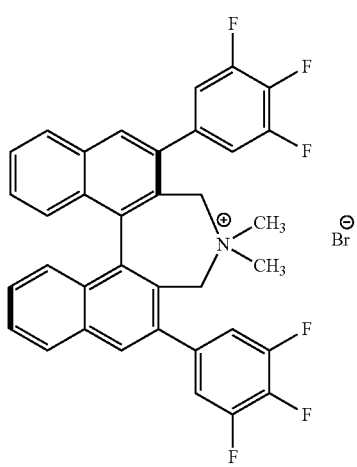

(14)

The same procedure as in Example 1 was performed except that the S-form of the compound 6 (140 mg, 0.2 mmol) was used and dimethylamine was used instead of dibutylamine. The product was purified by silica gel column chromatography to give a compound 14 (117 mg, 0.18 mmol) in a 88% yield.

The NMR spectrum of the obtained compound was as follows: $^1$H NMR (400 MHz, CDCl$_3$) δ 8.03-8.01 (4H, m, Ar—H), 7.64 (2H, t, J=7.3 Hz, Ar—H), 7.41-7.35 (4H, m, Ar—H), 7.12 (4H, bs, Ar—H), 4.92 (2H, d, J=13.5 Hz, Ar—CH$_2$), 3.76 (2H, d, J=13.9 Hz, Ar—CH$_2$), 2.96 (6H, s, N—CH$_3$).

Example 8

Synthesis of Quaternary Ammonium Salt (Compound 15)

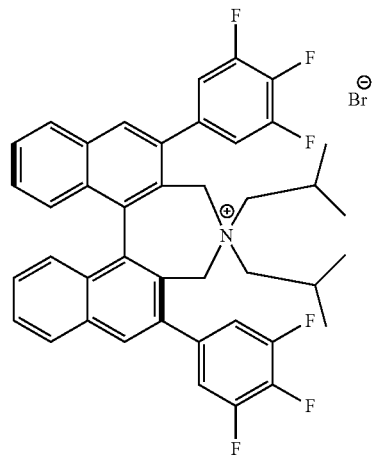

(15)

The same procedure as in Example 1 was performed except that the S-form of the compound 6 (140 mg, 0.2 mmol) was used and diisobutylamine was used instead of dibutylamine. The product was purified by silica gel column chromatography to give a compound 15 (137 mg, 0.18 mmol) in a 91% yield.

The NMR spectrum of the obtained compound was as follows: $^1$H NMR (400 MHz, CDCl$_3$) δ 8.00-7.96 (4H, m, Ar—H), 7.58-7.54 (2H, m, Ar—H), 7.34-7.21 (8H, m, Ar—H), 4.54 (2H, d, J=13.1 Hz, Ar—CH$_2$), 4.11 (2H, d, J=13.4 Hz, Ar—CH$_2$), 3.08 (2H, dd, J=13.3, 4.9 Hz, N—CH$_2$—CH), 2.39 (2H, dd, J=13.4, 4.9 Hz, N—CH$_2$—CH), 2.00-1.93 (2H, m, CH), 0.86 (2H, d, J=6.3 Hz, CH$_3$), 0.76 (2H, d, J=6.7 Hz, CH$_3$).

Example 9

Synthesis of Quaternary Ammonium Salt (Compound 16)

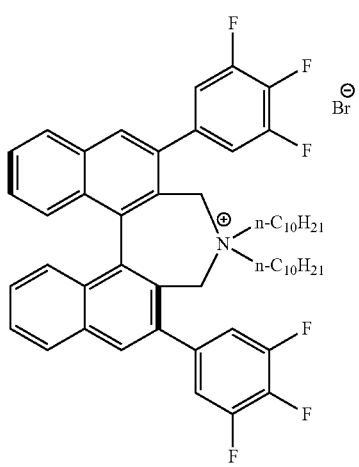

(16)

The same procedure as in Example 1 was performed except that the S-form of the compound 6 (140 mg, 0.2 mmol) was used and di-n-decylamine was used instead of dibutylamine. The product was purified by silica gel column chromatography to give a compound 16 (117 mg, 0.13 mmol) in a 64% yield.

The NMR spectrum of the obtained compound was as follows: $^1$H NMR (400 MHz, CDCl$_3$) δ 7.98-7.97 (4H, m, Ar—H), 7.57-7.53 (2H, m, Ar—H), 7.32-7.27 (8H, m, Ar—H), 4.96 (2H, d, J=13.9 Hz, Ar—CH$_2$), 3.76 (2H, d, J=14.2 Hz, Ar—CH$_2$), 3.22 (2H, t, J=12.7 Hz, Ar—CH$_2$), 2.78 (1H, t, J=8.1 Hz, Ar—CH$_2$), 2.60 (2H, t, J=11.1 Hz, CH$_2$), 1.80 (1H, bs), 1.29-0.85 (34H, m), 0.34 (2H, m).

Reference Example 2

Synthesis of Starting Material (Compound 18) for Synthesizing Quaternary Ammonium Salt

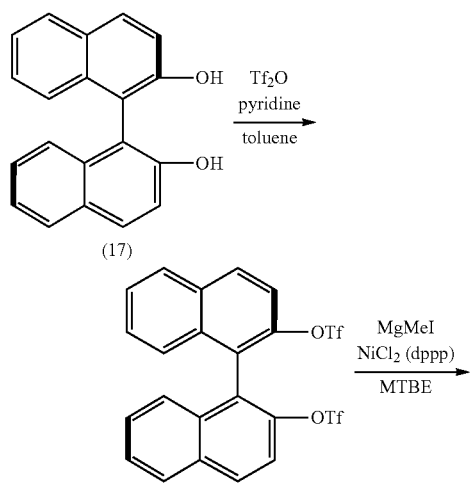

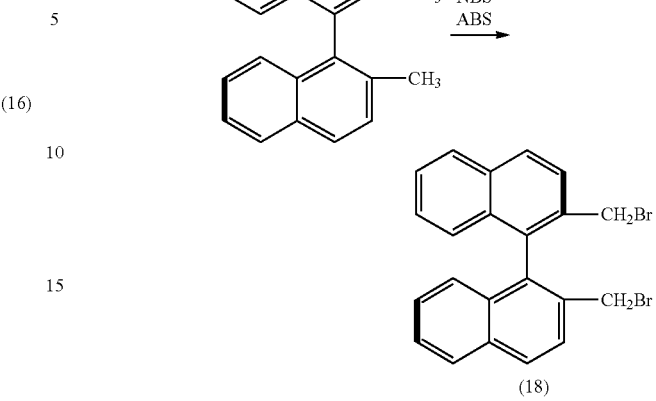

To a mixture of a compound 17 (R-form) and pyridine in 4 equivalents to the compound 17, 3 equivalents of trifluoromethane sulfonic acid anhydride (Tf$_2$O) in toluene was added dropwise over 40 min under a nitrogen atmosphere at 2 to 9° C. with stirring. After the dropping of Tf$_2$O, the resulting mixture was stirred at room temperature for 3 hours. To this mixture, pyridine, water and 35% hydrochloric acid were added, then the organic layer was collected to give a trifurylated product quantitatively. Then, MeI (3 equivalents) was added dropwise to a Mg (3 equivalents) solution in tert-butyl methyl ester (MTBE), and NiCl$_2$ (dppp) (0.05 equivalents) was added thereto, and the trifurylated product was further added dropwise thereto. The reaction mixture was stirred at 55° C. under heating and reflux for 30 min, and toluene was added thereto. The resulting mixture was poured into cool water, and then hydrochloric acid was added thereto. Thereafter, the organic layer was collected to give a dimethylated product in a 96.1% yield. Then, N-bromosuccinimide (NBS; 2.5 equivalents) and 2,2'-azobisisobutyronitrile (AIBN; 0.05 equivalents) were added to the dimethylated product in cyclohexane at room temperature, and the reaction mixture was heated and refluxed for 2 hours with stirring. After the mixture was cooled to room temperature, ethyl acetate was added thereto and the mixture was stirred and poured into water. The two-layered mixture was stirred until no precipitate developed, and the precipitate was collected to give a compound 18 (R-form) in a 54.3% yield.

Example 10

Synthesis of Quaternary Ammonium Salt (Compound 19)

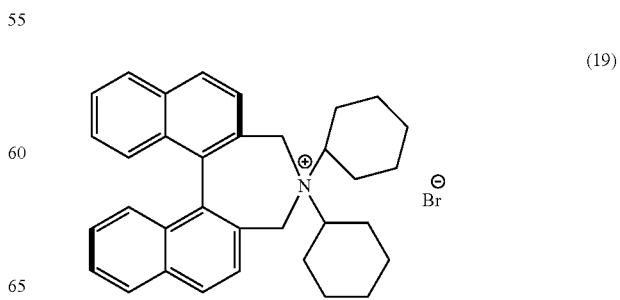

(19)

The same procedure as in Example 1 was performed except that the compound 18 (R-form) (88 mg, 0.2 mmol) was used and dicyclohexylamine was used instead of dibutylamine. The product was purified by silica gel column chromatography to give a compound 19 (54 mg, 0.10 mmol) in a 50% yield.

The NMR spectrum of the obtained compound was as follows: $^1$H NMR (400 MHz, CDCl$_3$) δ 8.12 (2H, d, J=8.3 Hz, Ar—H), 8.02 (2H, d, J=8.7 Hz, Ar—H), 7.90 (2H, d, J=8.3 Hz, Ar—H), 7.59 (2H, dd, J=7.6, 8.3 Hz, Ar—H), 7.42 (2H, d, J=8.7 Hz, Ar—H), 7.36 (2H, dd, J=7.6, 8.3 Hz, Ar—H), 5.40 (2H, d, J=12.7 Hz, Ar—CH$_2$), 3.61 (2H, d, J=13.5 Hz, Ar—CH$_2$), 3.36 (2H, t, J=11.9 Hz, CH$_2$), 3.17 (2H, bs, CH$_2$), 3.03 (2H, d, J=10.3 Hz, CH$_2$), 2.47 (2H, d, J=11.1 Hz, CH$_2$), 2.25-1.07 (14H, m).

Example 11

α-Benzylation by Various Phase-Transfer Catalysts

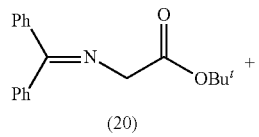
(20)

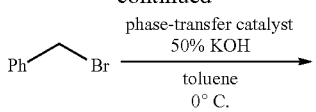

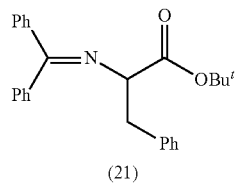
(21)

Glycine tert-butyl ester benzophenone Schiff base (compound 20) (14.8 mg, 0.5 mmol), phase-transfer catalysts in amounts as described in Table 1 below to the compound 20, 50% potassium hydroxide aqueous solution (1.0 mL), and toluene (3.0 mL) were mixed, and benzyl bromide (72.8 μg, 0.5 mmol) was added dropwise thereto at 0° C. After each was stirred at 0° C. for a period as described in Table 1 below, the reaction mixture was poured into water, and extracted with ether. The ether extract was washed with saturated brine, dried over sodium sulfate and concentrated under reduced pressure. The oily residue was subjected to silica gel column chromatography (eluted with ether/hexane=1/10) to give (S)-phenylalanine tert-butyl ester benzophenone Schiff base (compound 21). The optical purity of the obtained product was analyzed by HPLC [Daicel Chiralcel OD; eluent: hexane/2-propanol=100:1, 0.5 mL/min; retention time: (R)-form=14.8 min, (S)-form=28.2 min].

TABLE 1

| Phase-transfer catalyst (amount used) | Reaction time (hr) | Yield (%) | Optical purity (% ee) |
|---|---|---|---|
| 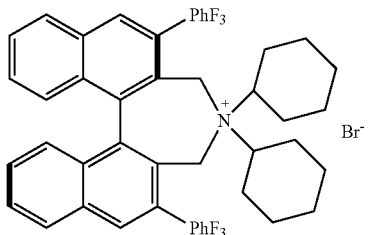<br>Compound 10 (1 mol %) | 48 | 14 | 5 |
| 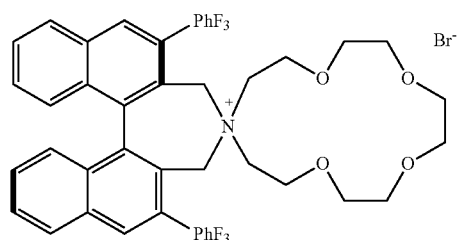<br>Compound 11 (1 mol %) | 20 | 94 | 87 |

TABLE 1-continued
| Phase-transfer catalyst (amount used) | Reaction time (hr) | Yield (%) | Optical purity (% ee) |
|---|---|---|---|
| 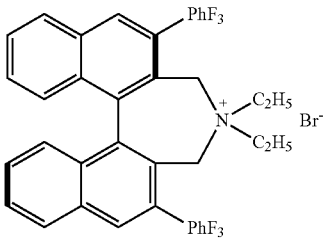<br>Compound 12 (1 mol %) | 48 | 14 | 89 |
| 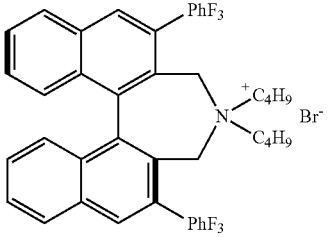<br>Compound 7 (3 mol %) | 21 | 86 | 97 |
| 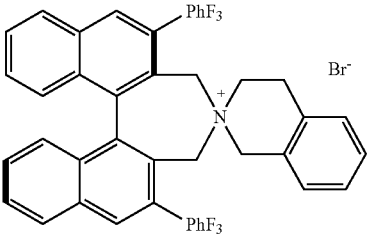<br>Compound 13 (1 mol %) | 32 | 80 | 85 |
| 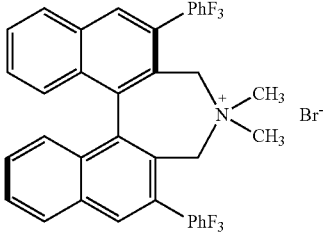<br>Compound 14 (3 mol %) | 54 | 63 | 14 |
| 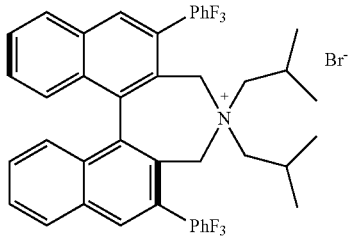<br>Compound 15 (3 mol %) | 36 | 80 | 1 |

TABLE 1-continued

| Phase-transfer catalyst (amount used) | Reaction time (hr) | Yield (%) | Optical purity (% ee) |
|---|---|---|---|
| 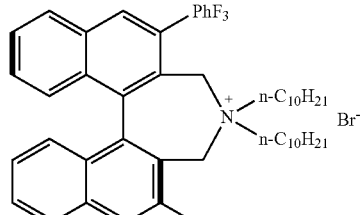 Compound 16 (1 mol %) | 48 | 20 | 98 |
| 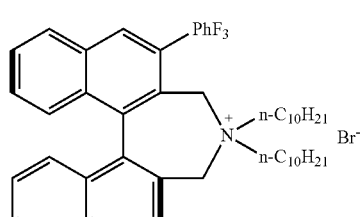 Compound 16 (3 mol %) | 48 | 18 | 97 |
| 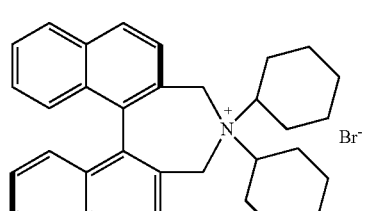 Compound 19 (3 mol %) | 7 days | 11 | 6 |

Example 12

Examination of Effect of Temperature of α-Benzylation

According to Example 11, α-benzylation was performed at 0° C. or room temperature, using 3 mol % of a phase-transfer catalyst (compound 7 (R) or compound 16 (S)). The results are shown in Table 2.

TABLE 2

| Phase-transfer catalyst | Reaction temperature | Reaction time (hr) | Yield (%) | Optical purity (% ee) |
|---|---|---|---|---|
| 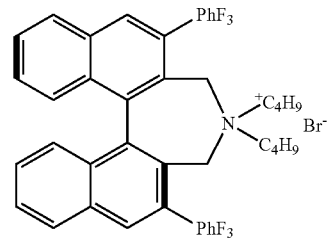 Compound 7 | 0° C. | 21 | 86 | 97 |
|  | room temperature | 3 | 95 | 71 |

TABLE 2-continued

| Phase-transfer catalyst | Reaction temperature | Reaction time (hr) | Yield (%) | Optical purity (% ee) |
| --- | --- | --- | --- | --- |
| Compound 16 | 0° C. | 48 | 18 | 97 |
| | room temperature | 1 | 91 | 92 |

There is a tendency that when the temperature is high, the reaction time is short and the yield is good, but the optical purity is good when the temperature is low.

Reference Example 3

Synthesis of Starting Material (Compound 24 and Compound 25) for Synthesizing Quaternary Ammonium Salt

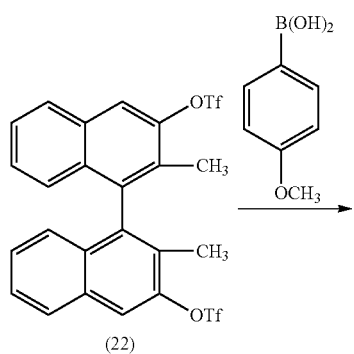

(22)

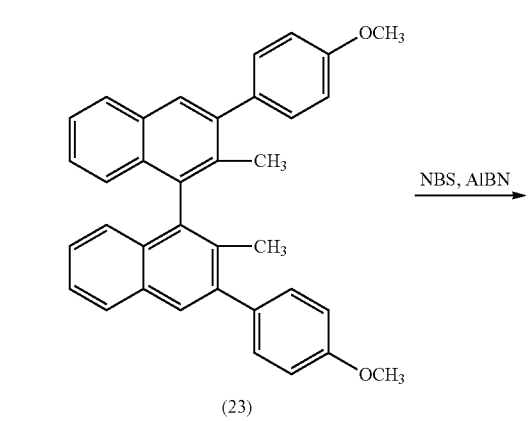

(23)

NBS, AIBN →

-continued

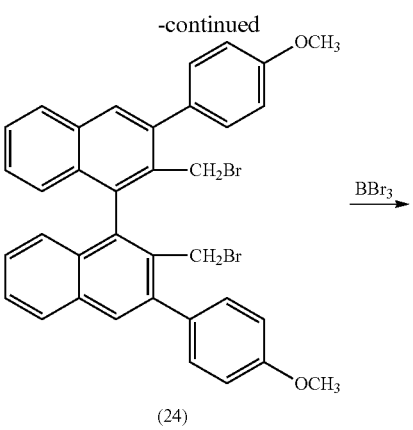

(24)

BBr₃ →

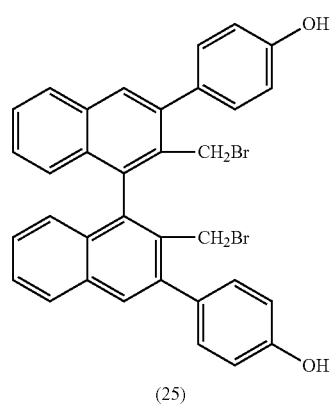

(25)

The compound 22 (S-form) and 4-methoxyphenyl boronic acid in 2 equivalents to the compound 22 (S-form) were subjected to a Suzuki coupling reaction to give a compound 23 in a good yield. The compound was heated and refluxed together with 2.2 equivalents of N-bromosuccinimide (NBS) and 0.1 equivalents of 2,2'-azobisisobutyronitrile (AIBN) in benzene to give a compound 24 in a good yield. Then, the compound 24 was treated with 2.4 equivalents of BBr$_3$ to give a compound 25 in a good yield. The R-form can be prepared in the same procedure.

Example 13

Synthesis of Quaternary Ammonium Salt (Compound 26)

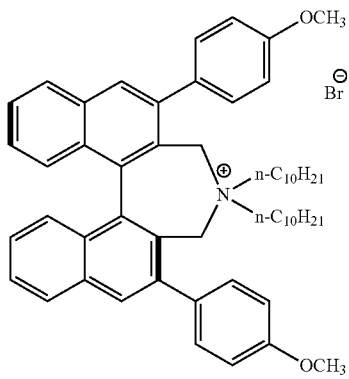
(26)

The same procedure as in Example 1 was performed except that the compound 24 (S-form) was used and di-n-decylamine was used instead of dibutylamine. The product was purified by silica gel column chromatography to give a compound 26 in a good yield.

Example 14

Synthesis of Quaternary Ammonium Salt (Compound 27)

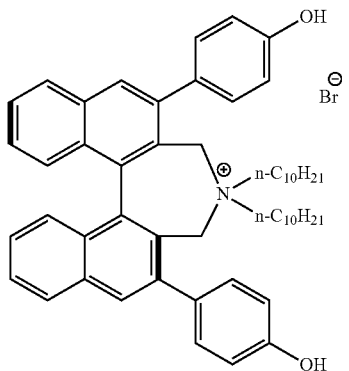
(27)

The same procedure as in Example 1 was performed except that the compound 25 (S-form) was used and di-n-decylamine was used instead of dibutylamine. The product was purified by silica gel column chromatography to give a compound 27 in a good yield.

The NMR spectrum of the obtained compound was as follows: $^1$H NMR (400 MHz, CD Cl$_3$) δ 8.04 (2H, s, Ar—H), 7.99 (2H, d, J=8.3 Hz, Ar—H), 7.62-7.59 (2H, m, Ar—H), 7.37-7.22 (12H, m, Ar—H), 4.92 (2H, d, J=13.1 Hz, Ar—CH$_2$), 3.43 (2H, d, J=13.1 Hz, Ar—CH$_2$), 3.17 (2H, brs, —CH$_2$—), 2.74-2.68 (2H, m, —CH$_2$—), 1.25-0.82 (36H, m, —CH$_2$—, —CH$_2$—), 0.34 (2H, brs, —CH$_2$—).

Reference Example 4

Synthesis of Starting Material (Compound 29) for Synthesizing Quaternary Ammonium Salt

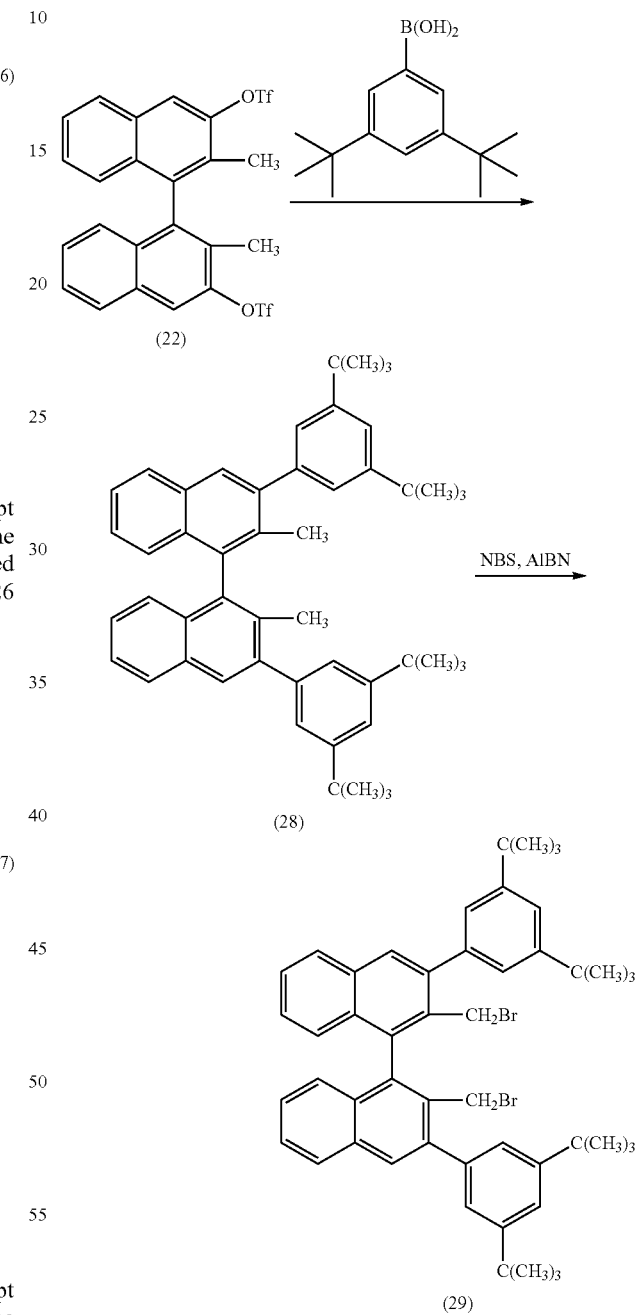

The compound 22 (S-form) and 3,5-di-tert-butylphenyl boronic acid in 2 equivalents to the compound 22 were subjected to a Suzuki coupling reaction in barium hydroxide hexahydrate in 3 equivalents to the compound 22, 5 mol % of palladium acetate and 1.2 mol % of triphenylphosphine in water and dimethyl ether for 7 hours under reflux. The resulting mixture was cooled to room temperature, and a saturated ammonium chloride solution was added thereto, and the mixture was extracted with ethyl ether to give a compound 28 in a 88% yield. Then, the compound 28 was refluxed together with 2 equivalents of NBS and 0.1 equivalents of AIBN in benzene for one hour and concentrated, and then subjected to silica gel column chromatography to give a compound 29 in a 77% yield. The R-form can be prepared in the same procedure.

Example 15

Synthesis of Quaternary Ammonium Salt (Compound 30)

(30)

The same procedure as in Example 1 was performed except that the compound 29 (S-form) was used and di-n-decylamine was used instead of dibutylamine. The product was purified by silica gel column chromatography to give a compound 30 in a good yield.

Reference Example 5

Synthesis (1) of Starting Material (Compound 32) for Synthesizing Quaternary Ammonium Salt

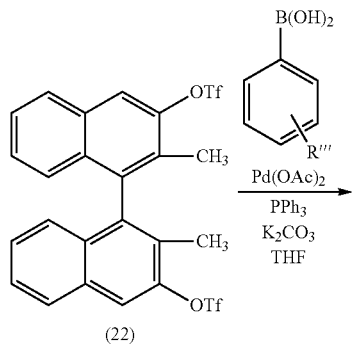

(22)

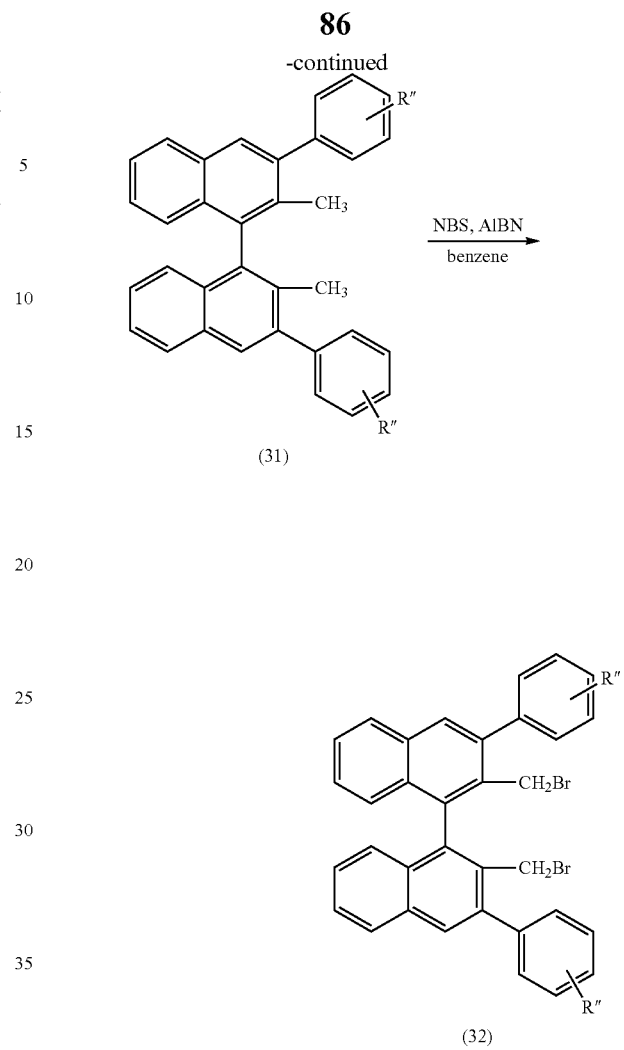

(where R″ is p-fluoro, m-fluoro, 3,4-difluoro, 3,4,5-trifluoro, p-chloro, m-chloro, 3,4,5-trichloro, 3,5-trifluoromethyl, 3,5-di-tert-butyl, p-methoxy, p-trifluoromethoxy, p-hydroxy, 3,5-diphenyl, p-(3,4,5-trifluorophenyl), p-(2,3,4,5,6-pentafluorophenyl), m-cyano, or m-nitro, and two R″ may be the same or different).

The compound 22 (S-form) and an aryl boronic acid derivative in 2 equivalents to the compound 22 were subjected to a Suzuki coupling reaction in 3 equivalents of potassium hydroxide or potassium phosphate, 5 mol % of palladium acetate and 1.2 mol % of triphenylphosphine in tetrahydrofuran for 7 hours under reflux. The resulting mixture was cooled to room temperature, and a saturated ammonium chloride solution was added thereto, and the mixture was extracted with ethyl ether to give a compound 31 in a 87% yield. Then, the compound 31 was refluxed with 2 equivalents of N-bromosuccinimide and 0.1 equivalents of 2,2′-azobisisobutyronitrile in benzene for one hour and concentrated, and then was subjected to silica gel column chromatography to give a compound 32 in a 97% yield. The R-form can be prepared in the same procedure.

Example 16

Synthesis (1) of Quaternary Ammonium Salt (Compound 33)

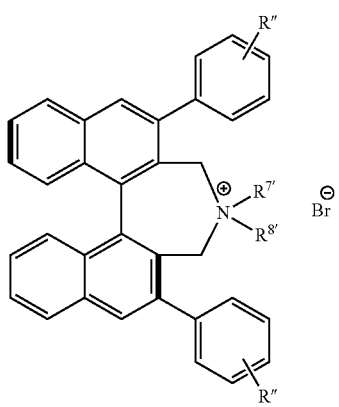

The same procedure as in Example 1 was performed except that the compound 32 (S-form) was used and dibutylamine as used in Example 1 or diamine $R^7$—NH—$R^8$ (where $R^7$ and $R^8$ are the same and are methyl, n-butyl, isobutyl, 1-hydroxyethyl, 1-methoxyethyl, n-decyl, cyclohexyl, or 1-propynyl, or $R^7$ and $R^8$ are taken together to form:

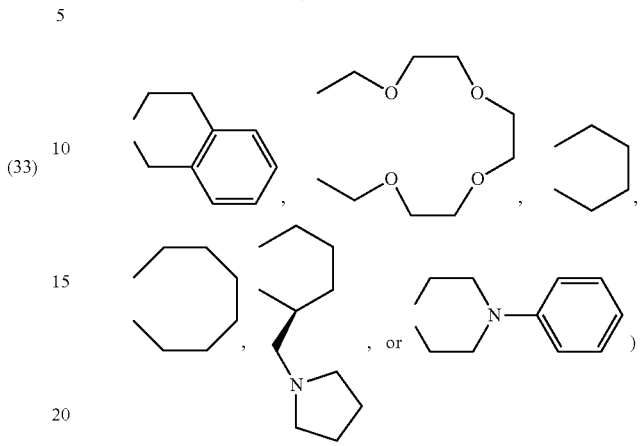

was used instead of dibutylamine used in Example 1. The product was purified by silica gel column chromatography to give a compound 33 in a good yield. The R-form can be prepared in the same procedure.

The structural formulae and the NMR spectrum data of the obtained specific compounds are shown in Tables 3 to 7.

TABLE 3

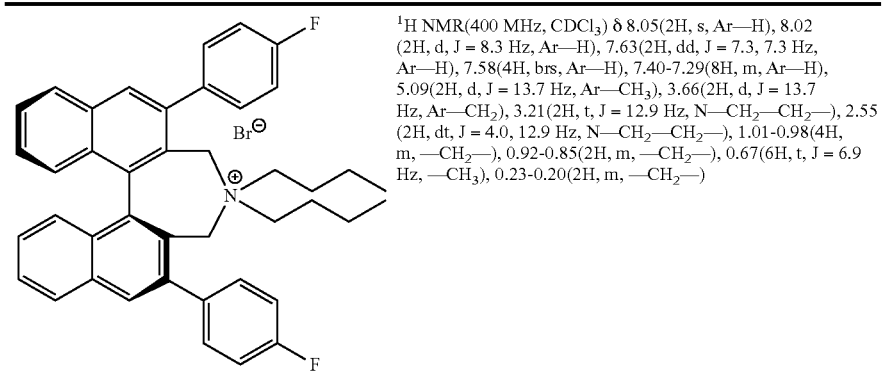

$^1$H NMR(400 MHz, CDCl$_3$) δ 8.05(2H, s, Ar—H), 8.02 (2H, d, J = 8.3 Hz, Ar—H), 7.63(2H, dd, J = 7.3, 7.3 Hz, Ar—H), 7.58(4H, brs, Ar—H), 7.40-7.29(8H, m, Ar—H), 5.09(2H, d, J = 13.7 Hz, Ar—CH$_3$), 3.66(2H, d, J = 13.7 Hz, Ar—CH$_2$), 3.21(2H, t, J = 12.9 Hz, N—CH$_2$—CH$_2$—), 2.55 (2H, dt, J = 4.0, 12.9 Hz, N—CH$_2$—CH$_2$—), 1.01-0.98(4H, m, —CH$_2$—), 0.92-0.85(2H, m, —CH$_2$—), 0.67(6H, t, J = 6.9 Hz, —CH$_3$), 0.23-0.20(2H, m, —CH$_2$—)

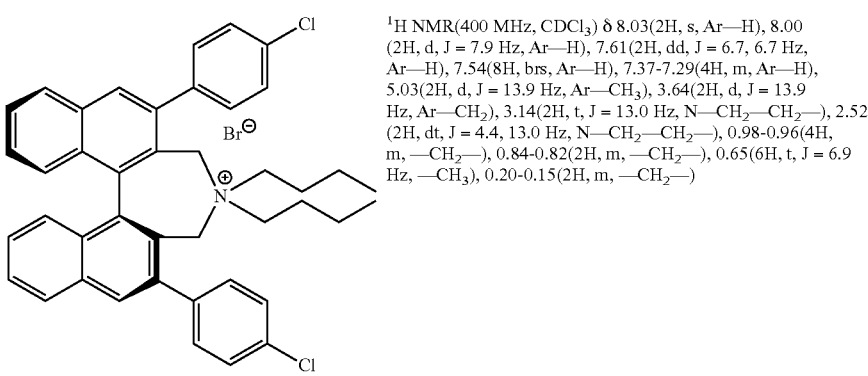

$^1$H NMR(400 MHz, CDCl$_3$) δ 8.03(2H, s, Ar—H), 8.00 (2H, d, J = 7.9 Hz, Ar—H), 7.61(2H, dd, J = 6.7, 6.7 Hz, Ar—H), 7.54(8H, brs, Ar—H), 7.37-7.29(4H, m, Ar—H), 5.03(2H, d, J = 13.9 Hz, Ar—CH$_3$), 3.64(2H, d, J = 13.9 Hz, Ar—CH$_2$), 3.14(2H, t, J = 13.0 Hz, N—CH$_2$—CH$_2$—), 2.52 (2H, dt, J = 4.4, 13.0 Hz, N—CH$_2$—CH$_2$—), 0.98-0.96(4H, m, —CH$_2$—), 0.84-0.82(2H, m, —CH$_2$—), 0.65(6H, t, J = 6.9 Hz, —CH$_3$), 0.20-0.15(2H, m, —CH$_2$—)

TABLE 3-continued

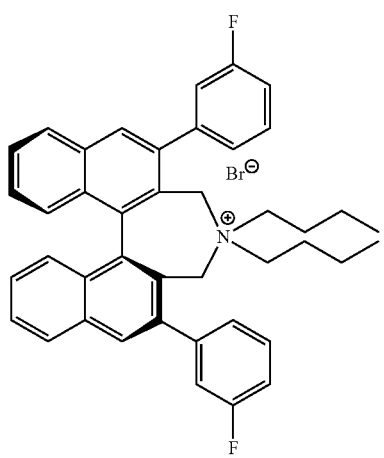

¹H NMR(400 MHz, CDCl$_3$) δ 8.02(2H, s, Ar—H), 7.98 (2H, d, J = 8.3 Hz, Ar—H), 7.60-7.57(4H, m, Ar—H), 7.35-7.28(8H, m, Ar—H), 7.12(2H, dd, J = 8.3 Hz, Ar—H), 5.03(2H, br, N—CH$_2$—), 3.61(2H, d, J = 12.7 Hz, N—CH$_2$—), 3.15(2H, br, N—CH$_2$—), 2.51(2H, brs, N—CH$_2$—), 0.95-0.89 (6H, m, —CH$_2$—), 0.61(6H, t, J = 6.1 Hz, —CH$_3$), 0.13(2H, brs, —CH$_2$—)

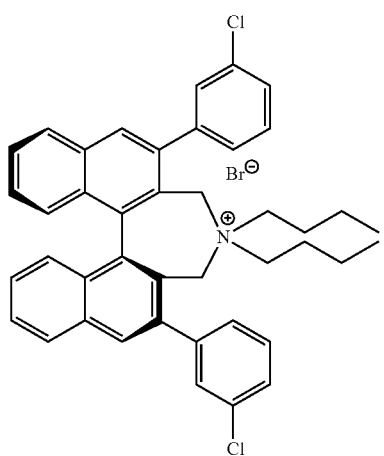

¹H NMR(400 MHz, CDCl$_3$) δ 8.03(2H, s, Ar—H), 8.00(2H, d, J = 7.9 Hz, Ar—H), 7.61(2H, dd, J = 7.3 Hz, Ar—H), 7.56(4H, brs, Ar—H), 7.43(2H, d, J = 7.5 Hz, Ar—H), 7.37-7.29(6H, m, Ar—H), 5.05(2H, brs, N—CH$_2$), 3.60(2H, brs, N—CH$_3$), 3.19(2H, brs, N—CH$_2$—), 2.51(2H, brs, N—CH$_2$—), 0.97-0.84(6H, m, —CH$_2$—), 0.65(6H, t, J = 6.7 Hz, —CH$_3$), 0.15(2H, brs, —CH$_2$—)

TABLE 4

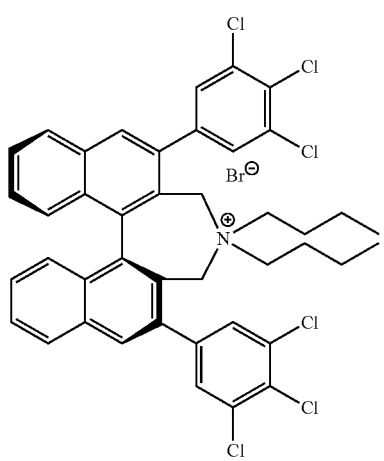

¹H NMR(400 MHz, CDCl$_3$) δ 8.05(2H, s, Ar—H), 8.05 (2H, d, J =8.0 Hz, Ar—H), 7.73-7.63(5H, m, Ar—H), 7.42 (2H, dd, J = 8.3, 8.3 Hz, Ar—H), 7.33(2H, d, J =8.3 Hz, Ar—H), 4.99(2H, d, J =13.9 Hz, Ar—CH$_2$), 3.78(2H, d, J = 13.9 Hz, Ar—CH$_3$), 3.34(2H, t, J = 13.5 Hz, N—CH$_2$—CH$_2$—), 2.67(2H, dt, J = 4.7, 13.1 Hz, N—CH$_2$—CH$_2$—), 1.13-1.11 (4H, m, —CH$_2$—), 1.03-0.99(2H, m, —CH$_2$—), 0.73(6H, t, J = 7.5 Hz, —CH$_3$), 0.39-0.35(2H, m, —CH$_2$—)

TABLE 4-continued

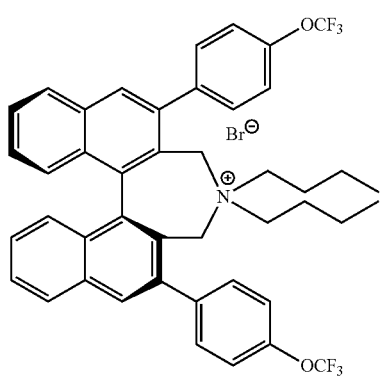

$^1$H NMR(400 MHz, CDCl$_3$) δ 8.06(2H, s, Ar—H), 8.03 (2H, d, J = 7.9 Hz, Ar—H), 7.66-7.62(6H, m, Ar—H), 7.45-7.32(8H, m, Ar—H), 5.07(2H, d, J = 13.9 Hz, Ar—CH$_2$), 3.70(2H, d, J = 13.9 Hz, Ar—CH$_2$), 3.20(2H, t, J = 12.5 Hz, N—CH$_2$—CH$_2$—), 2.57(2H, t, J = 12.9 Hz, N—CH$_2$—CH$_2$—), 0.98-0.95(4H, m, —CH$_2$—), 0.90-0.87(2H, m, —CH$_2$—), 0.65(6H, t, J = 6.9 Hz, —CH$_3$), 0.25-0.21(2H, m, —CH$_2$—)

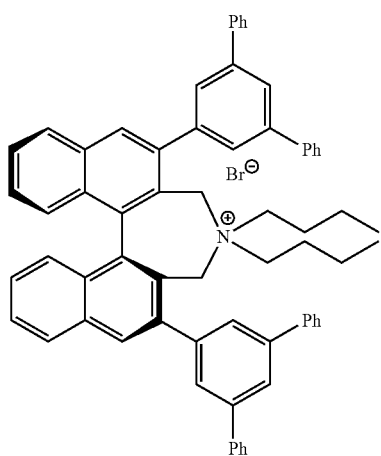

$^1$H NMR(400 MHz, CDCl$_3$) δ 8.21(2H, s, Ar—H), 8.08 (2H, d, J = 8.3 Hz, Ar—H), 7.99(2H, s, Ar—H), 7.94(2H, s, Ar—H), 7.82-7.78(8H, m, Ar—H), 7.69-7.62(4H, m, Ar—H), 7.53-7.33(16H, m, Ar—H), 5.15(2H, d, J = 13.7 Hz, Ar—CH$_2$), 3.87(2H, d, J = 13.7 Hz, Ar—CH$_2$), 3.24(2H, t, J = 12.5 Hz, N—CH$_2$—CH$_2$—), 2.77(2H, dt, J = 4.4, 12.7 Hz, N—CH$_2$—CH$_2$—), 1.00-0.95(4H, m, —CH$_2$—), 0.82-0.78(2H, m, —CH$_2$—), 0.47-0.44(8H, m, —CH$_2$—, —CH$_3$)

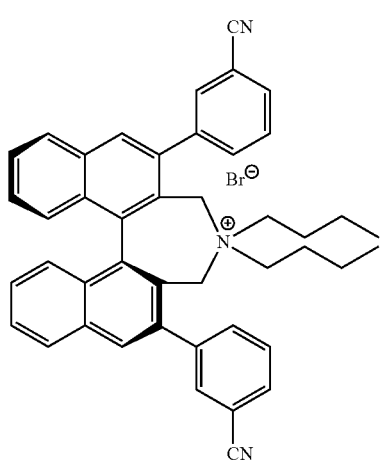

$^1$H NMR(400 MHz, CDCl$_4$, 65° C.) δ 8.07-7.99(6H, m, Ar—H), 7.82-7.77(6H, m, Ar—H), 7.67(2H, dd, J = 7.7, 7.7 Hz, Ar—H), 7.41(2H, dd, J = 7.7, 7.7 Hz, Ar—H), 7.33(2H, d, J = 7.9 Hz, Ar—H), 5.01(2H, brs, N—CH$_2$), 3.76-3.74 (2H, m, N—CH$_2$—), 3.31(2H, br, N—CH$_2$), 2.56(2H, brs, N—CH$_2$—), 1.05(4H, brs, —CH$_2$—), 0.93-0.92(2H, m, —CH$_2$—), 0.69(6H, t, J = 7.1 Hz, —CH$_3$), 0.24(2H, brs, —CH$_2$—)

TABLE 5

| Structure | NMR Data |
|---|---|
| (Binaphthyl-azepinium with 3,5-bis(CF₃)phenyl groups, Br⁻) | ¹H NMR(400 MHz, CDCl₃) δ 8.22(2H, brs, Ar—H), 8.10-8.05(8H, m, Ar—H), 7.73-7.69(2H, m, Ar—H), 7.48-7.44(2H, m, Ar—H), 7.40-7.38(2H, m, Ar—H), 4.83 (2H, d, J = 14.3 Hz, Ar—CH₂), 4.03(2H, d, J = 14.3 Hz, Ar—CH₂), 3.37(2H, t, J = 13.1 Hz, N—CH₂—CH₂—), 2.65 (2H, t, J = 12.9 Hz, N—CH₂—CH₂—), 1.10(4H, brs, —CH₂—), 0.87(2H, brs, —CH₂—), 0.63(6H, t, J = 6.7 Hz, —CH₃), 0.32 (2H, brs, —CH₂—) |
| (Binaphthyl-azepinium with 4-OCH₃ phenyl groups, Br⁻) | ¹H NMR(400 MHz, CDCl₃) δ 8.01(2H, s, Ar—H), 7.97(2H, d, J = 7.9 Hz, Ar—H), 7.60-7.56(2H, m, Ar—H), 7.46(4H, brs, Ar—H), 7.32-7.31(4H, m, Ar—H), 7.08(4H, d, J = 8.0 Hz, Ar—H), 5.05(2H, d, J = 13.5 Hz, Ar—CH₂), 3.84(6H, s, —OCH₃), 3.57(2H, d, J = 13.5 Hz, Ar—CH₂), 3.03(2H, t, J = 13.1 Hz, N—CH₂—CH₂—), 2.52(2H, dt, J = 4.0, 12.3 Hz, N—CH₂—CH₂—), 0.94-0.87(6H, m, —CH₂—), 0.62(6H, t, J = 6.9 Hz, —CH₃), 0.21-0.17(2H, brs, —CH₂—) |
| (Binaphthyl-azepinium with 3-NO₂ phenyl groups, Br⁻) | ¹H NMR(400 MHz, CDCl₃, 65° C.) δ 8.34(2H, s, Ar—H), 8.33(2H, d, J = 7.9 Hz, Ar—H), 8.12(2H, s, Ar—H), 8.10-8.06(4H, m, Ar—H), 7.90(2H, dd, J = 7.7, 7.7 Hz, Ar—H), 7.68(2H, dd, J = 7.1, 7.1 Hz, Ar—H), 7.43(2H, dd, J = 7.3, 7.3 Hz, Ar—H), 7.36(2H, d, J = 8.7 Hz, Ar—H), 5.05(2H, brs, N—CH₂—), 3.78(2H, d, J = 13.1 Hz, N—CH₂—), 3.35(2H, brs, N—CH₂—), 2.56(2H, t, J = 12.7 Hz, N—CH₂—), 1.01-0.99(4H, m, —CH₂—), 0.82-0.80(2H, m, —CH₂—), 0.58(6H, t, J = 7.5 Hz, —CH₃), 0.22(2H, brs, —CH₂—) |
| (Binaphthyl-azepinium with 4-OCH₃ phenyl and 3-NO₂ phenyl groups, Br⁻) | ¹H NMR(400 MHz, CDCl₃, 65° C.) δ 8.37(1H, s, Ar—H), 8.32(1H, d, J = 8.3 Hz, Ar—H), 8.24(1H, d, J = 7.5 Hz, Ar—H), 8.12(1H, s, Ar—H), 8.08-7.96(4H, m, Ar—H), 7.68-7.61(2H, m, Ar—H), 7.43-7.30(6H, m, Ar—H), 7.09(2H, d, J = 7.9 Hz, Ar—H), 5.26(1H, brs, N—CH₂—), 4.96(1H, d, J = 12.3 Hz, N—CH₂—), 3.88(3H, s, —OCH₃), 3.78(1H, d, J = 13.9 Hz, N—CH₂—), 3.59(2H, d, J = 12.3 Hz, N—CH₂—), 2.82-2.78(1H, m, N—CH₂—), 2.57(2H, brs, N—CH₂—), 1.08(2H, brs, —CH₂—), 0.93(4H, brs, —CH₂—), 0.66(3H, t, J = 6.1 Hz, —CH₃), 0.58(3H, t, J = 7.2 Hz, —CH₃), 0.32-0.24(2H, m, —CH₂—) |

TABLE 6

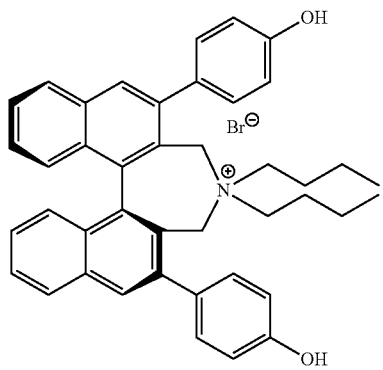

¹H NMR(400 MHz, CD₃OD) δ 8.12(2H, s, Ar—H), 8.09 (2H, d, J = 8.3 Hz, Ar—H), 7.64-7.60(2H, m, Ar—H), 7.51-7.22(8H, m, Ar—H), 6.96(4H, brs, Ar—H), 4.86(2H, d, J = 13.5 Hz, Ar—CH₂), 3.58(2H, d, J = 13.5 Hz, Ar—CH₂), 2.74(2H, t, J = 12.7 Hz, N—CH₂—CH₂—), 2.55 (2H, brs, N—CH₂—CH₂—), 1.00-0.95(6H, m, —CH₂—), 0.71 (6H, t, J = 6.3 Hz, —CH₃), 0.23(2H, brs, —CH₂—)

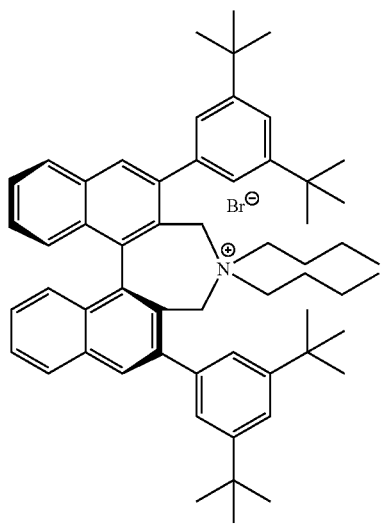

¹H NMR(400 MHz, CDCl₃) δ 8.09(2H, s, Ar—H), 8.06 (2H, d, J = 8.3 Hz, Ar—H), 7.66-7.62(2H, m, Ar—H), 7.57 (2H, s, Ar—H), 7.47(2H, s, Ar—H), 7.42-7.37(4H, m, Ar—H), 7.21(2H, s, Ar—H), 5.09(2H, d, J = 13.5 Hz, Ar—CH₂), 3.79(2H, d, J = 13.5 Hz, Ar—CH₂), 3.16(2H, t, J = 13.1 Hz, N—CH₂—CH₂—), 2.52(2H, t, J = 6.0, 13.3 Hz, N—CH₂—CH₂—), 1.42(18H, s, —CH₃), 1.37(18H, s, —CH₃), 1.05-1.02(4H, brs, —CH₂—), 0.84-0.82(2H, brs, —CH₂—), 0.62(6H, t, J = 6.9 Hz, —CH₃), 0.53-0.49(2H, brs, —CH₂—)

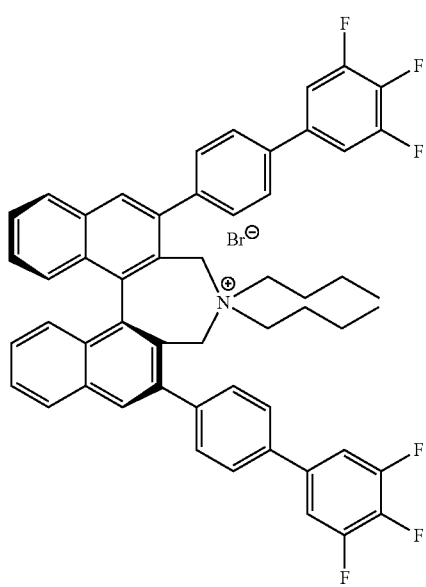

¹H NMR(400 MHz, CDCl₃) δ 8.12(2H, s, Ar—H), 8.05 (2H, d, J = 8.3 Hz, Ar—H), 7.74-7.64(10H, m, Ar—H), 7.42-7.36(4H, m, Ar—H), 7.30-7.26(4H, m, Ar—H), 5.20 (2H, d, J = 13.7 Hz, Ar—CH₂), 3.68(2H, d, J = 13.7 Hz, Ar—CH₂), 3.26(2H, t, J = 12.7 Hz, N—CH₂—CH₂—), 2.56 (2H, dt, J = 4.0, 12.7 Hz, N—CH₂—CH₂—), 0.98-0.96(4H, m, —CH₂—), 0.87-0.82(2H, m, —CH₂—), 0.53(6H, t, J = 6.9 Hz, —CH₃), 0.26-0.23(2H, m, —CH₂—)

TABLE 7

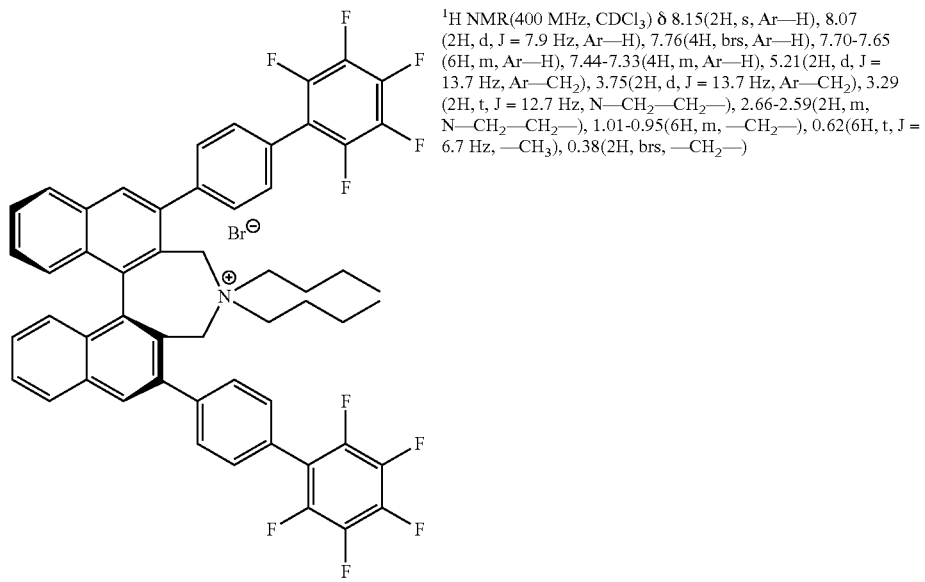

¹H NMR(400 MHz, CDCl₃) δ 8.15(2H, s, Ar—H), 8.07 (2H, d, J = 7.9 Hz, Ar—H), 7.76(4H, brs, Ar—H), 7.70-7.65 (6H, m, Ar—H), 7.44-7.33(4H, m, Ar—H), 5.21(2H, d, J = 13.7 Hz, Ar—CH₂), 3.75(2H, d, J = 13.7 Hz, Ar—CH₂), 3.29 (2H, t, J = 12.7 Hz, N—CH₂—CH₂—), 2.66-2.59(2H, m, N—CH₂—CH₂—), 1.01-0.95(6H, m, —CH₂—), 0.62(6H, t, J = 6.7 Hz, —CH₃), 0.38(2H, brs, —CH₂—)

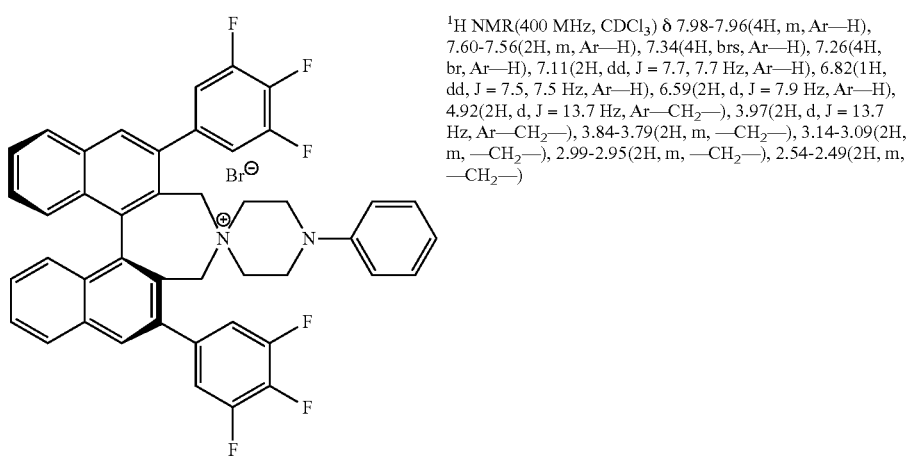

¹H NMR(400 MHz, CDCl₃) δ 7.98-7.96(4H, m, Ar—H), 7.60-7.56(2H, m, Ar—H), 7.34(4H, brs, Ar—H), 7.26(4H, br, Ar—H), 7.11(2H, dd, J = 7.7, 7.7 Hz, Ar—H), 6.82(1H, dd, J = 7.5, 7.5 Hz, Ar—H), 6.59(2H, d, J = 7.9 Hz, Ar—H), 4.92(2H, d, J = 13.7 Hz, Ar—CH₂—), 3.97(2H, d, J = 13.7 Hz, Ar—CH₂—), 3.84-3.79(2H, m, —CH₂—), 3.14-3.09(2H, m, —CH₂—), 2.99-2.95(2H, m, —CH₂—), 2.54-2.49(2H, m, —CH₂—)

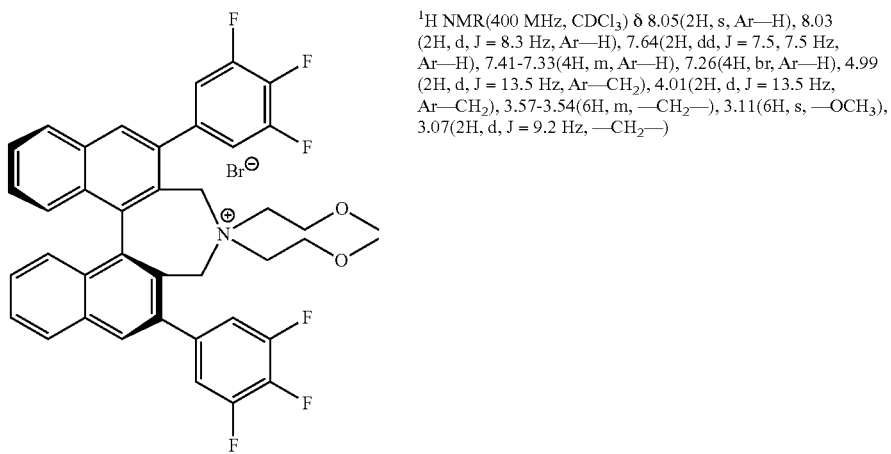

¹H NMR(400 MHz, CDCl₃) δ 8.05(2H, s, Ar—H), 8.03 (2H, d, J = 8.3 Hz, Ar—H), 7.64(2H, dd, J = 7.5, 7.5 Hz, Ar—H), 7.41-7.33(4H, m, Ar—H), 7.26(4H, br, Ar—H), 4.99 (2H, d, J = 13.5 Hz, Ar—CH₂), 4.01(2H, d, J = 13.5 Hz, Ar—CH₂), 3.57-3.54(6H, m, —CH₂—), 3.11(6H, s, —OCH₃), 3.07(2H, d, J = 9.2 Hz, —CH₂—)

Reference Example 6

Synthesis (2) of Starting Material (Compound 32') for Synthesizing Quaternary Ammonium Salt

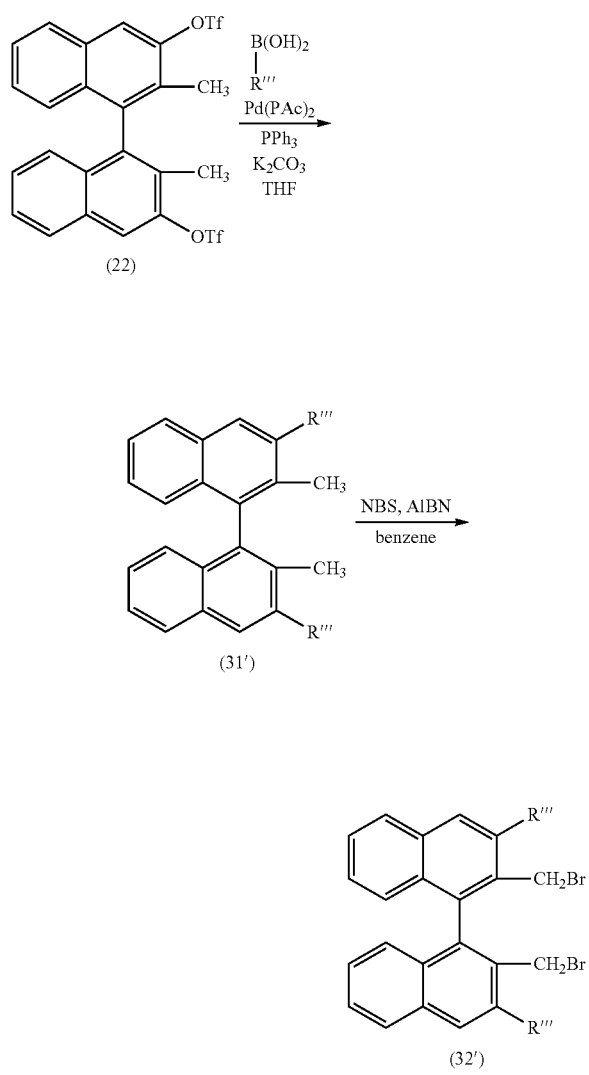

(where R''' is

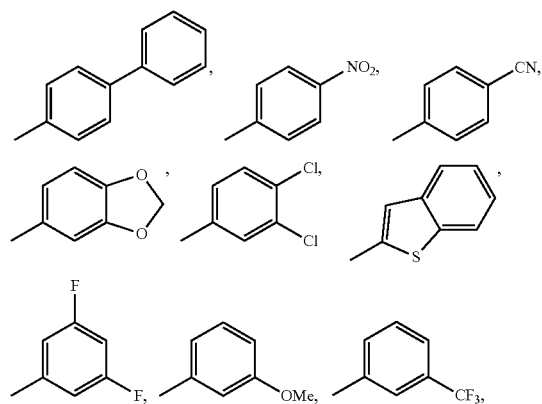

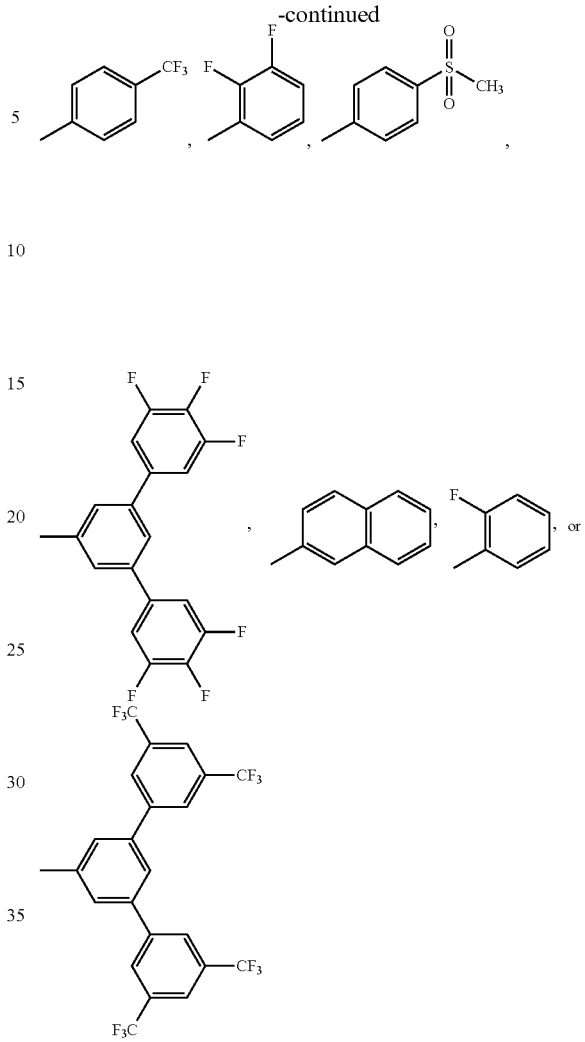

and the two R''' may be the same or different).

The compound 22 (S-form) and an aryl boronic acid derivative in 2 equivalents to the compound 22 were subjected to a Suzuki coupling reaction in 3 equivalents of potassium hydroxide or potassium phosphate, mol % of palladium acetate and 1.2 mol % of triphenylphosphine in tetrahydrofuran for 7 hours under reflux. The resulting mixture was cooled to room temperature, and a saturated ammonium chloride solution was added thereto, and the mixture was extracted with ethyl ether to give compounds 31' in yields below. Then, the compound 31 was refluxed with 2 equivalents of N-bromosuccinimide and 0.1 equivalents of 2,2'-azobisisobutyronitrile in benzene for one hour and concentrated, and then was purified by silica gel column chromatography to give compounds 32' in yields below. The specific structural formulae, the yields and the NMR spectrum data of the obtained compounds 31' and 32' are shown in Tables 8 to 15. The R-form can be prepared in the same procedure.

TABLE 8

| Compound 31' | Yield and NMR spectrum data |
|---|---|
|  | Yield: 74%, $^1$H NMR(400 MHz, CDCl$_3$) δ 2.03(s, 6H): 7.14 (d, J = 8.4 Hz, 2H); 7.25-7.27(m, 2H); 7.37-7.50(m, 8H); 7.57(d, J = 8.0 Hz, 8H); 7.70(tr, J = 8.0 Hz, 2H); 7.91(d, J = 10.0 Hz, 4H). |
|  | Yield: 74%, $^1$H NMR(400 MHz, CDCl$_3$) δ 1.94(s, 6H); 7.11 (d, J = 8.8 Hz, 2H); 7.29-7.32(m, 2H); 7.48(tr, J = 7.2 Hz, 2H); 7.67(dd, J = 7.2 Hz, 1.6 Hz, 2H); 7.86(s, 2H); 7.93(d, J = 8.0 Hz, 2H); 8.33(dd, J = 7.2 Hz, 1.6 Hz, 2H),). |
|  | Yield: 72.5%, $^1$H NMR(400 MHz, CDCl$_3$) δ 1.92(s, 6H); 7.09(d, 2H, J = 8.8 Hz); 7.29(tr, 2H, J = 8.0 Hz); 7.47(tr, J = 7.6 Hz, 2H); 7.60(d, J = 8.0 Hz, 2H); 7.77(d, J = 8.0 Hz, 2H); 7.83(s, 2H); 7.91(d, J = 8.4 Hz, 2H),). |
|  | Yield: 77%, $^1$H NMR(400 MHz, CDCl$_3$) δ 1.94(s, 6H); 6.02(s, 4H); 6.83-6.98(m, 6H); 7.07(d, J = 8.4 Hz, 2H); 7.20-7.25(m, 2H); 7.41(tr, J = 7.6 Hz, 2H); 7.81(s, 2H); 7.87(d, J = 8.4 Hz, 2H). |

TABLE 9

| Compound 31' | Yield and NMR spectrum data |
|---|---|
| (structure with 3,4-dichlorophenyl groups) | Yield: 69%, $^1$H NMR(400 MHz, CDCl$_3$) δ 1.92(s, 6H); 7.07(d, J = 8.4 Hz, 2H); 7.27-7.33(m, 4H); 7.45(tr, J = 7.6 Hz, 2H); 7.53(d, J = 8.4 Hz, 2H); 7.58(d, J = 2.0 Hz, 2H); 7.61(s, 2H); 7.89(d, J = 8.0 Hz, 2H). |
| (structure with benzothiophene groups) | Yield: 73%, $^1$H NMR(400 MHz, CDCl$_3$) δ 2.16(s, 6H); 7.11(d, J = 8.4 Hz, 2H); 7.27-7.29(m, 2H); 7.34-7.47(m, 8H); 7.83(dd, J = 7.0 Hz, 0.8 Hz, 2H); 7.88-7.93(m, 4H); 8.18(s, 2H). |
| (structure with 3,5-difluorophenyl groups) | Yield: 93%, $^1$H NMR(400 MHz, CDCl$_3$) δ 1.94(s, 6H); 6.83-6.88(m, 2H),); 7.00-7.05(m, 4H); 7.08(d, J = 8.4 Hz, 2H); 7.26-7.31(m, 2H); 7.44-7.48(m, 2H); 7.84 (s, 2H); 7.91(d, J = 8.4 Hz, 2H),). |
| (structure with 3-methoxyphenyl groups) | Yield: 60%, $^1$H NMR(400 MHz, CDCl$_3$) δ 1.95(s, 6H); 3.87(s, 6H,); 6.91-6.94(m, 2H); 7.02-7.11(m, 6H); 7.21-7.25(m, 2H); 7.35-7.43(m, 4H); 7.84-7.89(m, 4H). |

TABLE 10

| Compound 31' | Yield and NMR spectrum data |
|---|---|
| | Yield: 91%, ¹H NMR(400 MHz, CDCl₃): δ 1.94(s, 6H); 7.11(d, J = 8.4 Hz, 2H); 7.26-7.31(m, 2H); 7.44-7.48 (m, 2H); 7.58(d, J = 8.0 Hz, 2H); 7.64-7.68(m, 4H); 7.76(s, 2H); 7.86(s, 2H); 7.91(tr, J = 8.4 Hz, 2H). |
| | Yield: 81%, ¹H NMR(400 MHz, CDCl₃): δ 1.94(s, 6H); 7.11(d, J = 8.8 Hz, 2H); 7.26-7.32(m, 2H); 7.43-7.45(m, 2H); 7.59(d, J = 8.4 Hz, 4H); 7.71(d, J = 8.4 Hz, 4H); 7.83(s, 2H); 7.89(d, J = 8.0 Hz, 2H). |
| | Yield: 83%, ¹H NMR(400 MHz, CDCl₃): δ 1.86(s, 6H); 6.90-7.02(m, 4H); 7.10-7.13(m, 2H); 7.27(d, J = 8.0 Hz, 2H); 7.43(tr, J = 8.0 Hz, 4H); 7.83(s, 2H); 7.89(d, J = 8.0 Hz, 2H). |
| | Yield: 61%, ¹H NMR(400 MHz, CDCl₃): δ 1.94(s, 6H); 3.15(s, 6H); 7.11(d, J = 8.4 Hz, 2H); 7.30(tr, J = 7.6 Hz, 2H); 7.47(tr, J = 7.6 Hz, 2H); 7.70(d, J = 8.0 Hz, 4H); 7.85(s, 2H); 7.92(d, J = 8.0 Hz, 4H); 8.05(d, J = 8.0 Hz, 4H). |

TABLE 11
| Compound 31' | Yield and NMR spectrum data |
|---|---|
| 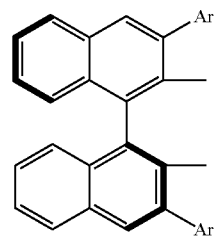 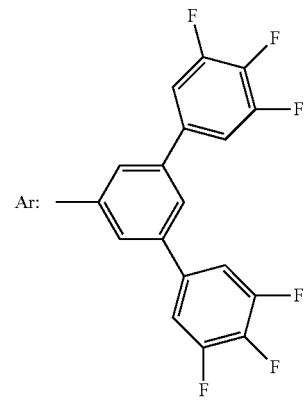 | Yield: 42%, ¹H NMR(400 MHz, CDCl₃) δ 1.94 (s, 6H); 6.88-6.91(m, 2H); 6.88-6.91(m, 2H); 7.08(d, J = 4.2 Hz, 4H); 7.16(d, J = 8.4 Hz, 2H); 7.32(tr, J = 7.6 Hz, 2H); 7.37(s, 8H); 7.50(tr, J = 7.6 Hz, 2H); 7.90(s, 2H); 7.95(d, J = 8.4 Hz, 2H). |
| 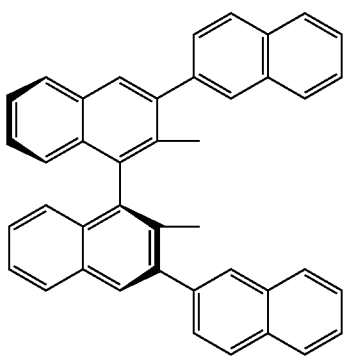 | Yield: 70%, ¹H NMR(400 MHz, CDCl₃) δ 2.02 (s, 6H); 7.19(d, J = 8.8 Hz, 2H); 7.27-7.31(m, 2H); 7.43-7.47(m, 2H); 7.50-7.54(m, 4H); 7.62 (dd, J = 8.4 Hz, 2.0 Hz); 7.90-7.97(m, 4H). |
| 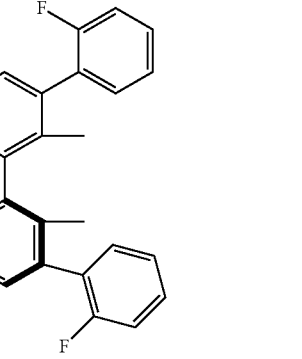 | Yield: 83%, ¹H NMR(400 MHz, CDCl₃) δ 1.92 (s, 6H); 7.16-7.20(m, 4H); 7.26-7.28(m, 4H); 7.32-7.49(m, 6H); 7.88(s, 2H), 7.91(d, J = 8.0 Hz, 2H). |
| 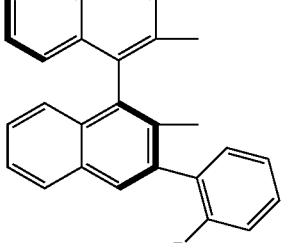 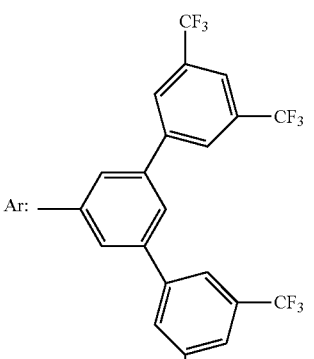 | Yield: 73%, ¹H NMR(400 MHz, CDCl₃) δ 2.05 (s, 6H); 7.18(d, J = 8.4 Hz, 2H); 7.31-7.35(m, 4H); 7.47-7.51(m, 2H); 7.77(dd, J = 4.4 Hz, 1.6 Hz, 4H); 7.93(s, 4H); 7.95(s, 2H); 7.97(s, 2H); 8.11(s, 8H). |

TABLE 12

| Compound 32' | Yield and NMR spectrum data |
|---|---|
| (structure with two biphenyl substituents and two CH₂Br groups on binaphthyl core) | Yield: 86%, $^1$H NMR(400 MHz, CDCl$_3$) δ 4.36(s, 4H); 7.30(d, J = 8.0 Hz, 2H); 7.32(tr, J = 8.0 Hz, 2H); 7.38(tr, J = 8.0 Hz, 2H); 7.48-7.55(m, 6H); 7.69-7.76(m, 12H); 7.95(tr, J = 8.0 Hz, 4H). |
| (structure with two 4-NO₂-phenyl substituents and two CH₂Br groups on binaphthyl core) | Yield: 81%, $^1$H NMR(400 MHz, CDCl$_3$) δ 2.04(s, 6H); 4.20(s, 4H); 7.17(d, J = 8.0 Hz, 2H); 7.35-7.36(m, 2H); 7.58(tr, J = 4.0 Hz, 2H); 7.81(dd, J = 6.8 Hz, 1.6 Hz, 4H); 7.93(s, 2H); 7.96(d, J = 8.0 Hz, 2H); 8.37(d, J = 8.0 Hz, 4H). |
| (structure with two 4-CN-phenyl substituents and two CH₂Br groups on binaphthyl core) | Yield: 84%, $^1$H NMR(400 MHz, CDCl$_3$) δ 4.18(s, 4H); 7.15(d, J = 8.8 Hz, 2H); 7.32-7.36(m, 2H); 7.56(tr, J = 8.8 Hz, 2H); 7.74(d, J = 8.0 Hz, 4H); 7.80(d, J = 8.0 Hz, 4H); 7.89(s, 2H); 7.94(d, J = 8.0 Hz, 2H). |
| (structure with two benzodioxole substituents and two CH₂Br groups on binaphthyl core) | Yield: 71%, $^1$H NMR(400 MHz, CDCl$_3$) δ 4.28(s, 4H); 6.92(d, J = 8.4 Hz, 2H); 7.06(d, J = 8.0 Hz, 2H); 7.11(s, 2H); 7.13(d, J = 8.4 Hz, 2H); 7.28(d, J = 7.6 Hz, 2H); 7.51(tr, J = 8.4 Hz, 2H); 7.87(s, 2H); 7.89(d, J = 8.4 Hz, 2H). |

TABLE 13

| Compound 32' | Yield and NMR spectrum data |
|---|---|
| (structure with 3,4-dichlorophenyl groups) | Yield: 84%, ¹H NMR(400 MHz, CDCl$_3$) δ 4.19(s, 4H); 7.13(d, J = 8.4 Hz, 2H); 7.32(tr, J = 7.6 Hz, 2H); 7.47(dd, J = 8.4 Hz, 2 Hz, 2H); 7.53-7.58(m, 4H); 7.88(s, 2H); 7.92(d, J = 8.4 Hz, 2H). |
| (structure with benzothiophene groups) | Yield: 67%, ¹H NMR(400 MHz, CDCl$_3$) δ 4.48(s, 4H); 7.17(d, J = 8.4 Hz, 2H); 7.31-7.43(m, 6H); 7.52-7.57 (m, 2H); 7.70(s, 2H); 7.85-7.90(m, 4H); 7.94(d, J = 8.4 Hz, 2H); 8.19(s, 2H). |
| (structure with 3,5-difluorophenyl groups) | Yield: 89%, ¹H NMR(400 MHz, CDCl$_3$) δ 4.20(d, J = 10 Hz, 2H); 4.23(d, J = 10 Hz, 2H); 6.87-6.93(m, 2H); 7.13-7.18(m, 6H); 7.32(tr, J = 8.0 Hz, 2H); 7.54(tr, J = 8.0 Hz, 2H); 7.90(s, 2H); 7.92(d, J = 8.4 Hz, 2H). |
| (structure with 3-methoxyphenyl groups) | Yield: 84%, ¹H NMR(400 MHz, CDCl$_3$) δ 3.87(s, 6H); 4.29(s, 4H); 6.97-7.00(m, 2H); 7.15-7.21(m, 6H); 7.27-7.31(m, 2H); 7.39(tr, J = 8.4 Hz, 2H); 7.49-7.53 (m, 2H); 7.91(d, J = 8.4 Hz, 2H); 7.92(s, 2H). |

TABLE 13-continued

| Compound 32' | Yield and NMR spectrum data |
| --- | --- |
| [structure: binaphthyl with two CH₂Br groups and two 3-hydroxyphenyl substituents] | Yield: 81%, ¹H NMR(400 MHz, CDCl₃) δ 4.27(s, 4H); 6.90-6.93(m, 2H); 7.10-7.17(m, 6H); 7.25-7.29(m, 2H); 7.34(tr, J = 8.0 Hz, 2H); 7.48-7.52(m, 2H); 7.89(d, J = 8.0 Hz, 2H); 7.90(s, 2H). |

TABLE 14

| Compound 32' | Yield and NMR spectrum data |
| --- | --- |
| [structure: binaphthyl with two CH₂Br groups and two 3-(trifluoromethyl)phenyl substituents] | Yield: 80%, ¹H NMR(400 MHz, CDCl₃) δ 4.12(s, 4H); 7.10(d, J = 8.4 Hz, 2H); 7.24-7.28(m, 2H); 7.48(tr, J = 7.2 Hz, 2H); 7.55(tr, J = 8.0 Hz, 2H); 7.64(d, J = 8.0 Hz, 2H); 7.76(d, J = 8.0 Hz, 2H); 7.83-7.87(m, 6H). |
| [structure: binaphthyl with two CH₂Br groups and two 4-(trifluoromethyl)phenyl substituents] | Yield: 85%, ¹H NMR(400 MHz, CDCl₃) δ 4.22(s, 4H); 7.17(d, J = 8.0 Hz, 2H); 7.31-7.35(m, 2H); 7.53-7.57(m, 2H), 7.76(tr, J = 6.4 Hz, 8H), 7.91(s, 2H); 7.93(d, J = 8.0 Hz, 2H). |
| [structure: binaphthyl with two CH₂Br groups and two 2,4-difluorophenyl substituents] | Not determined |

TABLE 14-continued

| Compound 32' | Yield and NMR spectrum data |
|---|---|
| (structure with two CH₂Br groups, phenyl sulfonyl and methylsulfonyl substituents on binaphthyl) | Yield: 83%, ¹H NMR(400 MHz, CDCl₃) δ 3.16(s, 6H); 4.20(s, 4H); 7.17(d, J = 8.4 Hz, 2H); 7.33-7.37(m, 2H); 7.57(tr, J = 7.6 Hz, 2H); 7.85(d, J = 8.4 Hz, 4H); 7.91(s, 2H); 7.95(d, J = 8.4 Hz, 2H); 8.09(d, J = 8.4 Hz, 4H). |

TABLE 15

| Compound 32' | Yield and NMR spectrum data |
|---|---|
| (binaphthyl structure with Ar groups; Ar = 3,5-bis(3,4,5-trifluorophenyl)phenyl) | not determined |
| 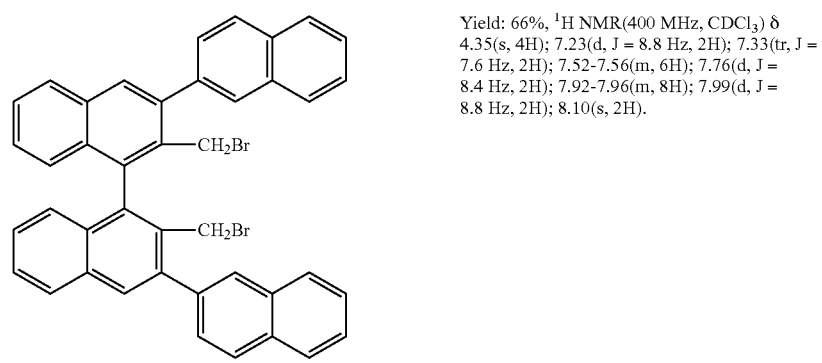 | Yield: 66%, ¹H NMR(400 MHz, CDCl₃) δ 4.35(s, 4H); 7.23(d, J = 8.8 Hz, 2H); 7.33(tr, J = 7.6 Hz, 2H); 7.52-7.56(m, 6H); 7.76(d, J = 8.4 Hz, 2H); 7.92-7.96(m, 8H); 7.99(d, J = 8.8 Hz, 2H); 8.10(s, 2H). |

TABLE 15-continued

| Compound 32' | Yield and NMR spectrum data |
|---|---|
| (structure with F-phenyl, naphthyl-CH₂Br groups) | Not determined |
| (structure with Ar groups, CH₂Br, naphthyl) Ar: (3,5-bis(CF₃)phenyl-substituted biphenyl) | Yield: 81%, $^1$H NMR(400 MHz, CDCl$_3$) δ 4.32(d, J = 10.0 Hz, 2H); 3.56(d, J = 10.0 Hz, 2H); 7.24(d, J = 8.4 Hz, 2H); 7.37-7.41(m, 2H); 7.58-7.62(m, 2H); 7.88(tr, J = 5.6 Hz, 2H); 7.94(s, 4H); 8.00(d, J = 1.6 Hz, 6H); 8.06(s, 2H); 8.17(s, 8H). |

Reference Example 17

Synthesis (2) of Starting Material (Compound 33') for Synthesizing Quaternary Ammonium Salt

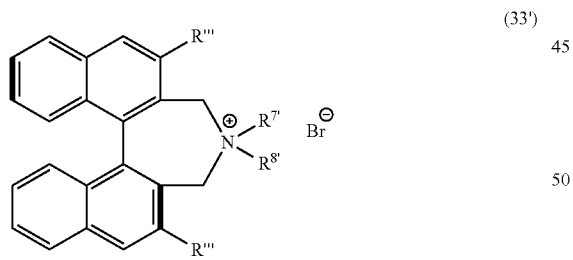

(33')

The same procedure as in Example 1 was performed except that the compounds 32' (S-form) obtained in Reference Example 6 were used and dibutylamine as used in Example 1 was used. The product were purified by silica gel column chromatography to give compounds 33' respectively in good yields. The R-form can be prepared in the same procedure.

The specific structural formulae and the NMR spectrum data of the obtained compounds 33' are shown in Tables 16 to 19.

TABLE 16

| Compound 33' | Yield and NMR spectrum data |
|---|---|
| (structure with biphenyl substituents) | Yield: 81%, ¹H NMR(400 MHz, CDCl$_3$) δ 0.26(br, 2H); 0.82(tr, J = 7.2 Hz, 6H); 0.84-1.64(m, 6H); 2.62(tr, J = 13.2 Hz, 2H); 3.12(d, J = 13.2 Hz, 2H); 3.69(d, J = 14.0 Hz, 2H); 5.18(d, J = 14.0 Hz, 2H); 7.35-7.40(m, 6H); 7.46(tr, J = 8.0 Hz, 4H); 7.63-7.69(m, 10H); 7.84(m, 4H); 8.05(d, J = 8.0 Hz, 2H); 8.14(s, 2H). |
| (structure with 4-NO$_2$-phenyl substituents) | Yield: 52%, ¹H NMR(400 MHz, CDCl$_3$) δ 0.15-0.22(m, 2H); 0.60(tr, J = 7.2 Hz, 6H); 0.87-1.01(m, 6H); 2.55-2.63(m, 2H); 3.25(tr, J = 13.2 Hz, 2H); 3.80(d, J = 14.0 Hz, 2H); 5.05(d, J = 14.0 Hz, 2H); 7.37(d, J = 8.8 Hz, 2H); 7.45(tr, J = 7.6 Hz, 2H); 7.70(tr, J = 7.6 Hz, 2H); 7.85(d, J = 8.8 Hz, 2H); 8.08(d, J = 8.4 Hz, 2H); 8.12(s, 2H); 8.46(d, J = 8.4 Hz, 4H). |
| (structure with 4-CN-phenyl substituents) | Yield: 78%, ¹H NMR(400 MHz, CDCl$_3$) δ 0.17-0.19(m, 2H), 0.66(tr, J = 7.2 Hz, 6H); 0.84-0.87(m, 2H); 0.94-1.00(m, 4H); 2.52(tr, J = 8.4 Hz, 2H); 3.23(tr, J = 12.4 Hz, 2H); 3.73(d, J = 14.4 Hz, 2H); 5.03(d, J = 14.4 Hz, 2H); 7.34(d, J = 8.4 Hz, 2H); 7.40-7.44(m, 2H); 7.68(tr, J = 7.2 Hz, 2H); 7.78(d, J = 8.0 Hz, 4H); 7.89(d, J = 8.0 Hz, 4H); 8.06(d, J = 8.0 Hz, 2H); 8.09 (s, 2H). |
| (structure with benzodioxole substituents) | Yield: 86%, ¹H NMR(400 MHz, CDCl$_3$) δ 0.42(b, 2H); 0.74(tr, J = 6.8 Hz, 6H); 0.98-1.07(m, 6H); 2.60-2.63 (m, 2H); 3.16-3.18(m, 2H); 3.57-3.60(m, 2H); 5.23-5.29(m, 2H); 6.05(d, J = 12.0 Hz, 4H); 7.04-7.06 (m, 6H); 7.32-7.38(m, 4H); 7.62(d, J = 7.6 Hz, 2H); 8.00(tr, J = 8.0 Hz, 2H); 8.04(s, 2H). |

TABLE 17

| Compound 33' | Yield and NMR spectrum data |
|---|---|
| (3,4-dichlorophenyl substituted binaphthyl azepinium bromide structure) | Yield: 65%, $^1$H NMR (400 MHz, CDCl$_3$) δ 0.23 (br, 2H); 0.69 (tr, J = 7.2 Hz, 6H); 0.89-1.02 (m, 6H); 2.56 (br, 2H); 3.19 (br, 2H); 3.59-3.65 (m, 2H); 5.05 br, 2H); 7.28-7.41 (m, 4H); 7.54-7.70 (m, 8H); 8.25-8.11 (m, 4H). |
| (benzothiophene substituted binaphthyl azepinium bromide structure) | Yield: 76%, $^1$H NMR (400 MHz, CDCl$_3$) δ 0.19 (tr, J = 7.2 Hz, 6H); 0.79-0.96 (m, 8H); 2.73-2.74 (m, 2H); 3.22 (tr, J = 16.0 Hz, 2H); 3.70 (d, J = 14.0 Hz, 2H); 5.60 (d, J = 14.0 Hz, 2H); 7.33-7.43 (m, 8H); 7.66 (tr, J = 8.0 Hz, 2H); 7.86 (d, J = 7.6 Hz, 4H); 8.05(d, J = 8.4 Hz, 4H); 8.30 (s, 2H). |
| (3,5-difluorophenyl substituted binaphthyl azepinium bromide structure) | Yield: 62%, $^1$H NMR (400 MHz, CDCl$_3$) δ 0.32-0.34 (m, 2H); 0.71 (tr, J = 7.2 Hz, 6H); 0.99-1.09 (m, 6H); 3.27 (tr, J = 12.8 Hz, 2H); 3.73 (d, J = 14.4 Hz, 2H); 5.00(d, J = 14.4 Hz, 2H); 6.90 (tr, J = 8.8 Hz, 2H); 7.05-7.23 (m, 4H); 7.23-7.39 (m, 4H); 7.62 (tr, J = 8.4 Hz, 2H); 8.02 (d, J = 8.4 Hz, 2H); 8.04 (s, 2H). |
| (3-methoxyphenyl substituted binaphthyl azepinium bromide structure) | Yield: 79%, $^1$H NMR (400 MHz, CDCl$_3$) δ 0.20 (b, 2H); 0.65 (tr, J = 7.2 Hz, 6H); 0.93-1.04 (m, 6H); 2.62-2.64 (tr, J = 13.2 Hz, 2H); 3.06 (tr, J = 13.2 Hz, 2H); 3.64 (m, 2H); 3.91 (s, 6H); 5.08 (m, 2H); 7.02 (d, J = 8.0 Hz, 2H); 7.18-7.20 (m, 2H); 7.38 (d, J = 4 Hz, 4H); 7.49-7.50 (m, 2H); 7.62-7.66 (m, 2H); 8.03 (d, J = 8.4 Hz, 2H); 8.08 (s, 2H). |

TABLE 17-continued

| Compound 33' | Yield and NMR spectrum data |
|---|---|
| (structure: binaphthyl azepinium with two 3-hydroxyphenyl groups, dibutyl N+, Br−) | Yield: 89%, $^1$H NMR (400 MHz, CDCl$_3$) δ 0.27 (br, 2H); 0.62 (tr, J = 7.2 Hz, 6H); 0.80-0.85 (br, 6H); 2.48 (br, 2H); 2.94 (br, 2H); 3.51 (br, 2H); 5.30 (br, 2H); 6.92-6.99 (br, 4H); 7.24-7.32 (m, 8H); 7.52 (br, 2H); 7.98 (d, J = 8.4 Hz, 2H); 8.04 (s, 2H); 8.47 (br, 2H). |

TABLE 18

| Compound 33' | Yield and NMR spectrum data |
|---|---|
| (structure: binaphthyl azepinium with two 3-CF$_3$-phenyl groups, dibutyl N+, Br−) | Yield: 62%, $^1$H NMR (400 MHz, CDCl$_3$) δ 0.15 (b, 2H); 0.60 (tr, J = 7.2 Hz, 6H); 0.72-0.98 (m, 6H); 2.59 (tr, J = 13.2 Hz, 2H); 3.15 (tr, J = 13.2 Hz, 2H), 3.75 (d, J = 14.0 Hz, 2H); 5.04 (d, J = 14.0 Hz, 2H); 7.36-7.44 (m, 4H); 7.67 (tr, J = 7.6 Hz, 2H); 7.77-7.79 (m, 4H); 7.87 (d, J = 7.6 Hz, 4H); 8.03-8.13 (m, 4H). |
| (structure: binaphthyl azepinium with two 4-CF$_3$-phenyl groups, dibutyl N+, Br−) | Yield: 71%, $^1$H NMR (400 MHz, CDCl$_3$) δ 0.15 (br, 2H); 0.61 (tr, J = 7.2 Hz, 6H); 0.74-0.98 (m, 6H); 3.20 (tr, J = 12.8 Hz, 2H); 3.75 (d, J = 14.0 Hz, 2H); 5.09 (d, J = 14.0 Hz, 2H); 7.36 (d, J = 8.4 Hz, 2H); 7.42 (tr, J = 7.2 Hz, 2H); 7.68 (tr, J = 7.2 Hz, 2H); 7.78 (d, J = 8.0 Hz, 4H); 7.88 (d, J = 8.0 Hz, 4H); 8.06 (d, J = 8.0 Hz, 2H). |

TABLE 18-continued

| Compound 33' | Yield and NMR spectrum data |
|---|---|
| 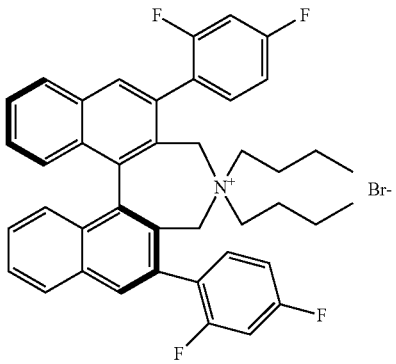 | Yield: 73% ¹H NMR (400 MHz, CDCl₃) δ 0.35 (br, 2H); 0.72 (tr, J = 7.2 Hz, 6H); 0.89-1.08 (m, 6H); 2.65-2.69 (m, 2H); 3.20 (tr, J = 12.8 Hz, 2H); 3.75 (d, J = 14.0 Hz, 2H); 4.97 (d, J = 14.0 Hz, 2H); 6.91-6.99 (m, 2H); 7.16 (br, 4H); 7.32-7.41 (m, 4H); 7.64 (tr, J = 7.6 Hz, 2H); 8.03 (d, J = 8.0 Hz, 2H); 8.11 (d, J = 8.0 Hz, 2H). |
| 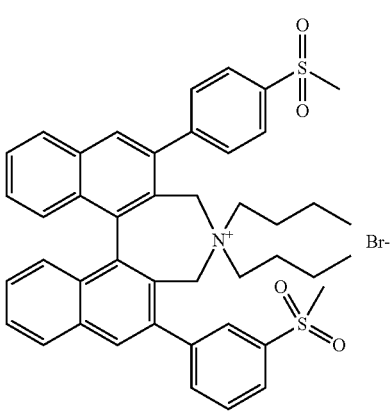 [SMILES: CCCC[N+]1(CCCC)Cc2c(-c3ccc(S(C)(=O)=O)cc3)cc3ccccc3c2-c2c(c(-c3cccc(S(C)(=O)=O)c3)cc3ccccc23)C1 ; [Br-]] | Yield: 75%, ¹H NMR (400 MHz, CDCl₃) δ 0.24 (br, 2H); 0.88 (tr, J = 7.2 Hz, 6H); 1.24-1.43 (m, 6H); 2.56 (tr, J = 13.2 Hz, 2H); 3.28 (tr, J = 13.2 Hz, 2H); 3.72 (d, J = 14.0 Hz, 2H); 4.97 (d, J = 14.0 Hz, 2H); 7.39 (d, J = 8.4 Hz, 2H); 7.46 (tr, J = 7.6 Hz, 2H); 7.70 (tr, J = 7.6 Hz, 2H); 7.79 (br, 4H); 8.08 (d, J = 8.4 Hz, 2H); 8.11 (s, 2H); 8.20 (d, J = 8.4 Hz, 4H). |

TABLE 19

| Compound 33' | Yield and NMR spectrum data |
|---|---|
| 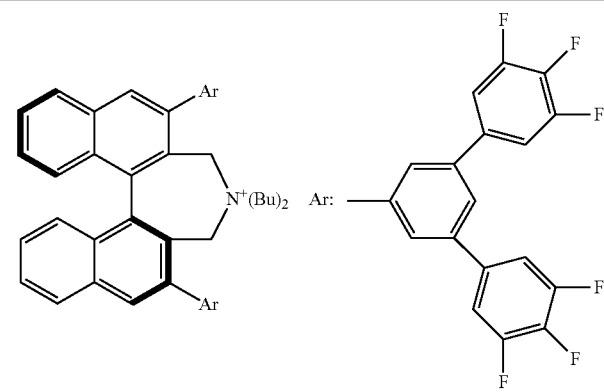 | Yield: 61%, ¹H NMR (400 MHz, CDCl₃) δ 0.39-0.41 (m, 2H); 0.49 (tr; J = 7.2 Hz, 6H); 0.90-1.01 (m, 6H); 2.75-2.80 (m, 2H); 3.29 (tr, J = 12.8 Hz, 2H); 3.89 (d, J = 14.0 Hz, 2H); 5.09 (d, J = 14.0 Hz, 2H); 7.35-7.47 (m, 12H); 7.63(s, 2H); 7.67-7.70 (m, 2H); 7.78 (d, J = 8.8 Hz, 2H); 8.00 (s, 2H); 8.08 (d, J = 8.0 Hz, 2H); 8.15 (s, 2H). |

TABLE 19-continued

| Compound 33' | Yield and NMR spectrum data |
|---|---|
| | Yield: 74%, ¹H NMR (400 MHz, CDCl₃) δ −0.21 (br, 4H); 0.46-0.96 (m, 10H); 2.62 (tr; J = 13.2 Hz, 2H); 3.00 (tr, J = 13.2 Hz, 2H); 7.75 (d, J = 14.0 Hz, 2H); 5.08 (br, 2H); 7.38-7.42 (m, 4H); 7.53-7.59 (m, 4H); 7.65-7.69 (m, 4H); 7.92 (d, J = 6.8 Hz, 4H); 8.07-8.09 (m, 6H); 8.21 (s, 2H). |
| | Yield: 45%, ¹H NMR (400 MHz, CDCl₃) δ 0.42 (b, 2H); 0.71 (tr, J = 7.2 Hz, 6H); 2.62-2.69 (m, 2H); 3.87-3.91 (m, 2H); 4.27 (d, J = 14.0 Hz, 2H); 5.28 (d, J = 14.0 Hz, 2H); 7.22 (d, J = 8.4 Hz, 2H); 7.37-7.42 (m, 6H); 7.55 (tr, J = 7.6 Hz, 2H); 7.64-7.67 (m, 2H); 7.76 (tr, J = 7.6 Hz, 2H); 8.07 (d, J = 8.4 Hz, 2H); 8.16 (s, 2H). |
| | Yield: 93%, ¹H NMR (400 MHz, CDCl₃) δ 0.52 (tr, J = 7.2 Hz, 6H); 0.81-0.94 (m, 8H); 2.82 (tr, J = 13.6 Hz, 2H); 3.31 (tr, 13.6 Hz, 2H); 3.94 (d, J = 14.0 Hz, 2H); 5.07 (d, J = 14.0 Hz, 2H); 7.47 (d, J = 3.6 Hz, 4H); 7.69-7.74 (m, 2H); 7.75 (s, 2H); 7.91(d, J = 3.6 Hz, 2H); 7.92 (d, J = 1.6 Hz, 2H); 8.05 (s, 2H); 8.12 (s, 2H); 8.14-8.17 (m, 8H); 8.20 (s, 2H). |

Example 18

Examination (1) of Effect of Substituent of Phase-Transfer Catalyst

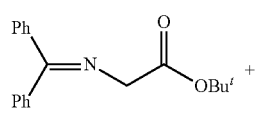

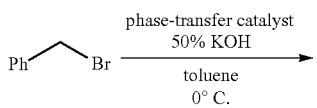

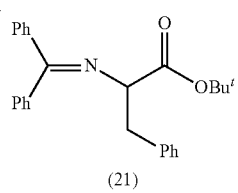

(21)

According to Example 11, α-benzylation was performed at 0° C., using 3 mol % of phase-transfer catalysts described Tables 20 to 22 below. The results are shown in Tables 20 to 22.

TABLE 20
Phase-transfer catalyst:
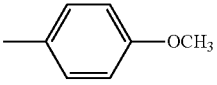
| Ar | Ar' | Reaction time (hr) | Yield (%) | Optical purity (% ee) |
|---|---|---|---|---|
| 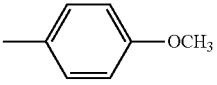 | 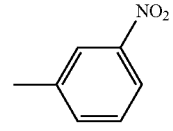 | 1.5 | 65 | 65 |
| 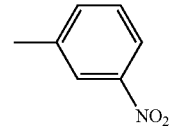 | 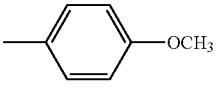 | 1.5 | 88 | 87 |
| 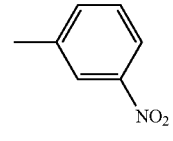 | 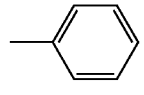 | 2 | 65 | 80 |
| 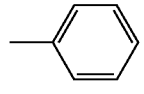 | 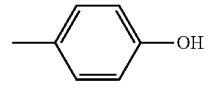 | 24 | 86 | 58 |
| 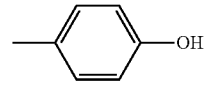 | 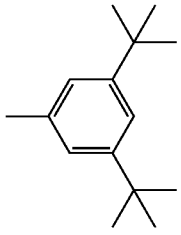 | 1 | 70 | 64 |
| 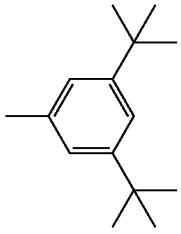 | | 4 | 87 | 66 |

TABLE 21

Phase-transfer catalyst:

(structure: binaphthyl-based quaternary ammonium bromide with two Ar groups and N,N-dibutyl)

| Ar | Reaction time (hr) | Yield (%) | Optical purity (% ee) |
|---|---|---|---|
| 4-F-C6H4 | 7 | 92 | 82 |
| 4-Cl-C6H4 | 7 | 93 | 83 |
| 3-F-C6H4 | 2 | 97 | 77 |
| 3-Cl-C6H4 | 4 | 94 | 75 |
| 3,4,5-F3-C6H2 | 21 | 86 | 97 |
| 3,4,5-Cl3-C6H2 | 3 | 62 | 93 |
| 3,4-F2-C6H3 | 5 | 97 | 91 |
| 4-OCH3-C6H4 | 3 | 85 | 71 |
| 3-NO2-C6H4 | 3 | 89 | 89 |

TABLE 22

Phase-transfer catalyst:

(structure: binaphthyl-based quaternary ammonium bromide with two 3,4,5-trifluorophenyl groups and N,R,R')

| NR R' group | Reaction time (hr) | Yield (%) | Optical purity (% ee) |
|---|---|---|---|
| N(CH3)2(CH2CH2OCH3)2 | 7 | 98 | 93 |
| N(CH3)2(CH2CH2OH)2 | 1 | 78 | 81 |
| N-methyl-N'-phenylpiperazinium | 2 | 55 | 78 |

Example 19

Examination (2) of Effect of Substituent of Phase-Transfer Catalyst

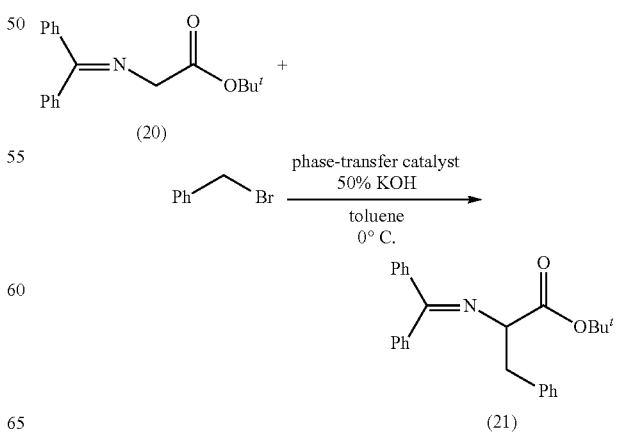

(20)

phase-transfer catalyst
50% KOH
─────────────
toluene
0° C.

(21)

According to Example 11, α-benzylation was performed at 0° C., using 3 mol % of phase-transfer catalysts described Tables 23 to 26 below. The results are shown in Tables 23 to 26.

TABLE 23

| Phase-transfer catalyst | Reaction time (hr) | Yield (%) | Optical purity (% ee) |
|---|---|---|---|
| (4-biphenyl substituted catalyst) | 3 | 78 | 68.7 |
| (4-NO₂ substituted catalyst) | 3 | 88.7 | 92.2 |
| (4-CN substituted catalyst) | 3 | 91 | 93.8 |
| (methylenedioxy substituted catalyst) | 3 | 86 | 74.5 |

TABLE 24

| Phase-transfer catalyst | Reaction time (hr) | Yield (%) | Optical purity (% ee) |
|---|---|---|---|
| (3,4-diCl substituted catalyst) | 3 | 91 | 86.9 |
| (benzothiophene substituted catalyst) | 3 | 71 | 90 |
| (3,5-diF substituted catalyst) | 3 | 94 | 92.8 |
| (3-OMe substituted catalyst) | 3 | 52 | 73.4 |

TABLE 24-continued

| Phase-transfer catalyst | Reaction time (hr) | Yield (%) | Optical purity (% ee) |
|---|---|---|---|
| [structure with two 3-hydroxyphenyl groups] | 3 | 85 | 77.8 |

TABLE 25

| Phase-transfer catalyst | Reaction time (hr) | Yield (%) | Optical purity (% ee) |
|---|---|---|---|
| [structure with two 3-CF$_3$-phenyl groups] | 3 | 89 | 82.8 |
| [structure with two 4-CF$_3$-phenyl groups] | 3 | 89 | 90.5 |

TABLE 25-continued

| Phase-transfer catalyst | Reaction time (hr) | Yield (%) | Optical purity (% ee) |
|---|---|---|---|
| [structure with two 2,4-difluorophenyl groups] | 3 | 89.8 | 91 |
| [structure with two methylsulfonylphenyl groups] | 3 | 83 | 90 |

TABLE 26

| Phase-transfer catalyst | Reaction time (hr) | Yield (%) | Optical purity (% ee) |
|---|---|---|---|
| [structure: binaphthyl N+(Bu)2 with Ar = 3,4,5-trifluoro-3',4',5'-trifluoro-terphenyl] | 3 | 76.5 | 81.05 |
| [structure: binaphthyl bearing two 2-naphthyl groups, N+Bu2 Br-] | 3 | 60 | 77.2 |
| [structure: binaphthyl bearing two 2-fluorophenyl groups, N+Bu2 Br-] | 3 | 92 | 61.6 |
| [structure: binaphthyl N+(Bu)2 with Ar = 3,5-bis(trifluoromethyl)-3',5'-bis(trifluoromethyl)-terphenyl] | 3 | 77 | 81.4 |

Example 20

Examination of Effect of Stirring

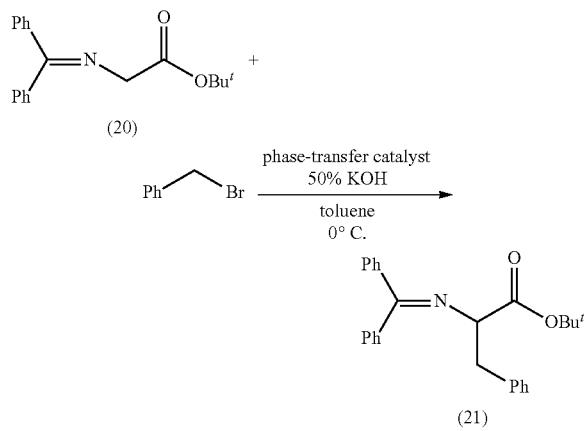

According to Example 11, benzylation was performed at 0° C. for one hour, by using 3 mol % of the compound 16 (S-form) as a phase-transfer catalyst under stirring with a stronger stirrer. In spite of only one hour reaction, the yield based on the HPLC analysis of the reaction mixture was 78% and after purification on a silica gel column the yield was 72%, and the optical purity was 99% ee. The reaction time is much shorter and the yields are higher than the results shown in Table 1, which indicates that stronger stirring provides much better reaction efficiency.

Example 21

Benzylation (1) of Alanine

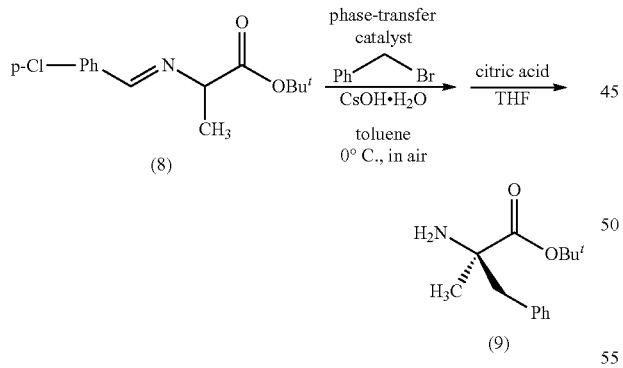

To a mixture of alanine tert-butyl ester-p-chlorobenzyl Schiff base (compound 8) (134 mg, 0.5 mmol), phase-transfer catalysts described in Table 27 below (3 mol %), and benzyl bromide (1.2 equivalents) in 2 mL of toluene, cesium hydroxide·monohydrate (5 equivalents) was added at 0° C., and the mixture was stirred under an air atmosphere at 0° C. for 30 min (first process). The reaction mixture was poured into water and extracted with dichloromethane, and the solvent was removed, and the residue was dissolved in 5 mL of tetrahydrofuran. Then, 5 mL of 0.5 M citric acid aqueous solution was added thereto and the mixture was stirred at room temperature for one hour (second process). The aqueous layer was washed with ether and alkalized with sodium hydrogencarbonate, and then extracted with dichloromethane. The organic layer was dried over sodium sulfate and concentrated to give an oily product. The obtained oily product was subjected to silica gel column chromatography (eluent: ethyl acetate/hexane=2/1) to give a benzylated product of alanine (compound 9). The optical purity of the obtained product was analyzed by HPLC [Daicel Chiralcel AD; eluent: hexane/isopropanol=30:1, 0.5 mL/min; retention time: (R)-form=12.9 min, (S)-form=20.5 min]. The yield and the optical purity are shown in Table 27.

TABLE 27

| Phase-transfer catalyst | Yield (%) | Optical purity (% ee) |
|---|---|---|
| (PhF₃, Br⁻, N⁺(CH₃)₂ binaphthyl) | 58 | 63 |
| (PhF₃, Br⁻, N⁺(Bu)₂ binaphthyl) | 76 | 97 |
| (PhF₃, Br⁻, N⁺(iso-Bu)₂ binaphthyl) | 65 | 54 |
| (PhF₃, Br⁻, N⁺(n-C₁₀H₂₁)₂ binaphthyl) | 65 | 95 |
| (PhF₃, Br⁻, N⁺ crown ether binaphthyl) | 72 | 82 |

TABLE 27-continued

| Phase-transfer catalyst | Yield (%) | Optical purity (% ee) |
|---|---|---|
| [binaphthyl-pyrrolidine with PhF₃ groups, Br⁻] | 72 | 49 |
| [binaphthyl-azepane with PhF₃ groups, Br⁻] | 71 | 80 |
| [binaphthyl-N(Bu)₂, Br⁻] | 65 | 95 |
| [binaphthyl-N(Bu)₂ with Ph groups, Br⁻] | 70 | 61 |
| [binaphthyl-N(Bu)₂ with 3,5-(CF₃)₂-C₆H₃ groups, Br⁻] | 70 | 94 |

Example 22

Benzylation (2) of Alanine

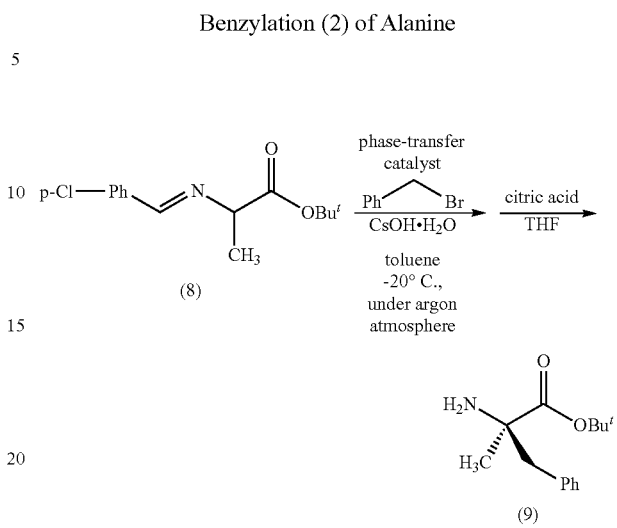

Alanine was benzylated in the same manner as in Example 21, except that the phase-transfer catalyst was used in 1 mol %, the phase-transfer catalysts described in Table 28 below were used, and the reaction condition was changed to −20° C. under an argon atmosphere in the first process. The results are shown in Table 28.

TABLE 28

| Phase-transfer catalyst | Yield (%) | Optical purity (% ee) |
|---|---|---|
| [binaphthyl-N(CH₃)₂ with PhF₃ groups, Br⁻] | 78 | 85 |
| [binaphthyl-N(Bu)₂ with PhF₃ groups, Br⁻] | 85 | 99 |
| [binaphthyl-N(iso-Bu)₂ with PhF₃ groups, Br⁻] | 76 | 73 |

TABLE 28-continued

| Phase-transfer catalyst | Yield (%) | Optical purity (% ee) |
|---|---|---|
| (structure with PhF₃, Br⁻, n-C₁₀H₂₁, n-C₁₀H₂₁) | 78 | 98 |
| (structure with PhF₃, Br⁻, pyrrolidine) | 71 | 67 |
| (structure with PhF₃, Br⁻, azepane) | 85 | 92 |

Example 23

Allylation of Phenylalanine

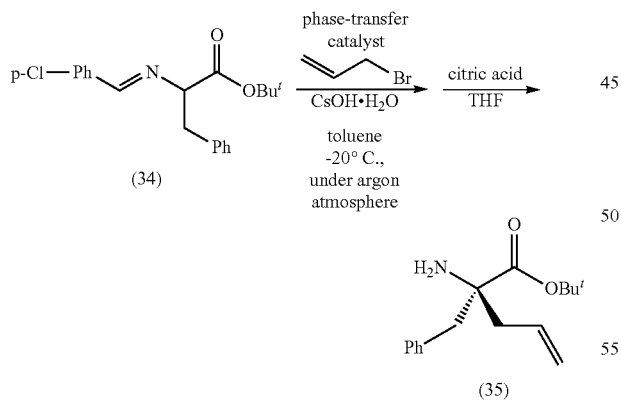

To a mixture of phenylalanine tert-butyl ester-p-chlorobenzyl Schiff base (compound 34) (172 mg, 0.5 mmol), phase-transfer catalysts described in Table 29 below (1 mol %), and allyl bromide (1.2 equivalents) in 2 mL of toluene, cesium hydroxide·monohydrate (5 equivalents) was added at 0° C., and the mixture was stirred under an argon atmosphere at −20° C. for 30 min (first process). The reaction mixture was poured into water and extracted with dichloromethane, and the solvent was removed, and the residue was dissolved in 5 mL of tetrahydrofuran. Then, 5 mL of 0.5 M citric acid aqueous solution was added thereto and stirred at room temperature for one hour (second process). The aqueous layer was washed with ether and alkalized with sodium hydrogencarbonate, and then extracted with dichloromethane. The organic layer was dried over sodium sulfate and concentrated to give an oily product. The obtained oily product was subjected to silica gel column chromatography (eluent: ethyl acetate/hexane=½) to give an allylated product of phenylalanine (compound 35). The optical purity of the obtained product was analyzed by HPLC [Daicel Chiralpak AD; eluent hexane/isopropanol=100:1, 0.5 mL/min; retention time: (R)-form=14.9 min, (S)-form=20.2 min]. The results are shown in Table 29.

TABLE 29

| Phase-transfer catalyst | Yield (%) | Optical purity (% ee) |
|---|---|---|
| (structure with PhF₃, Br⁻, CH₃, CH₃) | 65 | 70 |
| (structure with PhF₃, Br⁻, Bu, Bu) | 76 | 97 |
| (structure with PhF₃, Br⁻, iso-Bu, iso-Bu) | 76 | 74 |
| (structure with PhF₃, Br⁻, n-C₁₀H₂₁, n-C₁₀H₂₁) | 79 | 95 |

TABLE 29-continued

| Phase-transfer catalyst | Yield (%) | Optical purity (% ee) |
|---|---|---|
| 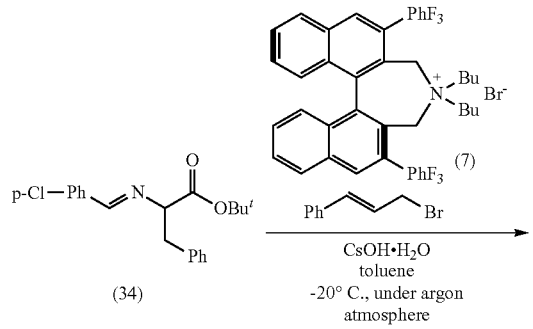 | 72 | 96 |

Example 24

Cinnamylation of Phenylalanine

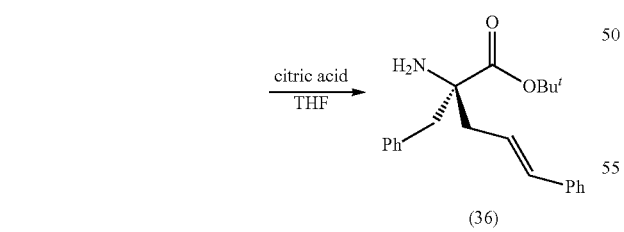

A cinnamylated product of phenylalanine (compound 36) was obtained in the same manner as in Example 23, except that cinnamyl bromide was used instead of allyl bromide and the compound 7 was used as the phase-transfer catalyst in the first process. The optical purity of the obtained product was analyzed by HPLC. The yield was 69%, and the optical purity was 92% ee.

Example 25

Propargylation of Phenylalanine

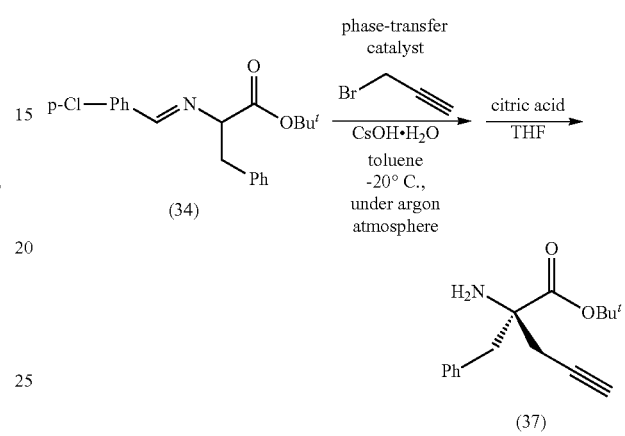

A propargylated product of phenylalanine (compound 37) was obtained in the same manner as in Example 23, except that propargyl bromide was used instead of allyl bromide in the first process. The optical purity of the obtained product was analyzed by HPLC. The results are shown in Table 30.

TABLE 30

| Phase-transfer catalyst | Yield (%) | Optical purity (% ee) |
|---|---|---|
| (structure with PhF₃, CH₃ groups) | 79 | 63 |
| (structure with PhF₃, Bu groups) | 61 | 94 |

TABLE 30-continued

| Phase-transfer catalyst | Yield (%) | Optical purity (% ee) |
|---|---|---|
| (structure with PhF₃, iso-Bu groups) | 67 | 62 |
| (structure with PhF₃, n-C₁₀H₂₁ groups) | 77 | 91 |
| (structure with PhF₃, azepane ring) | 77 | 92 |

Example 26

Tert-Butoxycarbonylmethylation of Phenylalanine

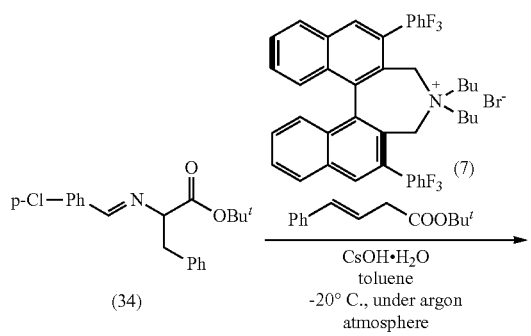

Example 27

Examination of Catalyst Formation and Benzylation in One Vessel

A compound 38 was obtained in the same manner as in Example 23, except that α-bromoacetic acid tert-butyl ester was used instead of allyl bromide and the compound 7 was used as the phase-transfer catalyst in the first process. The optical purity of the obtained product was analyzed by HPLC. The yield was 66%, and the optical purity was 94% ee.

The compound 39 (S-form) described in Table 31 below (3 mol %), secondary amine described in Table 10 below (6 mol %) and potassium carbonate (4.5 mol %) were mixed in dioxane (5 mL), and stirred for 10 hours with heating and reflux. Then, to this reaction mixture, glycine tert-butyl ester benzophenone Schiff base (compound 20) (1 equivalent, 0.5 mmol), 50% potassium hydroxide aqueous solution (1.0 mL), and toluene (3.0 mL) were added, and benzyl bromide (1.2 equivalents) was added dropwise at 0° C. After stirring at 0° C. respectively for a period as described in Table 31 below, the reaction mixture was poured into water, and extracted with ether. The ether extract was washed with saturated brine, dried over sodium sulfate and concentrated under reduced pressure. The oily residue was subjected to silica gel column chromatography (eluted with ether/hexane=1/10) to give (S)-phenylalanine tert-butyl ester benzophenone Schiff base (compound 21). The optical purity of the obtained product was analyzed by HPLC [Daicel Chiralcel OD; eluent: hexane/2-propanol=100:1, 0.5 mL/min; retention time: (R)-form=14.8 min, (S)-form=28.2 min]. The results are shown all together in Table 31.

TABLE 31

| Secondary amine | R = H | R = Ph | R = 3,5-(CF$_3$)$_2$Ph | R = 3,4,5-F$_3$Ph |
|---|---|---|---|---|
| (CH$_3$)$_2$NH | 12% ee (66%, 58 hr) | 26% ee (68%, 5 days) | 1% ee (57%, 30 hr) | 7% ee (44%, 4 days) |
| (C$_4$H$_9$)$_2$NH | −27% ee (53%, 72 hr) | 43% ee (89%, 54 hr) | 70% ee (85%, 48 hr) | 97% ee (76%, 24 hr) |
| (C$_{10}$H$_{21}$)$_2$NH | −17% ee (76%, 90 hr) | 58% ee (86%, 24 hr) | 96% ee (96%, 24 hr) | 97% ee (86%, 72 hr) |
| (iso-C$_4$H$_9$)$_2$NH | −9% ee (52%, 72 hr) | 22% ee (14%, 5 days) | 44% ee (34%, 24 hr) | 7% ee (65%, 4 days) |
| 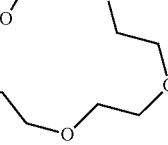 | 1% ee (59%, 72 hr) | 41% ee (86%, 36 hr) | 75% ee (50%, 4 days) | 83% ee (98%, 6 hr) |
| 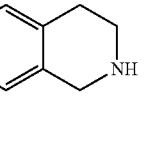 | −19% ee (83%, 36 hr) | −57% ee (71%, 4 days) | 78% ee (33%, 29 hr) | 81% ee (83%, 24 hr) |
| 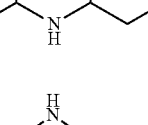 | 22% ee (44%, 51 hr) | 3% ee (72%, 4 days) | 2% ee (10%, 7 days) | 6% ee (13%, 6 days) |
| 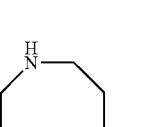 | −7% ee (56%, 4 days) | 5% ee (78%, 24 hr) | 31% ee (24%, 4 days) | 43% ee (80%, 24 hr) |
| 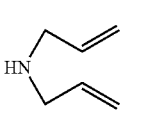 | −23% ee (67%, 48 hr) | 33% ee (82%, 12 hr) | 41% ee (3%, 8 days) | 20% ee (72%, 48 hr) |
| 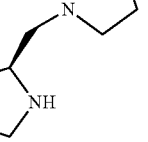 | −8% ee (54%, 24 hr) | n.t. | n.t. | 8% ee (23%, 7 days) |
|  | n.t. | n.t. | n.t. | 10% ee (13%, 6 hr) |

The values in the table show the optical purity (% ee).

The parenthesized values in the table show the yield (%) and the reaction time.

In the optical purity, the values with − show that a product having the opposite configuration was obtained.

The n.t. shows that no experiment was performed.

Thus, it was found that the phase-transfer catalyst can be used for alkylation of α-amino acid derivatives without isolation.

Example 28

α-Benzylation (1) in which the Amount of the Phase-Transfer Catalyst Used is Reduced

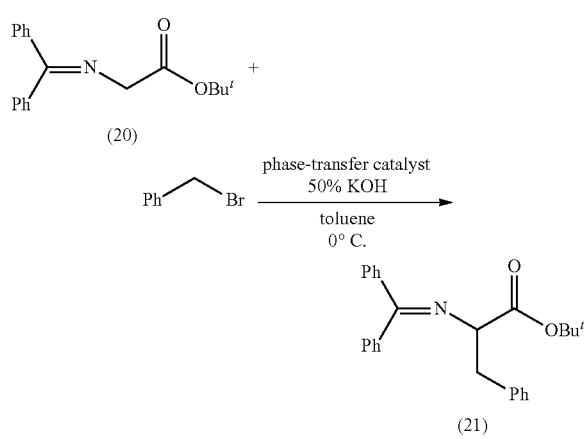

Glycine tert-butyl ester benzophenone Schiff base (compound 20) (88.6 mg, 0.3 mmol), the phase-transfer catalyst (compound 7) obtained in Example 1 in 0.05 mol % to the compound 20, 50% potassium hydroxide aqueous solution (1.0 mL), and toluene (3.0 mL) were mixed, and benzyl bromide (43 μg, 0.36 mmol) was added dropwise at 0° C. After stirring vigorously at 0° C. over 4 hours, the reaction mixture was poured into water, and extracted with ether. The ether extract was washed with saturated brine, dried over sodium sulfate and concentrated under reduced pressure. The oily residue was subjected to silica gel column chromatography (eluted with ether/hexane=1/10) to give (R)-phenylalanine tert-butyl ester benzophenone Schiff base (compound 21). The optical purity of the obtained product was analyzed by HPLC [Daicel Chiralcel OD; eluent hexane/2-propanol=100:1, flow rate: 0.5 mL/min; retention time: (R)-form=14.8 min, (S)-form=28.2 min].

The yield and the optical purity of the obtained compound 21 are shown in Table 32.

Example 29

α-Benzylation (2) in which the Amount of the Phase-Transfer Catalyst Used is Reduced (R)-Phenylalanine tert-butyl ester benzophenone Schiff base (compound 21) was obtained by performing a reaction in the same manner as in Example 28, except that the amount of the phase-transfer catalyst (compound 7) obtained in Example 1 was 0.01 mol % to the compound 20, and that the reaction time was 26 hours. The yield and the optical purity of the obtained compound 21 are shown in Table 32.

Example 30

α-Benzylation (3) in which the Amount of the Phase-Transfer Catalyst Used is Reduced (R)-Phenylalanine tert-butyl ester benzophenone Schiff base (compound 21) was obtained by performing a reaction in the same manner as in Example 28, except that the amount of the phase-transfer catalyst (compound 7) obtained in Example 1 was 0.005 mol % to the compound 20, and that the reaction time was 26 hours. The yield and the optical purity of the obtained compound 21 are shown in Table 32.

Example 31

α-Benzylation (4) in which the Amount of the Phase-Transfer Catalyst Used is Reduced (R)-Phenylalanine tert-butyl ester benzophenone Schiff base (compound 21) was obtained by performing a reaction in the same manner as in Example 28, except that, in addition to the phase-transfer catalyst (compound 7) obtained in Example 1, tetrabutyl ammonium bromide (TBAB) in 0.05 mol % to the compound 20 was added as cocatalyst, and that the reaction time was 1.5 hours. The yield and the optical purity of the obtained compound 21 are shown in Table 32.

Example 32

α-Benzylation (5) in which the Amount of the Phase-Transfer Catalyst Used is Reduced (R)-Phenylalanine tert-butyl ester benzophenone Schiff base (compound 21) was obtained by performing a reaction in the same manner as in Example 28, except that, in addition to the phase-transfer catalyst (compound 7) obtained in Example 1, tetrabutyl ammonium bromide (TBAB) in 0.025 mol % to the compound 20 was added as cocatalyst, and that the reaction time was 1.5 hours. The yield and the optical purity of the obtained compound 21 are shown in Table 32.

Example 33

α-Benzylation (6) in which the Amount of the Phase-Transfer Catalyst Used is Reduced (R)-Phenylalanine tert-butyl ester benzophenone Schiff base (compound 21) was obtained by performing a reaction in the same manner as in Example 28, except that, in addition to the phase-transfer catalyst (compound 7) obtained in Example 1, tetrabutyl ammonium bromide (TBAB) in 0.0167 mol % to the compound 20 was added as cocatalyst, and that the reaction time was 2 hours. The yield and the optical purity of the obtained compound 21 are shown in Table 32.

TABLE 32

| | Amount of the phase-transfer catalyst obtained in Example 1 (mol %) *1 | Amount of TBAB (mol %) *1 | Reaction time (hr) | Yield of compound 21 (%) | Optical purity of compound 21 (% ee) |
|---|---|---|---|---|---|
| Example 28 | 0.05 | no | 4 | 87 | 99 |
| Example 29 | 0.01 | no | 26 | 41 | 97 |
| Example 30 | 0.005 | no | 26 | 29 | 94 |

TABLE 32-continued

| | Amount of the phase-transfer catalyst obtained in Example 1 (mol %) *1 | Amount of TBAB (mol %) *1 | Reaction time (hr) | Yield of compound 21 (%) | Optical purity of compound 21 (% ee) |
|---|---|---|---|---|---|
| Example 31 | 0.05 | 0.05 | 1.5 | 99 | 94 |
| Example 32 | 0.05 | 0.025 | 1.5 | 91 | 95 |
| Example 33 | 0.05 | 0.0167 | 2 | 91 | 96 |

*1 Based on the amount of compound 20

As shown in Table 32, according to the methods described in Examples 28 to 33, (R)-phenylalanine tert-butyl ester benzophenone Schiff base (compound 21) can be produced in an even better optical purity. Furthermore, when TBAB is used in combination as a cocatalyst (Examples 31 to 33), the yield of the optically active compound 21 can be improved, and the reaction time up to achieving this can be also reduced at the same time.

Example 34

Hydrolysis (1) of Tert-Butyl Ester

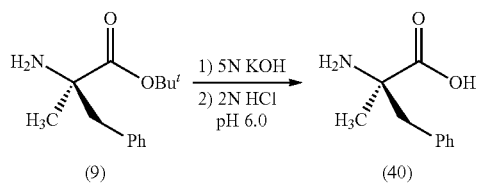

To the benzylated product (compound 9) obtained by either one of Example 2, 21 or 22, a 5N potassium hydroxide aqueous solution (an excessive amount with respect to the compound 9) is added, and the mixture is stirred for one hour until the solution becomes uniform on a water bath at 40° C. to 50° C. After cooling to room temperature, 2N hydrochloric acid is added until the pH reaches 6.0. After confirming the production of precipitate, the solution is stirred under ice cooling for 30 min. The precipitate is filtered and washed with ethanol (appropriate amount). The crystals are dried at 50° C. overnight to give the compound 40 in a good yield and optical purity.

Example 35

Hydrolysis (2) of Tert-Butyl Ester

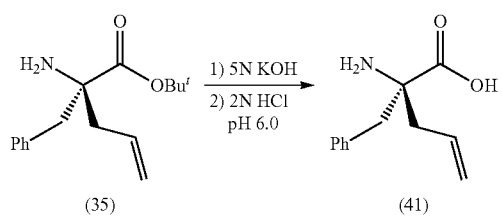

The compound 41 is obtained in a good yield and optical purity in the same manner as in Example 34, except that the allylated product (compound 35) obtained in Example 23 is used instead of the benzylated product (compound 9) obtained by either one of Example 2, 21 or 22.

Example 36

Hydrolysis (3) of Tert-Butyl Ester

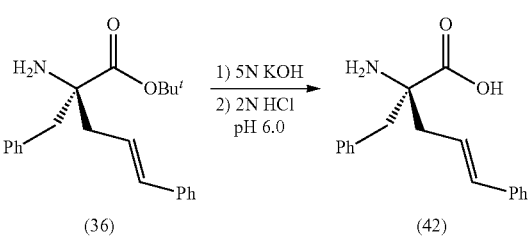

The compound 42 is obtained in a good yield and optical purity in the same manner as in Example 34, except that the cinnamylated product (compound 36) obtained in Example 24 is used instead of the benzylated product (compound 9) obtained by either one of Example 2, 21 or 22.

Example 37

Hydrolysis (4) of Tert-Butyl Ester

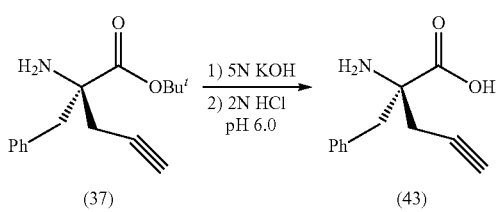

The compound 43 is obtained in a good yield and optical purity in the same manner as in Example 34, except that the propargylated product (compound 37) obtained in Example 25 is used instead of the benzylated product (compound 9) obtained by either one of Example 2, 21 or 22.

Example 38

Hydrolysis (5) of Tert-Butyl Ester

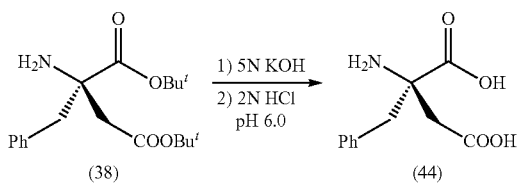

The compound 44 is obtained in a good yield and optical purity in the same manner as in Example 34, except that the tert-butoxycarbonylmethylated product (compound 38) obtained in Example 26 is used instead of the benzylated product (compound 9) obtained by either one of Example 2, 21 or 22.

INDUSTRIAL APPLICABILITY

The present invention provides a chiral phase-transfer catalyst having a simpler configuration. This phase-transfer catalyst can be produced by a fewer number of processes than for a conventional compound, which reduces the cost. Such a phase-transfer catalyst is very useful for synthesis of α-alkyl-α-amino acid and derivatives thereof and α,α-dialkyl-α-amino acid and derivatives thereof. The amino acid and derivatives thereof play a special role in the design of a peptide having enhanced characteristics as an effective enzyme inhibitor and as a chiral structure block for synthesis of compounds having various biological activities. Therefore, the present invention is useful for development of novel foods or pharmaceuticals.

What is claimed is:
1. A method for producing an optically active α-amino acid, comprising:
alkylating a compound represented by the formula (IV):

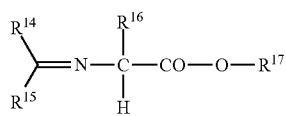

with a compound of the formula (V):

$R^{18}$—W          (V)

to give a compound represented by the formula (VI):

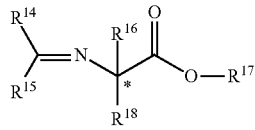

using a compound represented by the formula (I) that is pure with respect to axis symmetry as a phase-transfer catalyst:

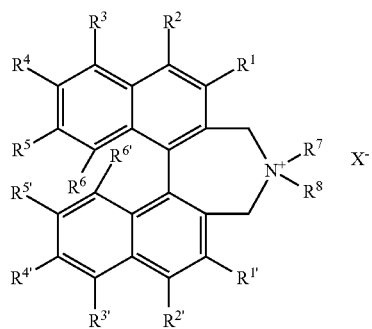

in a medium in the presence of an inorganic base, wherein in the formula (I), $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are groups independently selected from the group consisting of:
  (i) a hydrogen atom;
  (ii) —$NR^{20}R^{21}$ (where $R^{20}$ and $R^{21}$ are each independently a hydrogen atom or a $C_1$ to $C_4$ alkyl group);
  (iii) a cyano group;
  (iv) a nitro group;
  (v) a carbamoyl group;
  (vi) an N—($C_1$ to $C_4$ alkyl)carbamoyl group;
  (vii) an N,N-di($C_1$ to $C_4$ alkyl)carbamoyl group;
  (viii) —$NHCOR^9$ (where $R^9$ is a $C_1$ to $C_4$ alkyl group that may be branched);
  (ix) a $C_1$ to $C_6$ alkyl group that may be branched or form a cyclic group;
  (x) a $C_2$ to $C_6$ alkenyl group that may be branched or form a cyclic group;
  (xi) a $C_2$ to $C_6$ alkynyl group that may be branched or form a cyclic group;
  (xii) an aralkyl group, wherein the aryl moiety of the aralkyl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
    a cyano group,
    —$NR^{20}R^{21}$ (where $R^{20}$ and $R^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched), and
    a halogen atom;
  (xiii) a heteroaralkyl group having a heteroaryl moiety, wherein the heteroaryl moiety may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
    a cyano group,
    —$NR^{20}R^{21}$ (where $R^{20}$ and $R^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched), and
    a halogen atom;

(xiv) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched),
a halogen atom, and
—S—R, —SO—R, or —$SO_2$—R (where R is a $C_1$ to $C_4$ alkyl group that may be branched);
or may be substituted with —O—$CH_2$—O— or —O—$(CH_2)_2$—O— at positions 3 and 4 taken together; and
(xv) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
$R^7$ and $R^8$ are groups independently selected from the group consisting of:
(i) a hydrogen atom;
(ii) a $C_1$ to $C_{12}$ alkyl group that may be branched or form a cyclic group;
(iii) a $C_2$ to $C_{12}$ alkenyl group that may be branched or form a cyclic group;
(iv) a $C_2$ to $C_{12}$ alkynyl group that may be branched or form a cyclic group;
(vii) —$(CH_2)_n OCONR^{10}R^{11}$ (where $R^{10}$ and $R^{11}$ are groups independently selected from the group consisting of:
(1) a hydrogen atom;
(2) a $C_1$ to $C_4$ alkyl group that may be branched;
(3) a $C_2$ to $C_6$ alkenyl group that may be branched or form a cyclic group;
(4) a $C_2$ to $C_6$ alkynyl group that may be branched or form a cyclic group;
(5) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(6) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(7) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and (8) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(viii) —(CH$_2$)$_n$CONR$^{12}$R$^{13}$ (where R$^{12}$ and R$^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and (4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(ix) —(CH$_2$)$_n$NR$^{12}$COR$^{13}$ (where R$^{12}$ and R$^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and (4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(x) —(CH$_2$)$_n$NR$^{12}$R$^{13}$ (where R$^{12}$ and R$^{13}$ are groups independently selected from the group consisting of:

(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(xi) —$(CH_2)_nY$—$OR^{12}$ (where Y is a $C_1$ to $C_4$ divalent saturated hydrocarbon group that may be branched, and $R^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(xii) —$(CH_2)_n$—$OR^{12}$ (where $R^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —$NR^{20}R^{21}$ ($R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched), and a halogen atom;

and n is an integer from 1 to 12);

(xiii) —$(CH_2)_n$—S—$R^{12}$ (where $R^{12}$ is a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched), and a halogen atom; and (4) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched), and a halogen atom;

and n is an integer from 1 to 12);

(xiv) —$(CH_2)_n$—SO—$R^{12}$ (where $R^{12}$ is a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched), and a halogen atom; and (4) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched), a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched), and a halogen atom;

and n is an integer from 1 to 12); and (xv) —$(CH_2)_n$—$SO_2$—$R^{12}$ (where $R^{12}$ is a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom; and (4) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

and n is an integer from 1 to 12); or R$^7$ and R$^8$ are taken together to form a divalent group selected from the group consisting of: —(CH$_2$)$_m$— (where m is an integer from 2 to 8);

[structures shown]

wherein X$^-$ is an anion selected from the group consisting of a halide anion, SCN$^-$, HSO$_4^-$ and HF$_2^-$, provided that in a case where R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are all hydrogen atoms and X– is a halide anion, R$^7$ and R$^8$ are not both methyl groups, a combination of a methyl group and an n-butyl group, a combination of a methyl group and an isopropyl group, or a combination of an allyl group and a hydrogen atom, or R$^7$ and R$^8$ are not taken together to form —(CH$_2$)$_4$—, —(CH$_2$)$_5$— or

[structure shown]

further provided that in a case where R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are all hydrogen atoms and X$^-$ is a bromide ion or an iodide ion, R$^7$ and R$^8$ are not both cyclohexyl groups or allyl groups, in the formulae (IV) and (VI), R$^{14}$ and R$^{15}$ are each independently (i) a hydrogen atom; or (ii) an aryl group that may be substituted with a $C_1$ to $C_4$ alkyl group that may be branched, a $C_1$ to $C_5$ alkoxy group that may be branched, or a halogen atom;

with the proviso the case where both R$^{14}$ and R$^{15}$ are hydrogen atoms is excluded, R$^{16}$ is a group selected from the group consisting of:

(i) a hydrogen atom;

(ii) a $C_1$ to $C_{10}$ alkyl group that may be branched or form a cyclic group;

(iii) a $C_2$ to $C_6$ alkenyl group that may be branched or form a cyclic group;

(iv) a $C_2$ to $C_6$ alkynyl group that may be branched or form a cyclic group;

(v) an aralkyl group, wherein the aryl group of the aralkyl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

(vi) a heteroaralkyl group having a heteroaryl moiety, wherein the heteroaryl moiety may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(vii) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(viii) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
$R^{17}$ is a $C_1$ to $C_8$ alkyl group that may be branched or form a cyclic group),
in the formulae (V) and (VI),
$R^{18}$ is a group selected from the group consisting of:
(i) a $C_1$ to $C_{10}$ alkyl group that may be branched or form a cyclic group;
(ii) a $C_3$ to $C_9$ allyl group or substituted allyl group that may be branched or form a cyclic group;
(iii) a $C_2$ to $C_6$ alkenyl group that may be branched or form a cyclic group;
(iv) a $C_2$ to $C_6$ alkynyl group that may be branched or form a cyclic group;
(v) an aralkyl group, wherein the aryl moiety of the aralkyl group may be substituted with at least one group selected from the group consisting of;
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(vi) a heteroaralkyl group having a heteroaryl moiety, wherein the heteroaryl moiety may be substituted with at least one group selected from the group
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(vii) an aryl group, wherein the aryl group may be substituted with at least one group selected from the group consisting of;
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

(viii) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom; and (ix) a $C_3$ to $C_9$ propargyl group or substituted propargyl group that may be branched, and in the formula (V), W is a functional group having a leaving ability, and in the formula (VI),

* shows a newly produced asymmetric center; and hydrolyzing an imino group (R$^{14}$R$^{15}$C=N—) and an ester group (—CO$_2$R$^{17}$) of the compound represented by the formula (VI):

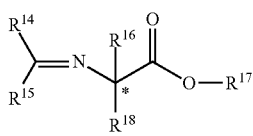

(VI)

under an acidic condition.

2. The method of claim 1, wherein the compound represented by the formula (I) is used in a ratio of 0.001 mol % to 0.1 mol % per 1 mol of the compound represented by the formula (IV).

3. The method of claim 1, wherein the compound represented by the formula (I) is used in a ratio of 0.005 mol % to 0.05 mol % per 1 mol of the compound represented by the formula (IV).

4. A method for producing an optically active α-amino acid, comprising:

alkylating a compound represented by the formula (IV):

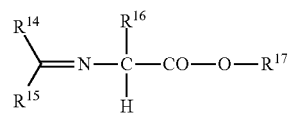

(IV)

with a compound of the formula (V):

R$^{18}$—W  (V)

to give a compound represented by the formula (VI):

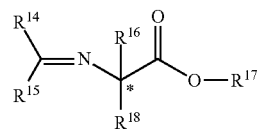

(VI)

using a compound represented by the formula (I) that is pure with respect to axis symmetry as a phase-transfer catalyst:

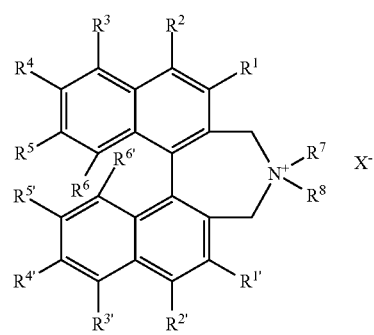

(I)

in a medium in the presence of an inorganic base,
wherein
wherein
in the formula (I),
R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are groups independently selected from the group consisting of:
(i) a hydrogen atom;
(ii) —NR$^{20}$R$^{21}$ (where R$^{20}$ and R$^{21}$ are each independently a hydrogen atom or a $C_1$ to $C_4$ alkyl group);
(iii) a cyano group;
(iv) a nitro group;
(v) a carbamoyl group;
(vi) an N—($C_1$ to $C_4$ alkyl)carbamoyl group;
(vii) an N,N-di($C_1$ to $C_4$ alkyl)carbamoyl group;
(viii) —NHCOR$^9$ (where R$^9$ is a $C_1$ to $C_4$ alkyl group that may be branched);
(ix) a $C_1$ to $C_6$ alkyl group that may be branched or form a cyclic group;
(x) a $C_2$ to $C_6$ alkenyl group that may be branched or form a cyclic group;
(xi) a $C_2$ to $C_6$ alkynyl group that may be branched or form a cyclic group;
(xii) an aralkyl group, wherein the aryl moiety of the aralkyl group may be substituted with at least one group selected from the group consisting of:

a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(xiii) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(xiv) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched),
a halogen atom, and
—S—R, —SO—R, or —$SO_2$—R (where R is a $C_1$ to $C_4$ alkyl group that may be branched);
or may be substituted with —O—$CH_2$—O— or —O—$(CH_2)_2$—O— at positions 3 and 4 taken together; and
(xv) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
$R^7$ and $R^8$ are groups independently selected from the group consisting of:
(i) a hydrogen atom;
(ii) a $C_1$ to $C_{12}$ alkyl group that may be branched or form a cyclic group;
(iii) a $C_2$ to $C_{12}$ alkenyl group that may be branched or form a cyclic group;
(iv) a $C_2$ to $C_{12}$ alkynyl group that may be branched or form a cyclic group;
(vii) —$(CH_2)_n OCONR^{10}R^{11}$ (where $R^{10}$ and $R^{11}$ are groups independently selected from the group consisting of:
(1) a hydrogen atom;
(2) a $C_1$ to $C_4$ alkyl group that may be branched;
(3) a $C_2$ to $C_6$ alkenyl group that may be branched or form a cyclic group;
(4) a $C_2$ to $C_6$ alkynyl group that may be branched or form a cyclic group;
(5) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group, an N,N-di($C_1$ to $C_4$ alkyl)carbamoyl group,
—NHCOR$^9$ (where R$^9$ is a $C_1$ to $C_4$ alkyl group that may be branched), and
a halogen atom;
(6) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(7) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and
(8) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(viii) —(CH$_2$)$_n$CONR$^{12}$R$^{13}$ (where R$^{12}$ and R$^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(ix) —(CH$_2$)$_n$NR$^{12}$COR$^{13}$ (where R$^{12}$ and R$^{13}$ are groups independently selected from the group consisting of:
(1) a hydrogen atom;
(2) a $C_1$ to $C_4$ alkyl group that may be branched;

(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(x) —$(CH_2)_nNR^{12}R^{13}$ (where $R^{12}$ and $R^{13}$ are groups independently selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
and n is an integer from 1 to 12);
(xi) —$(CH_2)_nY$—$OR^{12}$ (where Y is a $C_1$ to $C_4$ divalent saturated hydrocarbon group that may be branched, and $R^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

and n is an integer from 1 to 12);

(xii) —(CH$_2$)$_n$—OR$^{12}$ (where R$^{12}$ is a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom; and (4) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

and n is an integer from 1 to 12);

(xiii) —(CH$_2$)$_n$—S—R$^{12}$ (where R$^{12}$ is a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom; and (4) a heteroaryl group, wherein the heteroaryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched), a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched), and a halogen atom;

and n is an integer from 1 to 12);

(xiv) —(CH$_2$)$_n$—SO—R$^{12}$ (where R$^{12}$ is a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched, a $C_1$ to $C_5$ alkoxy group that may be branched, an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
and n is an integer from 1 to 12); and
(xv) —(CH$_2$)$_n$—SO$_2$—R$^{12}$ (where R$^{12}$ is a group selected from the group consisting of:
(1) a hydrogen atom;
(2) a C$_1$ to C$_4$ alkyl group that may be branched;
(3) an aryl group, wherein the aryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
and n is an integer from 1 to 12); or R$^7$ and R$^8$ are taken together to form a divalent group selected from the group consisting of: —(CH$_2$)$_m$— (where m is an integer from 2 to 8);

wherein X$^-$ is an anion selected from the group consisting of a halide anion, SCN$^-$, HSO$_4^-$ and HF$_2^-$,
provided that in a case where R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are all hydrogen atoms and X– is a halide anion, R$^7$ and R$^8$ are not both methyl groups, a combination of a methyl group and an n-butyl group, a combination of a methyl group and an isopropyl group, or a combination of an allyl group and a hydrogen atom, or R$^7$ and R$^8$ are not taken together to form —(CH$_2$)$_4$—, —(CH$_2$)$_5$— or further provided that in a case where R$^1$, R$^{1'}$, R$^2$, R$^{2'}$, R$^3$, R$^{3'}$, R$^4$, R$^{4'}$, R$^5$, R$^{5'}$, R$^6$, and R$^{6'}$ are all hydrogen atoms and X$^-$ is a bromide ion or an iodide ion, R$^7$ and R$^8$ are not both cyclohexyl groups or allyl groups,
in the formulae (IV) and (VI),
R$^{14}$ and R$^{15}$ are each independently
(i) a hydrogen atom; or
(ii) an aryl group that may be substituted with a C$_1$ to C$_4$ alkyl group that may be branched, a C$_1$ to C$_5$ alkoxy group that may be branched, or a halogen atom;

with the proviso the case where both $R^{14}$ and $R^{15}$ are hydrogen atoms is excluded, $R^{16}$ is a group selected from the group consisting of:
(i) a hydrogen atom;
(ii) a $C_1$ to $C_{10}$ alkyl group that may be branched or form a cyclic group;
(iii) a $C_2$ to $C_6$ alkenyl group that may be branched or form a cyclic group;
(iv) a $C_2$ to $C_6$ alkynyl group that may be branched or form a cyclic group;
(v) an aralkyl group, wherein the aryl group of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(vi) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(vii) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom; and
(viii) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;

$R^{17}$ is a $C_1$ to $C_8$ alkyl group that may be branched or form a cyclic group), in the formulae (V) and (VI), $R^{18}$ is a group selected from the group consisting of:
(i) a $C_1$ to $C_{10}$ alkyl group that may be branched or form a cyclic group;
(ii) a $C_3$ to $C_9$ allyl group or substituted allyl group that may be branched or form a cyclic group;
(iii) a $C_2$ to $C_6$ alkenyl group that may be branched or form a cyclic group;
(iv) a $C_2$ to $C_6$ alkynyl group that may be branched or form a cyclic group;
(v) an aralkyl group, wherein the aryl moiety of the aralkyl group may be substituted with at least one group selected from the group consisting of;
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(vi) a heteroaralkyl group having a heteroaryl moiety, wherein the heteroaryl moiety may be substituted with at least one group selected from the group
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
(vii) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(viii) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(ix) a $C_3$ to $C_9$ propargyl group or substituted propargyl group that may be branched, and in the formula (V),
W is a functional group having a leaving ability, and
in the formula (VI),
* shows a newly produced asymmetric center; and
hydrolyzing an imino group (R$^{14}$R$^{15}$C=N—) of the compound represented by the formula (VI):

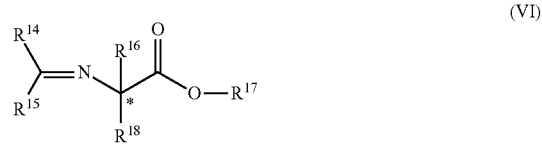

(VI)

under an acidic condition; and
hydrolyzing an ester group (—CO$_2$R$^{17}$) of the acid hydrolyzed product under an acidic or basic condition.

5. The method of claim 4, wherein the compound represented by the formula (I) is used in a ratio of 0.001 mol % to 0.1 mol % per 1 mol of the compound represented by the formula (IV).

6. The method of claim 4, wherein the compound represented by the formula (I) is used in a ratio of 0.005 mol % to 0.05 mol % per 1 mol of the compound represented by the formula (IV).

7. A method for producing an optically active α-amino acid, comprising:
alkylating a compound represented by the formula (IV):

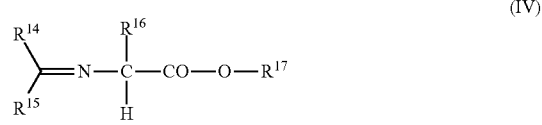

(IV)

with a compound of the formula (V):

(V)

to give a compound represented by the formula (VI):

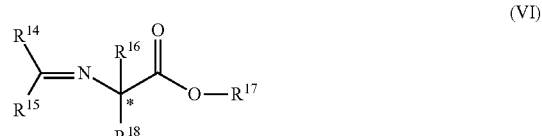

(VI)

using a compound represented by the formula (I) that is pure with respect to axis symmetry as a phase-transfer catalyst:

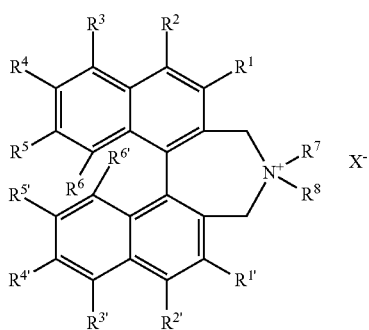

(I)

in a medium in the presence of an inorganic base,
wherein
wherein
in the formula (I),
$R^1, R^{1'}, R^2, R^{2'}, R^3, R^{3'}, R^4, R^{4'}, R^5, R^{5'}, R^6,$ and $R^{6'}$ are groups independently selected from the group consisting of:
(i) a hydrogen atom;
(ii) —$NR^{20}R^{21}$ (where $R^{20}$ and $R^{21}$ are each independently a hydrogen atom or a $C_1$ to $C_4$ alkyl group);
(iii) a cyano group;
(iv) a nitro group;
(v) a carbamoyl group;
(vi) an N—($C_1$ to $C_4$ alkyl)carbamoyl group;
(vii) an N,N-di($C_1$ to $C_4$ alkyl)carbamoyl group;
(viii) —$NHCOR^9$ (where $R^9$ is a $C_1$ to $C_4$ alkyl group that may be branched);
(ix) a $C_1$ to $C_6$ alkyl group that may be branched or form a cyclic group;
(x) a $C_2$ to $C_6$ alkenyl group that may be branched or form a cyclic group;
(xi) a $C_2$ to $C_6$ alkynyl group that may be branched or form a cyclic group;
(xii) an aralkyl group, wherein the aryl moiety of the aralkyl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(xiii) a heteroaralkyl group having a heteroaryl moiety, wherein the heteroaryl moiety may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched), and
a halogen atom;
(xiv) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched),
a halogen atom, and
—S—R, —SO—R, or —$SO_2$—R (where R is a $C_1$ to $C_4$ alkyl group that may be branched);
or may be substituted with —O—$CH_2$—O— or —O—$(CH_2)_2$—O— at positions 3 and 4 taken together; and
(xv) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —$NR^{20}R^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched),
a cyano group,
—$NR^{20}R^{21}$ (where $R^{20}$ and $R^{21}$ are each independently a hydrogen atom or a $C_1$ to $C_4$ alkyl group),
a nitro group,
a carbamoyl group,
an N—($C_1$ to $C_4$ alkyl)carbamoyl group, an N,N-di($C_1$ to $C_4$ alkyl)carbamoyl group,
—NHCOR$^9$ (where R$^9$ is a $C_1$ to $C_4$ alkyl group that may be branched), and
a halogen atom; and
R$^7$ and R$^8$ are groups independently selected from the group consisting of:
  (i) a hydrogen atom;
  (ii) a $C_1$ to $C_{12}$ alkyl group that may be branched or form a cyclic group;
  (iii) a $C_2$ to $C_{12}$ alkenyl group that may be branched or form a cyclic group;
  (iv) a $C_2$ to $C_{12}$ alkynyl group that may be branched or form a cyclic group;
  (vii) —(CH$_2$)$_n$OCONR$^{10}$R$^{11}$ (where R$^{10}$ and R$^{11}$ are groups independently selected from the group consisting of:
    (1) a hydrogen atom;
    (2) a $C_1$ to $C_4$ alkyl group that may be branched;
    (3) a $C_2$ to $C_6$ alkenyl group that may be branched or form a cyclic group;
    (4) a $C_2$ to $C_6$ alkynyl group that may be branched or form a cyclic group;
    (5) an aralkyl group, wherein the aryl moiety of the aralkyl group may be substituted with at least one group selected from the group consisting of:
      a $C_1$ to $C_4$ alkyl group that may be branched,
      a $C_1$ to $C_5$ alkoxy group that may be branched,
      an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
      a cyano group,
      —NR$^{20}$R$^{21}$ (where R$^{20}$ and R$^{21}$ are each independently a hydrogen atom or a $C_1$ to $C_4$ alkyl group),
      a nitro group,
      a carbamoyl group,
      an N—($C_1$ to $C_4$ alkyl)carbamoyl group,
      an N,N-di($C_1$ to $C_4$ alkyl)carbamoyl group,
      —NHCOR$^9$ (where R$^9$ is a $C_1$ to $C_4$ alkyl group that may be branched), and
      a halogen atom;
    (6) a heteroaralkyl group having a heteroaryl moiety, wherein the heteroaryl moiety may be substituted with at least one group selected from the group consisting of:
      a $C_1$ to $C_4$ alkyl group that may be branched,
      a $C_1$ to $C_5$ alkoxy group that may be branched,
      an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
      a cyano group,
      —NR$^{20}$R$^{21}$ (where R$^{20}$ and R$^{21}$ are each independently a hydrogen atom or a $C_1$ to $C_4$ alkyl group),
      a nitro group,
      a carbamoyl group,
      an N—($C_1$ to $C_4$ alkyl)carbamoyl group,
      an N,N-di($C_1$ to $C_4$ alkyl)carbamoyl group,
      —NHCOR$^9$ (where R$^9$ is a $C_1$ to $C_4$ alkyl group that may be branched), and
      a halogen atom;
    (7) an aryl group, wherein the aryl group may be substituted with at least one group selected from the group consisting of:
      a $C_1$ to $C_4$ alkyl group that may be branched,
      a $C_1$ to $C_5$ alkoxy group that may be branched,
      an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
      a cyano group,
      —NR$^{20}$R$^{21}$ (where R$^{20}$ and R$^{21}$ are each independently a hydrogen atom or a $C_1$ to $C_4$ alkyl group),
      a nitro group,
      a carbamoyl group,
      an N—($C_1$ to $C_4$ alkyl)carbamoyl group,
      an N,N-di($C_1$ to $C_4$ alkyl)carbamoyl group,
      —NHCOR$^9$ (where R$^9$ is a $C_1$ to $C_4$ alkyl group that may be branched), and
      a halogen atom;
    and
    (8) a heteroaryl group, wherein the heteroaryl group may be substituted with at least one group selected from the group consisting of:
      a $C_1$ to $C_4$ alkyl group that may be branched,
      a $C_1$ to $C_5$ alkoxy group that may be branched,
      an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
      a cyano group,
      —NR$^{20}$R$^{21}$ (where R$^{20}$ and R$^{21}$ are each independently a hydrogen atom or a $C_1$ to $C_4$ alkyl group),
      a nitro group,
      a carbamoyl group,
      an N—($C_1$ to $C_4$ alkyl)carbamoyl group,
      an N,N-di($C_1$ to $C_4$ alkyl)carbamoyl group,
      —NHCOR$^9$ (where R$^9$ is a $C_1$ to $C_4$ alkyl group that may be branched), and
      a halogen atom;
    and n is an integer from 1 to 12);
  (viii) —(CH$_2$)$_n$CONR$^{12}$R$^{13}$ (where R$^{12}$ and R$^{13}$ are groups independently selected from the group consisting of:
    (1) a hydrogen atom;
    (2) a $C_1$ to $C_4$ alkyl group that may be branched;
    (3) an aryl group, wherein the aryl group may be substituted with at least one group selected from the group consisting of:
      a $C_1$ to $C_4$ alkyl group that may be branched,
      a $C_1$ to $C_5$ alkoxy group that may be branched,
      an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
and n is an integer from 1 to 12);
(ix) —(CH$_2$)$_n$NR$^{12}$COR$^{13}$ (where R$^{12}$ and R$^{13}$ are groups independently selected from the group consisting of:
(1) a hydrogen atom;
(2) a C$_1$ to C$_4$ alkyl group that may be branched;
(3) an aryl group, wherein the aryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom;
and n is an integer from 1 to 12);
(x) —(CH$_2$)$_n$NR$^{12}$R$^{13}$ (where R$^{12}$ and R$^{13}$ are groups independently selected from the group consisting of:
(1) a hydrogen atom;
(2) a C$_1$ to C$_4$ alkyl group that may be branched;
(3) an aryl group, wherein the aryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched), and
a halogen atom; and
(4) a heteroaryl group, wherein the heteroaryl group may be substituted with at least one group selected from the group consisting of:
a C$_1$ to C$_4$ alkyl group that may be branched,
a C$_1$ to C$_5$ alkoxy group that may be branched,
an aryl group that may be substituted with a C$_1$ to C$_4$ alkyl group that may be branched, a cyano group, —NR$^{20}$R$^{21}$ (where R$^{20}$ and R$^{21}$ are each independently a hydrogen atom or a C$_1$ to C$_4$ alkyl group), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched),
a cyano group,
—NR$^{20}$R$^{21}$ (where R$^{20}$ and R$^{21}$ are each independently a hydrogen atom or a C$_1$ to C$_4$ alkyl group), a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(xi) —(CH$_2$)$_n$Y—OR$^{12}$ (where Y is a $C_1$ to $C_4$ divalent saturated hydrocarbon group that may be branched, and R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(xii) —(CH$_2$)$_n$—OR$^{12}$ (where R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);

(xiii) —(CH$_2$)$_n$—S—R$^{12}$ (where R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group, an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12);
(xiv) —(CH$_2$)$_n$—SO—R$^{12}$ (where R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12); and
(xv) —(CH$_2$)$_n$—SO$_2$—R$^{12}$ (where R$^{12}$ is a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom; and
(4) a heteroaryl group, wherein the heteroaryl group may be substituted with at least one group selected from the group consisting of:
a $C_1$ to $C_4$ alkyl group that may be branched,
a $C_1$ to $C_5$ alkoxy group that may be branched,
an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
a cyano group,
—NR$^{20}$R$^{21}$ (where R$^{20}$ and R$^{21}$ are each independently a hydrogen atom or a $C_1$ to $C_4$ alkyl group),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
and n is an integer from 1 to 12); or R$^7$ and R$^8$ are taken together to form a divalent group selected from the group consisting of: —(CH$_2$)$_m$— (where m is an integer from 2 to 8);

wherein X⁻ is an anion selected from the group consisting of a halide anion, SCN⁻, HSO$_4$⁻ and HF$_2$⁻, provided that in a case where $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are all hydrogen atoms and X⁻ is a halide anion, $R^7$ and $R^8$ are not both methyl groups, a combination of a methyl group and an n-butyl group, a combination of a methyl group and an isopropyl group, or a combination of an allyl group and a hydrogen atom, or $R^7$ and $R^8$ are not taken together to form —(CH$_2$)$_4$—, —(CH$_2$)$_5$— or further provided that in a case where $R^1$, $R^{1'}$, $R^2$, $R^{2'}$, $R^3$, $R^{3'}$, $R^4$, $R^{4'}$, $R^5$, $R^{5'}$, $R^6$, and $R^{6'}$ are all hydrogen atoms and X⁻ is a bromide ion or an iodide ion, $R^7$ and $R^8$ are not both cyclohexyl groups or allyl groups, in the formulae (IV) and (VI), $R^{14}$ and $R^{15}$ are each independently
- (i) a hydrogen atom; or
- (ii) an aryl group that may be substituted with a $C_1$ to $C_4$ alkyl group that may be branched, a $C_1$ to $C_5$ alkoxy group that may be branched, or a halogen atom;

with the proviso the case where both $R^{14}$ and $R^{15}$ are hydrogen atoms is excluded, $R^{16}$ is a group selected from the group consisting of:
- (i) a hydrogen atom;
- (ii) a $C_1$ to $C_{10}$ alkyl group that may be branched or form a cyclic group;
- (iii) a $C_2$ to $C_6$ alkenyl group that may be branched or form a cyclic group;
- (iv) a $C_2$ to $C_6$ alkynyl group that may be branched or form a cyclic group;
- (v) an aralkyl group, wherein the aryl group of the aralkyl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched),
  a cyano group,
  —NR$^{20}$R$^{21}$ (where $R^{20}$ and $R^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where $R^9$ is a $C_1$ to $C_4$ alkyl group that may be branched), and
  a halogen atom;
- (vi) a heteroaralkyl group having a heteroaryl moiety, wherein the heteroaryl moiety may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched),
  a cyano group,
  —NR$^{20}$R$^{21}$ (where $R^{20}$ and $R^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where $R^9$ is a $C_1$ to $C_4$ alkyl group that may be branched), and
  a halogen atom;
- (vii) an aryl group, wherein the aryl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched),
  a cyano group,
  —NR$^{20}$R$^{21}$ (where $R^{20}$ and $R^{21}$ are each independently a hydrogen atom or a $C_1$ to $C_4$ alkyl group),
  a nitro group,
  a carbamoyl group,
  an N—($C_1$ to $C_4$ alkyl)carbamoyl group,
  an N,N-di($C_1$ to $C_4$ alkyl)carbamoyl group,
  —NHCOR$^9$ (where $R^9$ is a $C_1$ to $C_4$ alkyl group that may be branched), and
  a halogen atom; and
- (viii) a heteroaryl group, wherein the heteroaryl group may be substituted with at least one group selected from the group consisting of:
  a $C_1$ to $C_4$ alkyl group that may be branched,
  a $C_1$ to $C_5$ alkoxy group that may be branched,
  an aryl group that may be substituted with a $C_1$ to $C_4$ alkyl group that may be branched, a cyano group, —NR$^{20}$R$^{21}$ (where $R^{20}$ and $R^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched),
  a cyano group,
  —NR$^{20}$R$^{21}$ (where $R^{20}$ and $R^{21}$ are each independently a hydrogen atom or a $C_1$ to $C_4$ alkyl group), a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched), and
a halogen atom;
R$^{17}$ is a $C_1$ to $C_8$ alkyl group that may be branched or form a cyclic group),
in the formulae (V) and (VI),
R$^{18}$ is a group selected from the group consisting of:
  (i) a $C_1$ to $C_{10}$ alkyl group that may be branched or form a cyclic group;
  (ii) a $C_3$ to $C_9$ allyl group or substituted allyl group that may be branched or form a cyclic group;
  (iii) a $C_2$ to $C_6$ alkenyl group that may be branched or form a cyclic group;
  (iv) a $C_2$ to $C_6$ alkynyl group that may be branched or form a cyclic group;
  (v) an aralkyl group, wherein the aryl moiety of the aralkyl group may be substituted with at least one group selected from the group consisting of;
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
  (vi) a heteroaralkyl group having a heteroaryl moiety, wherein the heteroaryl moiety may be substituted with at least one group selected from the group
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
  (vii) an aryl group, wherein the aryl group may be substituted with at least one group selected from the group consisting of;
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom;
  (viii) a heteroaryl group, wherein the heteroaryl group may be substituted with at least one group selected from the group consisting of:
    a $C_1$ to $C_4$ alkyl group that may be branched,
    a $C_1$ to $C_5$ alkoxy group that may be branched,
    an aryl group that may be substituted with a $C_1$ to $C_4$ alkyl group that may be branched, a cyano group, —NR$^{20}$R$^{21}$ (where R$^{20}$ and R$^{21}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched),
    a cyano group,
    —NR$^{20}$R$^{21}$ (where R$^{20}$ and R$^{21}$ are each independently a hydrogen atom or a $C_1$ to $C_4$ alkyl group),
    a nitro group,
    a carbamoyl group,
    an N—($C_1$ to $C_4$ alkyl)carbamoyl group,
    an N,N-di($C_1$ to $C_4$ alkyl)carbamoyl group,
    —NHCOR$^9$ (where R$^9$ is a $C_1$ to $C_4$ alkyl group that may be branched), and
    a halogen atom; and
  (ix) a $C_3$ to $C_9$ propargyl group or substituted propargyl group that may be branched, and
in the formula (V),
W is a functional group having a leaving ability, and
in the formula (VI),
* shows a newly produced asymmetric center; and
  hydrolyzing an ester group (—CO$_2$R$^{17}$) of the compound represented by the formula (VI):

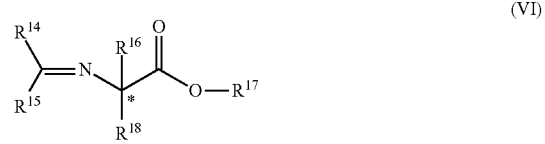

under a basic condition; and
  hydrolyzing an imino group (R$^{14}$R$^{15}$C=N—) of the basic hydrolyzed product under an acidic condition.

8. The method of claim 7, wherein the compound represented by the formula (I) is used in a ratio of 0.001 mol % to 0.1 mol % per 1 mol of the compound represented by the formula (IV).

9. The method of claim 7, wherein the compound represented by the formula (I) is used in a ratio of 0.005 mol % to 0.05 mol % per 1 mol of the compound represented by the formula (IV).

* * * * *